US010857037B2

(12) United States Patent
Jackson et al.

(10) Patent No.: US 10,857,037 B2
(45) Date of Patent: Dec. 8, 2020

(54) CONTROLLED STRAIN SKIN TREATMENT DEVICES AND METHODS

(71) Applicant: Neodyne Biosciences, Inc., Menlo Park, CA (US)

(72) Inventors: Jasper Jackson, Newark, CA (US); John A. Zepeda, Los Altos, CA (US); Geoffrey C. Gurtner, Palo Alto, CA (US); William R. Beasley, Los Altos, CA (US); Paul Yock, Atherton, CA (US); Keiichiro Ichiryu, Campbell, CA (US); Manuel A. Cardona Pamplona, East Palo Alto, CA (US); Tor C. Krog, Seattle, WA (US); Kemal Levi, Mountain View, CA (US); Michael T. Longaker, Atherton, CA (US); Reinhold H. Dauskardt, Menlo Park, CA (US); Michael T. Cao, Milpitas, CA (US); Rene Rodriguez, Santa Clara, CA (US)

(73) Assignee: Neodyne Biosciences, Inc., Newark, CA (US)

(*) Notice: Subject to any disclaimer, the term of this patent is extended or adjusted under 35 U.S.C. 154(b) by 457 days.

(21) Appl. No.: 15/224,393

(22) Filed: Jul. 29, 2016

(65) Prior Publication Data
US 2017/0112673 A1  Apr. 27, 2017

Related U.S. Application Data

(63) Continuation of application No. 13/411,394, filed on Mar. 2, 2012, now abandoned.
(Continued)

(51) Int. Cl.
*A61F 13/00* (2006.01)
*A61F 13/02* (2006.01)
(Continued)

(52) U.S. Cl.
CPC ...... *A61F 13/00038* (2013.01); *A61B 18/203* (2013.01); *A61F 13/00* (2013.01);
(Continued)

(58) Field of Classification Search
CPC .......... A61F 13/00029; A61F 13/00038; A61F 2013/00374; A61F 2013/006
(Continued)

(56) References Cited

U.S. PATENT DOCUMENTS

| 114,750 A | 5/1871 | Battersby |
| 363,538 A | 5/1887 | Penny |

(Continued)

FOREIGN PATENT DOCUMENTS

| AU | 2010282523 A1 | 4/2012 |
| CA | 2321491 A1 | 9/1999 |

(Continued)

OTHER PUBLICATIONS

3M Healthcare. (Date Unknown). "3M™ Steri-Strip™ S Surgical Skin Closure," 3M HealthCare: St. Paul, MN, one page.
(Continued)

*Primary Examiner* — Rachael E Bredefeld
*Assistant Examiner* — Caitlin A Carreiro
(74) *Attorney, Agent, or Firm* — Dorsey & Whitney LLP

(57) ABSTRACT

Devices, kits and methods are used for wound healing, including but not limited to the treatment, amelioration, or prevention of scars and/or keloids, and include packaging, manipulation elements, applicator and/or tensioning device that are used to apply and/or maintain a strain in an elastic dressing.

7 Claims, 28 Drawing Sheets

Related U.S. Application Data

(60) Provisional application No. 61/605,717, filed on Mar. 1, 2012, provisional application No. 61/476,163, filed on Apr. 15, 2011, provisional application No. 61/448,809, filed on Mar. 3, 2011.

(51) Int. Cl.
  *A61B 18/20* (2006.01)
  *A61B 17/00* (2006.01)
  *A61B 18/00* (2006.01)

(52) U.S. Cl.
  CPC ...... *A61F 13/00029* (2013.01); *A61F 13/023* (2013.01); *A61F 13/0223* (2013.01); *A61F 13/0226* (2013.01); *A61F 13/0256* (2013.01); *A61F 13/0259* (2013.01); *A61B 2017/00765* (2013.01); *A61B 2018/0047* (2013.01); *A61F 2013/006* (2013.01); *A61F 2013/00374* (2013.01)

(58) Field of Classification Search
  USPC ....... 606/215, 218; 604/308; 602/41, 52, 53, 602/54, 74
  See application file for complete search history.

(56) References Cited

U.S. PATENT DOCUMENTS

| | | |
|---|---|---|
| 633,050 A | 9/1899 | Spenard |
| 1,074,413 A | 9/1913 | De Baun et al. |
| 1,774,489 A | 8/1930 | Sarason |
| 1,969,188 A | 8/1934 | Spicer |
| 2,018,517 A | 10/1935 | Fetter |
| 2,303,131 A | 11/1942 | Morgan |
| 2,371,978 A | 3/1945 | Perham |
| 2,421,193 A | 5/1947 | Gardner |
| 2,472,009 A | 5/1949 | Gardner |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A * | 8/1977 | Romero-Sierra .... A61B 17/085 606/216 |
| 4,073,298 A | 2/1978 | Le Roy |
| 4,114,624 A | 9/1978 | Haverstock |
| 4,141,363 A | 2/1979 | James et al. |
| 4,173,131 A | 11/1979 | Pendergrass et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | McCracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schäfer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | McLorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | DeBusk et al. |
| 5,649,960 A | 7/1997 | Pavletic |
| 5,662,624 A | 9/1997 | Sundström et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,472,581 B1 | 10/2002 | Muramatsu et al. |
| 6,485,503 B2 | 11/2002 | Jacobs et al. |
| 6,495,230 B1 | 12/2002 | Do Canto |
| 6,570,051 B1 | 5/2003 | Beaudry |
| 6,572,878 B1 | 6/2003 | Blaine |
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |

(56) References Cited

U.S. PATENT DOCUMENTS

| | | | |
|---|---|---|---|
| 6,822,133 B2 | 11/2004 | Lebner | |
| 6,831,205 B2 | 12/2004 | Lebner | |
| 6,870,074 B2 | 3/2005 | Gilman | |
| 6,986,855 B1 | 1/2006 | Hood et al. | |
| 7,066,182 B1 | 6/2006 | Dunshee | |
| 7,066,934 B2 | 6/2006 | Kirsch | |
| 7,122,712 B2 | 10/2006 | Lutri et al. | |
| 7,135,606 B1 | 11/2006 | Dozier et al. | |
| 7,227,050 B2 | 6/2007 | Sigurjonsson et al. | |
| 7,332,641 B2 | 2/2008 | Lebner et al. | |
| 7,354,446 B2 | 4/2008 | Lebner | |
| 7,414,168 B2 | 8/2008 | Lebner | |
| 7,456,332 B2 | 11/2008 | Beaudry | |
| 7,511,185 B2 | 3/2009 | Lebner | |
| 7,563,941 B2 | 7/2009 | Lebner et al. | |
| 7,683,234 B2 | 3/2010 | Gurtner et al. | |
| 7,834,232 B2 | 11/2010 | Rastegar et al. | |
| RE42,126 E | 2/2011 | Ye et al. | |
| 8,063,263 B2 | 11/2011 | Gurtner et al. | |
| 8,168,850 B2 | 5/2012 | Gurtner et al. | |
| 8,183,428 B2 | 5/2012 | Gurtner et al. | |
| 8,389,791 B2 | 3/2013 | Gurtner et al. | |
| 8,395,011 B2 | 3/2013 | Zepeda et al. | |
| 8,592,640 B2 | 11/2013 | Zepeda et al. | |
| 8,674,164 B2 | 3/2014 | Zepeda et al. | |
| 9,248,048 B2 | 2/2016 | Jackson et al. | |
| 9,248,049 B2 | 2/2016 | Gurtner et al. | |
| 9,248,051 B2 | 2/2016 | Gurtner et al. | |
| 9,358,009 B2 | 6/2016 | Yock et al. | |
| 9,492,329 B2 | 11/2016 | Zepeda et al. | |
| 2002/0013300 A1 | 1/2002 | Capelli-Schellpfeffer | |
| 2002/0193723 A1 | 12/2002 | Batdorf, Sr. et al. | |
| 2003/0014053 A1 | 1/2003 | Nguyen et al. | |
| 2003/0040687 A1 | 2/2003 | Boynton et al. | |
| 2003/0092969 A1* | 5/2003 | O'Malley | A61B 17/02 600/216 |
| 2003/0220700 A1 | 11/2003 | Hammer et al. | |
| 2005/0033215 A1 | 2/2005 | Lebner | |
| 2005/0034731 A1 | 2/2005 | Rousseau et al. | |
| 2005/0070956 A1 | 3/2005 | Rousseau | |
| 2005/0080453 A1 | 4/2005 | Lebner | |
| 2005/0095275 A1 | 5/2005 | Zhu et al. | |
| 2005/0095276 A1 | 5/2005 | Kartheus et al. | |
| 2005/0125051 A1 | 6/2005 | Eidenschink et al. | |
| 2005/0245966 A1 | 11/2005 | Hammerslag et al. | |
| 2005/0274453 A1 | 12/2005 | Anvar | |
| 2005/0283141 A1 | 12/2005 | Giovannoli | |
| 2006/0009099 A1 | 1/2006 | Jonn et al. | |
| 2006/0020235 A1 | 1/2006 | Siniaguine | |
| 2006/0037091 A1 | 2/2006 | Gurtner et al. | |
| 2006/0246802 A1 | 11/2006 | Hughes et al. | |
| 2006/0282135 A1 | 12/2006 | Tankovich | |
| 2007/0093161 A1 | 4/2007 | Eede et al. | |
| 2007/0129776 A1 | 6/2007 | Robins et al. | |
| 2007/0142761 A1 | 6/2007 | Aali | |
| 2007/0191752 A1 | 8/2007 | Lebner | |
| 2007/0239232 A1 | 10/2007 | Kurtz et al. | |
| 2007/0282235 A1 | 12/2007 | Beaudry | |
| 2007/0282374 A1 | 12/2007 | Sogard et al. | |
| 2008/0033334 A1 | 2/2008 | Gurtner et al. | |
| 2008/0051687 A1 | 2/2008 | Rogers | |
| 2008/0172047 A1 | 7/2008 | Altshuler et al. | |
| 2008/0208098 A1 | 8/2008 | Rennix | |
| 2008/0228220 A1 | 9/2008 | Weiser | |
| 2009/0131845 A1 | 5/2009 | Gurtner et al. | |
| 2009/0131846 A1 | 5/2009 | Gurtner et al. | |
| 2009/0163844 A1 | 6/2009 | Gurtner et al. | |
| 2009/0177136 A1* | 7/2009 | Liedtke | A61F 13/0203 602/58 |
| 2010/0191253 A1 | 7/2010 | Oostman, Jr. et al. | |
| 2010/0280428 A1 | 11/2010 | Widgerow et al. | |
| 2011/0152738 A1 | 6/2011 | Zepeda et al. | |
| 2011/0319798 A1 | 12/2011 | DiGrazia | |
| 2012/0035521 A1 | 2/2012 | Zepeda et al. | |
| 2012/0046586 A1 | 2/2012 | Gurtner et al. | |
| 2012/0046590 A1 | 2/2012 | Yock et al. | |
| 2012/0046591 A1 | 2/2012 | Gurtner et al. | |
| 2012/0083724 A1 | 4/2012 | Zepeda et al. | |
| 2012/0203273 A1 | 8/2012 | Riskin et al. | |
| 2012/0221044 A1 | 8/2012 | Archibald et al. | |
| 2012/0226214 A1 | 9/2012 | Gurtner et al. | |
| 2012/0226306 A1 | 9/2012 | Jackson et al. | |
| 2013/0012858 A1 | 1/2013 | Jackson et al. | |
| 2013/0184629 A1 | 7/2013 | Gurtner et al. | |
| 2013/0190673 A1 | 7/2013 | Gurtner et al. | |
| 2013/0281904 A1 | 10/2013 | Jackson et al. | |
| 2014/0088481 A1 | 3/2014 | Jackson et al. | |
| 2014/0135677 A1 | 5/2014 | Zepeda et al. | |
| 2014/0135678 A1 | 5/2014 | Zepeda et al. | |
| 2016/0213522 A1 | 7/2016 | Gurtner et al. | |
| 2017/0020522 A1 | 1/2017 | Yock et al. | |
| 2019/0015255 A1 | 1/2019 | Gurtner et al. | |

FOREIGN PATENT DOCUMENTS

| | | |
|---|---|---|
| CA | 2621387 A1 | 3/2007 |
| CA | 2659772 A1 | 2/2008 |
| CN | 1414842 A | 4/2003 |
| CN | 1608604 A | 4/2005 |
| CN | 102665623 A | 9/2012 |
| EP | 2 161 011 A1 | 3/2010 |
| EP | 2 464 322 A2 | 6/2012 |
| JP | 2004-515256 A | 5/2004 |
| JP | 2004-223087 A | 8/2004 |
| JP | 2004-536898 A | 12/2004 |
| JP | 2006-513748 A | 4/2006 |
| JP | 2007-537781 A | 12/2007 |
| JP | 2009-545382 A | 12/2009 |
| JP | 2013-501591 A | 1/2013 |
| KR | 20080007084 A | 1/2008 |
| KR | 20100004700 A | 8/2010 |
| KR | 20100129958 A | 12/2010 |
| KR | 20140020993 A | 2/2014 |
| RU | 2 019 138 C1 | 9/1994 |
| RU | 2019138 C1 | 9/1994 |
| WO | WO-97/17919 A1 | 5/1997 |
| WO | WO-97/30700 A2 | 8/1997 |
| WO | WO-97/30700 A3 | 8/1997 |
| WO | WO-00/53139 A1 | 9/2000 |
| WO | WO-01/39693 A2 | 6/2001 |
| WO | WO-01/39693 A3 | 6/2001 |
| WO | WO-02/15816 A2 | 2/2002 |
| WO | WO-02/15816 A3 | 2/2002 |
| WO | WO-02/45698 A2 | 6/2002 |
| WO | WO-02/45698 A3 | 6/2002 |
| WO | WO-02/092783 A2 | 11/2002 |
| WO | WO-02/092783 A3 | 11/2002 |
| WO | WO-2002/087645 A1 | 11/2002 |
| WO | WO-2004/060413 A1 | 7/2004 |
| WO | 2004073567 A1 | 9/2004 |
| WO | WO-2005/079674 A1 | 9/2005 |
| WO | WO-2005/096981 A2 | 10/2005 |
| WO | WO-2005/096981 A3 | 10/2005 |
| WO | WO-2006/124671 A2 | 11/2006 |
| WO | WO-2006/124671 A3 | 11/2006 |
| WO | WO-2008/019051 A2 | 2/2008 |
| WO | WO-2008/019051 A3 | 2/2008 |
| WO | WO-2011/019859 A2 | 2/2011 |
| WO | WO-2011/019859 A3 | 2/2011 |
| WO | WO-2012/094648 A1 | 7/2012 |
| WO | WO-2012/119131 A1 | 9/2012 |

OTHER PUBLICATIONS

3M Healthcare. (Date Unknown). "3M™ Steri-Strip™ S Surgical Skin Closure. Poster of Available Sizes," 3M HealthCare: St. Paul, MN, three pages.

3M Healthcare. (2001). "Reducing the Risk of Superficial Skin Damage Related to Adhesive Use," 3M HealthCare: St. Paul, MN, two pages.

3M Healthcare. (Jun. 27, 2002). "3M™ Steri-Strip™ Adhesive Skin Closures (reinforced): Commonly Asked Questions," 3M HealthCare: St. Paul, MN, pp. 1-4.

(56) References Cited

OTHER PUBLICATIONS

3M Healthcare. (2003). "Steri-Strip: Skin Closures," Product Insert, 3M HealthCare: St. Paul, MN, one page.
3M Healthcare. (May 2004). "Tips for Trouble-Free Taping," 3M HealthCare: St. Paul, MN, four pages.
3M Healthcare. (2006). "3M™ Steri-Strip™ S Surgical Skin Closure. The Simple, Non-Invase Alternative to Staples and Sutures from the Steri-Strip Family," HealthCare: St. Paul, MN, two pages.
3M Healthcare. (Oct. 19, 2006). "3M™ Steri-Strip™ S Surgical Skin Closure: Commonly Asked Questions," 3M HealthCare: St. Paul, MN, pp. 1-8.
3M Healthcare. (2007). "3M™ Steri-Strip™ S Surgical Skin Closure. Application Instructions," 3M HealthCare: St. Paul, MN, two pages.
3M Medical. (2006). "They Say Every Scar Tells a Story," 3M HealthCare: St. Paul, MN, one page.
3M Medical. (2006). "3M™ Steri-Strip™ S Surgical Skin Closure. Patient Care Information," 3M HealthCare: St. Paul, MN, two pages.
3M Medical. (2007). "3M™ Steri-Strip™ S Surgical Skin Closure. Application Examples, Comparisons and Results," 3M HealthCare: St. Paul, MN, four pages.
Aarabi, S. et al. (Oct. 2007). "Mechanical Load Initiates Hypertrophic Scar Formation Through Decreased Cellular Apoptosis," *The FASEB Journal* 21(12):3250-3261.
Advisory Action dated Feb. 4, 2014, for U.S. Appl. No. 13/029,023, filed Feb. 16, 2011, 4 pages.
Advisory Action received for U.S. Appl. No. 13/789,264, dated Oct. 19, 2015, 3 pages.
Advisory Action received for U.S. Appl. No. 13/789,237, dated Oct. 8, 2015, 5 pages.
Advisory Action dated Jan. 13, 2017, for U.S. Appl. No. 13/411,443, filed Mar. 2, 2012, 3 pages.
Al-Attar, A. et al. (Jan. 2006). "Keloid Pathogenesis and Treatment," *Plastic and Reconstructive Surgery* 117(1): 286-300.
Angelini, G.D. et al. (1984). "Comparative Study of Leg Wound Skin Closure in Coronary Artery Bypass Graft Operations," *Thorax* 39:942-945.
Anonymous (2003). "3M™ Steri-Strip™ Adhesive Skin Closures," 3M HealthCare Brochure, twelve pages.
Anonymous. (2005). "3M™ Tegaderm™ Family of Transparent Dressings," 3M HealthCare Brochure, six pages.
Anonymous. (2006). "Avocet Polymer Technologies," located at <http://www.avocetcorp.com/index.html>, last visited on Nov. 5, 2007, one page.
Anonymous. (2006). "Avogel Scar Hydrogel," located at <http://www.avocetcorp.com/avogel_scar_hydrogel.html>, last visited on Nov. 5, 2007, two pages.
Anonymous. (2006). "Avosil Ointment," located at <http://www.avocetcorp.com/avosil.html>, last visited on Nov. 5, 2007, three pages.
Anonymous. (Date Unknown). "Mepiform Instructions of Use," Tendra Corporation Brochure, two pages.
Anonymous. (Date Unknown). "Silicone Scar Bandage: Standard Wound Healing Application," located at <http://www.thejamushop.com/silicon_sheet_for_keloids.htm>, last visited on Mar. 18, 2009, four pages.
Atkinson, J-A.M. et al. (Nov. 2005). "A Randomized, Controlled Trial to Determine the Efficacy of Paper Tape in Preventing Hypertrophic Scar Formation in Surgical Incisions that Traverse Langer's Skin Tension Lines," *Plastic and Reconstructive Surgery* 116(6):1648-1656.
Bachert, B. et al. (2003). "Probing Elastic Modulus and Depth of a Two Layer Human Skin Model with Piezoelectric Cantilevers," Biomedical Engineering Senior Design Team, Drexel Univ., 27 pages.
Berman, B. et al. (Mar. 3, 2005). "Keloid and Hypertrophic Scar," located at <http://www.emedicine.com/DERM/topic205.htm>, last visited on Nov. 19, 2007, 23 pages.

Brace, "Definition of Brace", Merriam Webster, Available Online at <www.merriam-webster.com>, 2015, 4 pages.
Bunker, T.D. (1983). "Problems with the Use of Op-Site Sutureless Skin Closures in Orthopaedic Procedures," *Annals of the Royal College of Surgeons of England* 65:260-262.
Burd, A. et al. (Dec. 2005). "Hypertrophic Response and Keloid Diathesis: Two Very Different Forms of Scar," *Plastic and Reconstructive Surgery* 116(7):150-157.
Canica Design Inc. (Date Unknown). "ABRA® Abdominal Wall Closure Set," located at <http://www.canica.com/instructions/1D1544RA%20-%20ABRA%20CWK08%20IFU.pdf>, last visited on Sep. 10, 2009, pp. 1-11.
Canica Design Inc. (Date Unknown). "ABRA® Surgical Skin Closure Set," located at <http://www.canica.com/instructions/1D0830RH.pdf>, last visited on Sep. 10, 2009, pp. 1-4.
Chen, H-H. et al. (Jul. 2001). "Prospective Study Comparing Wounds Closed With Tape With Sutured Wounds in Colorectal Surgery," *Arch. Surg.* 136:801-803.
Corrected Notice of Allowance dated Jan. 23, 2013, for U.S. Appl. No. 13/315,214, filed Dec. 8, 2011, 2 pages.
Davison, S.P. et al. (Jan. 2006). "Ineffective Treatment of Keloids with Interferon Alpha-2b," *Plastic and Reconstructive Surgery* 117(1):247-252.
Escoffier, C. et al. (Sep. 1989). "Age-Related Mechanical Properties of Human Skin: An In Vivo Study," *J. Invest. Dermatol.* 9(3)3:353-357.
Evans, S.L. et al. (2009). "Measuring the Mechanical Properties of Human Skin in vivo Using Digital Correlation and Finite Element Modeling," *J. Strain Analysis* 44:337-345.
Extended European Search Report dated Aug. 19, 2013 for European Patent Application No. 10 808 724.8, filed on Aug. 11, 2010, 8 pages.
Extended European Search Report dated Feb. 23, 2016, for European Patent Application No. 13 825 488.3, filed on Feb. 8, 2013, 6 pages.
Extended European Search Report received for European Patent Application No. 12732236.0, dated Jun. 29, 2015, 6 pages.
Extended European Search Report received for European Patent Application No. 12752239.9, dated Oct. 1, 2014, 7 pages.
Fairclough, J.A. et al. (1987). "The Use of Sterile Adhesive Tape in the Closure of Arthroscopic Puncture Wounds: A Comparison with a Single Layer Nylon Closure," *Annals of the Royal College of Surgeons of England* 69:140-141.
Final Office Action received for U.S. Appl. No. 13/411,443 dated Jun. 3, 2015, 13 pages.
Final Office Action received for U.S. Appl. No. 13/789,237, dated Aug. 27, 2015, 9 pages.
Final Office Action received for U.S. Appl. No. 13/789,264, dated Jul. 16, 2015, 11 pages.
Final Office Action received for U.S. Appl. No. 13/029,023, dated Nov. 25, 2013, 12 pages.
Final Office Action received for U.S. Appl. No. 13/411,394, dated Mar. 18, 2014, 12 pages.
Final Office Action received for U.S. Appl. No. 13/789,229, dated Jan. 15, 2015, 21 pages.
Final Office Action received for U.S. Appl. No. 13/411,394, dated Feb. 1, 2016, 14 pages.
Final Office Action dated May 23, 2013, for U.S. Appl. No. 13/089,105, filed Apr. 18, 2011, 14 pages.
Final Office Action dated Oct. 20, 2016, for U.S. Appl. No. 13/411,443, filed Mar. 2, 2012, 15 pages.
Gorney, M. (Mar. 2006). "Scar: The Trigger to the Claim," *Plastic and Reconstructive Surgery* 117(3):1036-1037.
Hof, M. et al. (Jul. 2006). "Comparing Silicone Pressure-Sensitive Adhesives to Silicone Gels for Transdermal Drug Delivery," presented at *33 Annual Meeting and Exposition of the Controlled Release Society*, Vienna, Austria, Jul. 22-26, 2006, seven pages.
International Search Report and Written Opinion received for PCT Patent Application No. PCT/US2013/025449, dated Feb. 5, 2015, 8 pages.
International Search Report and Written Opinion dated Feb. 7, 2008, for PCT Application No. PCT/US2007/017320, filed on Aug. 3, 2007, 11 pages.

(56) References Cited

OTHER PUBLICATIONS

International Search Report and Written Opionion dated Feb. 8, 2011, for PCT Patent Application No. PCT/US2010/045239, filed on Aug. 11, 2010, one page.
International Search Report and Written Opinion dated May 1, 2012, for PCT Patent Application No. PCT/US2012/020561, filed Jan. 6, 2012, three pages.
International Search Report dated May 29, 2012, for PCT Patent Application No. PCT/US2012/25510, filed Feb. 16, 2012, four pages.
International Search Report dated Jun. 28, 2012, for PCT Patent Application No. PCT/US2012/027618, filed Mar. 2, 2012, two pages.
Koval, K.J. et al. (Oct. 2003). "Tape Blisters Following Hip Surgery. A Prospective Randomized Study of Two Types of Tape," *The Journal of Bone and Joint Surgery* 85-5(10):1884-1887.
Kuo, F. et al. (May 2006). "Prospective, Randomized, Blinded Study of a New Wound Closure Film Versus Cutaneous Suture for Surgical Wound Closure," *Dermatological Surgery* 32(5):676-681.
Mask, "Definition of Mask", Merriam Webster, Available Online at <www.merriam-webster.com>, 2015, 4 pages.
Mustoe, T.A. et al. (Nov. 2005). "A Randomized, Controlled Trial to Determine the Efficacy of Paper Tape in Preventing Hypertrophic Scar Formation in Surgical Incisions that Traverse Langer's Skin Tension Lines," *Plastic and Reconstructive Surgery* (Discussion) 116(6):1657-1658.
Nahabedian, M.Y. (Dec. 2005). "Scar Wars: Optimizing Outcomes with Reduction Mammaplasty," *Plastic and Reconstructive Surgery* 116(7):2026-2029.
NHSSB Wound Management Manual, Northern Health and Social Services Board, 2005, pp. 1-97.
Non-Final Office Action dated Apr. 13, 2009, for U.S. Appl. No. 11/888,978, filed Aug. 3, 2007, 20 pages.
Non-Final Office Action dated Mar. 7, 2011, for U.S. Appl. No. 12/358,159, filed Jan. 22, 2009, 14 pages.
Non-Final Office Action dated Aug. 5, 2011, for U.S. Appl. No. 12/358,162, filed Jan. 22, 2009, 13 pages.
Non-Final Office Action dated Aug. 5, 2011, for U.S. Appl. No. 12/358,164, filed Jan. 22, 2009, 15 pages.
Non-Final Office Action dated Aug. 8, 2012, for U.S. Appl. No. 13/089,104, filed Apr. 18, 2011, 13 pages.
Non-Final Office Action dated May 9, 2012, for U.S. Appl. No. 13/315,214, filed Dec. 8, 2011, 6 pages.
Non-Final Office Action dated Jul. 20, 2012, for U.S. Appl. No. 13/089,105, filed Apr. 18, 2011, 17 pages.
Non-Final Office Action dated Aug. 21, 2012, for U.S. Appl. No. 13/315,214, filed Dec. 8, 2011, 5 pages.
Non-Final Office Action dated Mar. 15, 2013, for U.S. Appl. No. 13/029,023, filed Feb. 16, 2011, 8 pages.
Non-Final Office Action received for U.S. Appl. No. 13/411,443, dated Jan. 13, 2016, 14 pages.
Non Final Office Action received for U.S. Appl. No. 13/089,129, dated Jun. 28, 2013, 11 pages.
Non Final Office Action received for U.S. Appl. No. 13/029,023, dated Jun. 10, 2015, 12 pages.
Non-Final Office Action received for U.S. Appl. No. 13/029,023, dated Aug. 14, 2014, 12 pages.
Non Final Office Action received for U.S. Appl. No. 13/089,105, dated Dec. 5, 2013, 14 pages.
Non-Final Office Action received for U.S. Appl. No. 13/089,105 dated Jul. 10, 2014, 8 pages.
Non-Final Office Action received for U.S. Appl. No. 13/089,105, dated Apr. 10, 2015, 15 pages.
Non-Final Office Action received for U.S. Appl. No. 13/345,524, dated Apr. 10, 2015, 12 pages.
Non-Final Office Action received for U.S. Appl. No. 13/345,524, dated Mar. 28, 2014, 12 pages.
Non-Final Office Action received for U.S. Appl. No. 13/411,394, dated Apr. 10, 2015, 15 pages.
Non-Final Office Action received for U.S. Appl. No. 13/411,443, dated Jan. 16, 2015, 12 pages.
Non Final Office Action received for U.S. Appl. No. 13/789,204, dated Oct. 8, 2014, 8 pages.
Non-Final Office Action received for U.S. Appl. No. 13/789,229, dated Jun. 4, 2014, 6 pages.
Non Final Office Action received for U.S. Appl. No. 13/789,237, dated Mar. 31, 2014, 5 pages.
Non-Final Office Action received for U.S. Appl. No. 13/789,264, dated Mar. 26, 2014, 10 pages.
Non-Final Office Action received for U.S. Appl. No. 13/789,512, dated Jan. 25, 2016, 9 pages.
Non-Final Office Action received for U.S. Appl. No. 14/158,741, dated Dec. 16, 2015, 9 pages.
Non-Final Office Action dated Mar. 29, 2013, for U.S. Appl. No. 12/854,859, dated Aug. 11, 2010, 11 pages.
Non-Final Office Action dated Dec. 1, 2016, for U.S. Appl. No. 15/002,253, dated Jan. 20, 2016, 10 pages.
Non-Final Office Action dated Feb. 2, 2017, for U.S. Appl. No. 15/002,253, dated Jan. 20, 2016, 11 pages.
Northern Health and Social Services Board. (2005). *NHSSB Wound Management Manual*, pp. 1-97.
Notice of Allowance dated Jan. 19, 2010, for U.S. Appl. No. 11/888,978, filed Aug. 3, 2007, eight pages.
Notice of Allowance dated Oct. 11, 2011, for U.S. Appl. No. 12/358,159, filed Jan. 22, 2009, five pages.
Notice of Allowance dated Dec. 29, 2011, for U.S. Appl. No. 12/358,162, filed Jan. 22, 2009, eight pages.
Notice of Allowance dated Dec. 29, 2011, for U.S. Appl. No. 12/358,164, filed Jan. 22, 2009, seven pages.
Notice of Allowance dated Feb. 17, 2012, for U.S. Appl. No. 12/358,164, filed Jan. 22, 2009, eight pages.
Notice of Allowance dated Mar. 2, 2012, for U.S. Appl. No. 12/358,162, filed Jan. 22, 2009, eight pages.
Notice of Allowance dated Dec. 10, 2012, for U.S. Appl. No. 13/315,214, filed Dec. 8, 2011, eight pages.
Notice of Allowance dated Jan. 23, 2013, for U.S. Appl. No. 13/315,214, filed Dec. 8, 2011, two pages.
Notice of Allowance dated Jan. 8, 2013, for U.S. Appl. No. 13/089,104, filed Apr. 18, 2011, nine pages.
Notice of Allowance dated Oct. 9, 2013, for U.S. Appl. No. 12/854,859, filed Aug. 11, 2010, 7 pages.
Notice of Allowance dated Feb. 12, 2016, for U.S. Appl. No. 13/029,023, filed Feb. 16, 2011, 9 pages.
Notice of Allowance received for U.S. Appl. No. 13/089,129, dated Oct. 28, 2013, 7 pages.
Notice of Allowance received for U.S. Appl. No. 13/089,105, dated Nov. 20, 2015, 5 pages.
Notice of Allowance dated Jul. 6, 2016, for U.S. Appl. No. 14/158,741, filed Jan. 17, 2014, 8 pages.
Notice of Allowance received for U.S. Appl. No. 13/789,237, dated Nov. 24, 2015, 5 pages.
Notice of Allowance dated Jan. 11, 2017, for U.S. Appl. No. 14/158,688, filed Jan. 17, 2014, 8 pages.
Notice of Allowance received for U.S. Appl. No. 13/345,524, dated Oct. 5, 2015, 9 pages.
O'Brien, L. et al. (2009). "Silicon Gel Sheeting for Preventing and Treating Hypertrophic and Keloid Scars," *The Cochrane Collaboration* pp. 1-47.
Pitcher, D. (Feb. 1983). "Sutureless Skin Closure for Pacemaker Implantation: Comparison with Subcuticular Suture," *Postgraduate Medical Journal* 59:83-85.
Shanghai Dongyue Medical Health Product Co., Ltd. (2005). Silicon-gel Membrane—Scar Bandage, located at <http://www.shdongyue.com/cp/shaos/shaos02b.asp>, last visited on Nov. 6, 2008, two pages.
Shirado, H. et al. (Mar. 2006). "Realization of Human Skin-Like Texture by Emulating Surface Shape Pattern and Elastic Structure," presented at *Symposium on Haptic Interfaces for Virtual Environment and Teleoperator Systems 2006*, Mar. 25-26, 2006, Alexandria, VA, pp. 295-296.

(56) References Cited

OTHER PUBLICATIONS

Smith & Nephew. (Date Unknown). "CICA-CARE. Silicone Gel Sheeting," located at <http://wound.smith-nepehew.com/za/Product/asp?NodeId=569&Tab=5&hide=True>, last visited on Jun. 9, 2009, one page.

Sullivan, S.R. et al. (2007). "Acute Wound Care," Chapter 7 in *ACS Surgery: Principles and Practice,* 24 pages.

Téot, L. (2005). "Scar Control" *European Tissue Repair Society,* located at <http://www.etrs.org/bulletin12_1/section11.php>, last visited on Nov. 30, 2007, 13 pages.

Vaughan, P. et al. (2006). "Optimal Closure of Surgical Wounds in Forefoot Surgery: Are Adhesive Strips Beneficial?" *Acta Orthop. Belg.* 72(6):731-733.

Vowden, K. (Mar. 2003). "Wound Management. Policy and Resource Pack," Bradford Teaching Hospitals NHS Foundation Trust, pp. 1-70.

Watson, G.M. (1983). "Op-Site Skin Closure: A Comparison with Subcuticular and Interrupted Sutures," *Annals of the Royal College of Surgeons of England* 65:83-84.

Webster, D.J.T. et al. (Sep. 1975). "Closure of Abdominal Wounds by Adhesive Strips: A Clinical Trial," *British Medical Journal* 20:696-698.

Westaby, S. (1980). "Evaluation of a New Product for Sutureless Skin Closure," *Annals of the Royal College of Surgeons of England* 62:129-132.

Wound Care Technologies. (2008). "DERMAClose™ RC: Continuous External Tissue Expander, Brochure No. PL-0020-F," located at < http://www.woundcaretech.com/sell-sheet.pdf>, last visited on Sep. 10, 2009, two pages.

Wound Care Technologies. (2008). "Instructions for Use. DERMAClose™ RC, Brochure No. DR-0079-A," located at < http://www.dermaclose.com/instructions.pdf>, last visited on Sep. 10, 2009, two pages.

Written Opinion of the International Searching Authority dated May 29, 2012, for PCT Application No. PCT/US2012/25510, filed on Feb. 16, 2012, 8 pages.

Written Opinion of the International Searching Authority dated Jun. 28, 2012, for PCT Application No. PCT/US2012/027618, filed Mar. 2, 2012, 10 pages.

U.S. Appl. No. 15/224,393, filed Jul. 29, 2016, by Jackson et al.

U.S. Patent Application No. 15/293,084, filed Oct. 13, 2016, by Zepeda et al.

\* cited by examiner

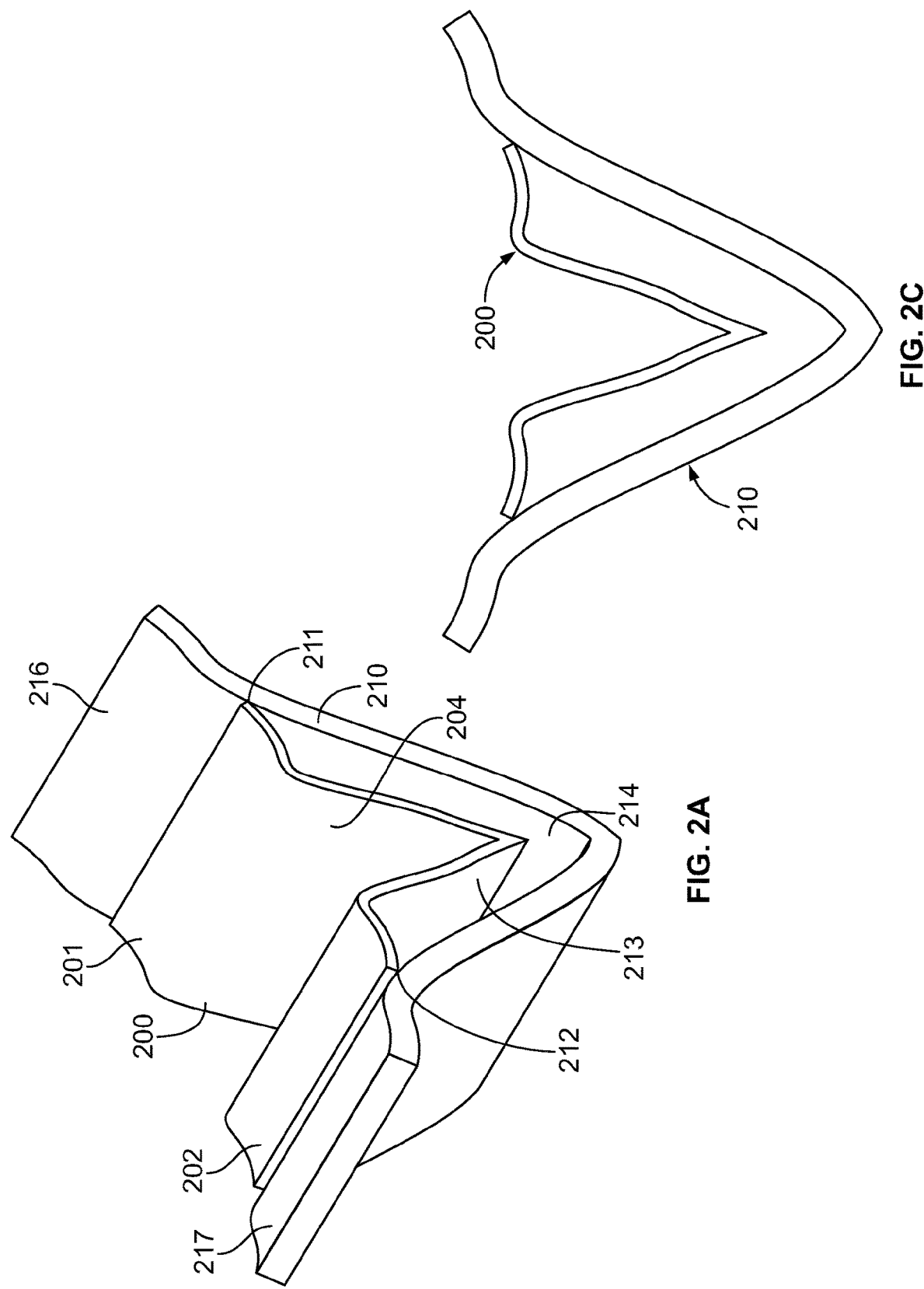

CONTROLLED STRAIN SKIN TREATMENT DEVICES AND METHODS

CROSS-REFERENCE TO RELATED APPLICATIONS

This application is a continuation of U.S. patent application Ser. No. 13/411,394, filed on Mar. 2, 2012, which claims benefit under 35 U.S.C. § 119(e) to a) U.S. Provisional Application Ser. No. 61/448,809, filed on Mar. 3, 2011, b) U.S. Provisional Application Ser. No. 61/476,163, filed on Apr. 15, 2011, and c) U.S. Provisional Application Ser. No. 61/605,717, filed on Mar. 1, 2012, all of which are hereby incorporated by reference in their entirety. This application is also related to U.S. application Ser. No. 11/888,978, filed on Aug. 3, 2007, and U.S. application Ser. No. 12/854,859, filed on Aug. 11, 2010, all of which are hereby incorporated by reference in their entirety.

BRIEF SUMMARY

Devices, kits and methods described herein may be for treatment of a subject at a skin site including without limitation for wound treatment or the treatment, amelioration, or prevention of scars and/or keloids, by manipulating mechanical or physical properties of skin or by shielding skin from stresses, and/or by controllably stressing or straining the epidermis and layers of dermal tissue at or near a skin site, i.e., at or adjacent a wound or a treatment site of a subject's skin. According to variations, manipulating mechanical or physical properties may thereby modulate tensile or compressive stress at the skin site. The stress at the skin site may be reduced to levels below that experienced by normal skin and tissue. The stress at the skin site may be increased to levels above that experienced by normal skin and tissue. The stress or strain may be applied to surrounding tissue in one, two, or more directions to manipulate endogenous or exogenous stress at the skin site in one, two or more directions. According to variations, devices and methods described herein may reduce or otherwise manipulate the stress experienced by skin and/or a wound and surrounding tissues in order to treat a subject. The devices may also assist in preventing or reducing the incidence of wound dehiscence.

According to the devices, kits and methods described herein, a skin treatment device, skin device, wound treatment device, scar or keloid treatment device, scar or keloid amelioration or prevention device, bandage, or dressing may be provided that may be applied, attached to or coupled to one or more layers of the skin or tissue of a subject (hereinafter referred to as "dressing", "skin device" or "skin treatment device").

In addition to amelioration of scar formation, other uses for such skin treatment device may or may not include without limitation, for example, treating skin related conditions such as acne, blemishes, rosacea, warts, rashes (including but not limited to erythematous, macular, papular and/or bullous conditions), psoriasis, skin irritation/sensitivity, allodynia, telangiectasia, port wine stains and other arteriovenous malformations, and ectopic dermatitis; treating or improving existing scars, wrinkles, stretch marks, loose or sagging skin or other skin irregularities; lifting, pinning, holding, moving skin for various purposes such as during pre-operative preparation, during surgical procedures for example as a low-profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, aesthetic skin treatment or resurfacing whether topical or subdermal, whether or not using an energy modality such as, for example, microwave, radio-frequency ablation, high-intensity focused ultrasound, laser, infrared, incoherent light, thermal (heat and/or cold, ablative or non-ablative), use of vacuum or suction, vibration or massage (e.g. ENDERMOLOGIE®, LPG Systems, France), during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may include use of a drug or other therapeutic agent that may be applied to the skin with such device. The agents may include but are not limited to antibiotics, anti-fungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face (e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes. Such devices may also be referred to herein as a "dressing", "skin device" or "skin treatment device".

The devices, kits or methods described herein may include a packaging, carrier, support, base, applicator, handles, manipulation elements e.g. for mechanical application of force, and/or tensioning device, each of which may: contain, hold, carry or support a dressing at least temporarily; may be used to prepare a dressing for application; may be used to exert a tensioning, straining and/or stretching force to a dressing, e.g., prior to application to a subject; may be used to deliver, orient or apply a dressing; may be used to maintain a dressing in a stressed or strained configuration; may be used to stress or strain a dressing; may be used to separate the dressing from the packaging, carrier, support, base, applicator or tensioning device and/or may be used during or after application of a dressing to provide additional treatment to a wound, incision or other treatment location; and/or may be used to apply pressure to a wound, incision or other treatment location. According to some variations, a packaging, manipulation elements, backing support and/or applicator may provide structural support for a dressing while or after an adhesive liner is released. According to some variations, an assembly may be constructed to avoid folding or bending of the dressing to the extent that the adhesive on the dressing sticks to itself. For example, when some variations of the dressing are held or supported at one point or along one edge of the dressing in a cantilever configuration, the dressings will not bow, laterally deform, or otherwise deform out of plane, under their own mass or configuration.

In some other variations of the devices and methods herein, a device with a substantially rigid support structure or that provides structural support to a dressing and that provides a particular resistance to bending or column strength when two opposing edges of the device and support structure are placed under a compressive load that causes axial compression or lateral deformation, e.g. a force similar to a hand grasping force is applied to an edge of the device, before the device buckles or folds. For example, a resistance to bending may be characterized as the peak force that is achieve as the device and support structure are compressed without compressed by 25% of its original dimension. This column strength or rigidity may vary, depending upon the direction along the device and support structure being measured. In some further variations, the peak force may be at least about 0.02 Newtons per millimeter (N/mm), about 0.03 N/mm, about 0.05 N/mm, about 0.1 N/mm, about 0.15 N/mm, about 0.2 N/mm, about 0.3 N/mm, about 0.4 N/mm or about 0.5 N/mm. In some variations of devices comprising generally flat or planar devices and support structures having a thickness, the peak force may be measured by applying a compressive force along the shortest dimension of the device/support structure that is transverse to the thickness of the device/support structure. According to such variations, the device may have an aspect ratio of length to width that is greater than 1:1, 2:1 or 3:1, for example.

A resistance to bending in the direction of dressing strain may also be measured by three-point bending, applying a transverse force to the midpoint of the applicator simply supported on two outer points at a given distance apart or support span. For example, the distance between the two points of a sample may be approximately 0.75 inches and a force that ranges from about 1 to 1.25 pounds may be applied to a sample approximately 0.35 inches in width resulting in a deflection of approximately 0.05 inches. A resistance to bending may also be measured by characterizing the force at which buckling occurs on a simply supported beam. For example, a force of approximately 0.45 pounds may be applied to a simply supported sample approximately 0.35 inches in width and may result in a deflection of approximately 0.004 inches. The resistance to bending may also be characterized by the strain of the outer surface before fracture or permanent deformation. By taking measurements of the support structure and the deflections during the test procedure, a load deflection curve may be generated and the flexural modulus of the support structure may also be calculated. In some variations, the support structure may comprise a flexural modulus of at least about 0.9 GPa, while in other embodiments, the flexural modulus is at least about 1 GPa, at least about 1.1 GPa, at least about 1.2 GPa, at least about 1.3 GPa, or at least about 1.4 GPa.

In another example, a device of 7 cm wide by 19 cm long may be configured with a support structure comprising a paperboard, support sheet or support structure. The support structure may have an average thickness in the range of about 0.008" to about 0.028" or greater. In some specific variations, the support structure may have a thickness of about 0.012", about 0.016", about 0.018", about 0.024", about 0.28" or about 0.032", about 0.036", about 0.04", about 0.05" or greater. Upon the application of force along the lengthwise edge of the 19 centimeter length, i.e. across the 7 cm width of the device, the support structure may provide sufficient rigidity or column strength to achieve peak forces of about 3 pound or more, 4 pounds or more, or about 10 pounds or more, while being compressed, collapsed, bowed, buckled or otherwise deformed by 25% along its 7 cm width (i.e. about 1.75 cm). In some variations, the support structure may comprise scoring or regions of reduced thickness to permit some bending it at least one direction or in both directions.

According to some variations, a device that provides structural support may have a plurality or supporting cross elements or segments extending from one edge of the length to an opposing edge or the length (or from one edge of a width to an opposing edge of a width); According to some variations there may be three or more cross elements, e.g., a cross element extending along two opposing edges and transversely across a width (or a length) and one or more cross elements extending across the width (or length) and between the cross elements along the two opposing edges. Such cross elements may or may not be coupled or connected to each other, for example, with a relatively flexible material. Such cross elements may have a total aggregate width with respect to the length of an opposing edge of about 20% or more, about 25% or more, about 30% or more, or about 35% or more. According to some variations, one or more cross elements may be provided that have a total aggregate width, relative to the length of the opposing side, between about 20% to 100%. Such cross elements may be segmented and may provide flexibility when bending in a direction and rigidity relative to the flexibility, in another direction.

One or more devices or variations may also provide structural support or stability of the dressing as it is oriented and/or applied to the skin of a subject. According to some variations, the dressing and packaging is configured to be pre-oriented in a position facing a wound before or after the wound device is prepared for application, e.g., the adhesive liner is removed. According to some variations, a packaging or applicator is configured to be used with one hand to orient and/or apply the device to the skin of a subject. For example, in some situations, particularly where a longer or larger dressing is used, a packaging or applicator provides structural support for a dressing such that a user can effectively hold onto, manipulate and/or apply a prepared dressing with one-hand. According to some variations, the assembly may comprise a support structure. A dressing support structure is defined herein to mean a structure that is coupled whether directly or indirectly, to a back surface of a dressing that is to be applied to a subject. The support structure may further comprise at least in part, a material or structure that is more rigid than the dressing to be applied to a subject. The support structure may comprise one or more elements or segments. It may be constructed of a single substrate, a laminate or a plurality of elements coupled together and/or to the dressing. According to some variations at least 20%, 25%, 30%, 35%, or 40% of a length or width of the dressing is supported by one or more support structures extending from a first opposing side to an opposite side along a length or width of the dressing. In some further variations, the percentage of a length or width that is supported by the support structure(s) is a minimum average of support across the entire length or entire width of the device, e.g. at least a 20%, 25%, 30%, 35% or 40% average support across an entire dimension of the device, e.g. length or width. According to some variations, an entire area of a dressing is supported by a support structure. According to some variations, a base, carrier or support of a dressing may comprise at least three support structures extending transversely between opposing sides of the dressing. According to some variations, a support structure comprises interconnected members or elements.

According to some variations, a base, carrier or support remains coupled to the dressing as it is applied. According to some variations, greater structural support is provided to a dressing carrier, support or base in a first direction while greater flexibility is provided in a second direction, while lesser flexibility is in the first direction and lesser structural support is provided in the second direction. According to some variations, one or more support structures may extend beyond an edge of the first opposing side. According to some variations, one or more support structures, at least in part, may extend beyond at least a portion of an edge of a first opposing side and at least in part beyond at least a portion of an edge of an opposite side. According to some variations, a support structure may extend at least 3 mm from at least a portion of an edge of the dressing. According to some variations, the packaging or applicator is configured to improve a sterile transfer of a dressing to a wound of a subject. According to variations, the packaging or applicator may be sufficiently wider or longer, or have a sufficiently larger area than a dressing providing the ability to maneuver or manipulate the support or applicator so that it provides sterile application and/or one-handed application without the need to touch the dressing. According to some variations, a margin of distance is provided from the outer edges of the dressing carrier, support or base to the dressing supported on the base or adhesive on the dressing. Such margins may be selected to prevent or resist a user from touching the dressing or dressing adhesive when grasping the edges to manipulate the dressing carrier, support, applicator or base.

Devices, kits and methods described herein may be for the treatment, amelioration, or prevention of scars and/or keloids by creating and/or maintaining a pre-determined strain in an elastic skin treatment device that is then affixed to the skin surface using skin adhesives to transfer a generally planar (e.g. compressive) force from the bandage to the skin surface. Other uses include wound closure and skin splinting/stabilization treatments.

In some variations, a dressing is provided, comprising an elastic sheet structure (e.g., a comprising a silicone polyurethane, TPE (thermoplastic elastomers), synthetic rubber or co-polyester material) comprising an upper surface, a lower surface, a first edge and a second edge opposite the first edge, and one or more adhesive regions. The dressing may further comprise a first release liner releasably attached to the adhesive region or regions. The adhesive region(s) may comprise a pressure sensitive adhesive. The dressing may be tapered or otherwise shaped to reduce skin tension at the edges. The dressing may have modified, reduced or no adhesive near its edges to reduce skin tension at the edges. Portions of the dressing may be unstrained and may thereby reduce strain in certain areas of the skin where the dressing is applied. In some specific examples, the unstrained area or areas are found between the edges of the dressing and the strained area(s). In some further examples, the unstrained areas are limited to this area and are not found, during application or use, between the strained areas of a single dressing, in use. In still further examples, the unstrained areas are limited to areas along the edges of a dressing that intersect the strain axis of the strained area(s), but not to areas along the edges of the dressing that are generally parallel to the strain axis.

A device may be used to strain and/or maintain a strain on a dressing. The device may further comprise a releasable locking mechanism, attachment mechanism or adhesive, configured to maintain the member or mechanism in a strained configuration.

According to some variations, the packaging is also sufficiently flexible in at least one direction to permit curving or shaping of the dressing to conform to the curvature or shape of the location on the body or skin where the dressing is applied. Generally, the flexibility of the packaging used to conform the dressing to the treatment site may be configured so that the treatment site is not substantially deformed during the application of the dressing; so that the application of the dressing is relatively smooth or uniform on the skin; and/or provides a uniform, predetermined, or relatively predictable strain or force to an area of skin The packaging or applicator may have flexibility in a first direction and greater rigidity in another direction. The packaging or applicator may include elements or segments that permit flexibility with respect to adjacent elements or segments.

According to some variations, the packaging is also sufficiently flexible in at least one direction to permit curving or shaping of the dressing to conform to the curvature or shape of the location on the body or skin where the dressing is applied. Generally, the flexibility of the packaging used to conform the dressing to the treatment site may be configured so that the treatment site is not substantially deformed during the application of the dressing; and/or so that the application of the dressing is relatively smooth or uniform on the skin; and/or provides a uniform, predetermined, or relatively predictable strain and/or force to an area of skin. The packaging or applicator may have flexibility in a first direction and greater rigidity in a second direction. The first direction may be transverse to the direction of straining or have a component that is transverse to the direction of straining. The second direction may by the direction of straining or have a component that is in the direction of straining. The first direction may or may not be transverse with respect to the second direction. The packaging or applicator may include elements or segments that permit flexibility with respect to adjacent elements or segments.

According to some variations a desired flexibility, for example having at least one component transverse to the direction of straining, may be characterized by a modified cantilevered beam bending model, i.e. applying a force to the free end of a beam, simply supported from the other end, while wrapping it around a cylindrical object with a known radius of curvature or curvature, defined as the reciprocal of the radius of the curvature. According to one variation, the force to bend the packaging or applicator around an object with a predetermined curvature may be no greater than about 3 pounds. According to one variation, the force may be no greater than about 0.3 pounds. According to one variation, the force to bend around a predetermined curvature of about a 2.5 inch radius may be no greater than about 3 pounds. In another variation, the force to bend around a predetermined curvature of about a 2.5 inch radius may be no greater than about 0.3 pounds.

In one variation, a skin treatment system is provided, comprising an elastic planar structure with a load per millimeter width of at least 0.1 Newtons at a strain of at least 0.4, and a strain limiter coupled to the elastic planar structure and configured to resist straining of the elastic planar structure beyond a predetermined strain. The strain limiter may comprise a first handle at a first end of the at least one strain limiter, and a second handle at a second end of the at least one strain limiter. The skin treatment system may comprise at least two elongate strain limiting structures. The first handle may be contiguously or non-contiguously coupled to the elastic planar structure between the first ends of the at least two elongate strain limiting structures. The second handle may also be contiguously or non-contiguously coupled to the elastic planar structure between the second ends of the at least two elongate strain limiting structures. The predetermined strain may be at least 0.2 or 0.4. The strain limiter may be releasably coupled to the elastic planar structure. The strain limiter may be adhered to the elastic planar structure using an adhesive. The adhesive may comprise a shear-resistance to a force level that is greater than the T-peel resistance to the force level. The first handle and the second handle may comprise a substantially inelastic material relative to the elastic planar structure, which may optionally be a semi-rigid or rigid material. The strain limiter may comprise at least one flexible, inelastic elongate element. The elastic planar structure may comprise an unstrained configuration in which a distance between a first attachment region of the strain limiter and a second attachment region of the strain limiter is less than a length of the strain limiter between the first attachment region and the second attachment region, and may comprise a strained configuration at the predetermined strain wherein the distance between the first attachment region of the strain limiter and a second attachment region of the strain limiter is substantially equal to the a length of the strain limiter between the first attachment region and the second attachment region. The strain limiter may comprise a folded board with at least three two folds, or a ratchet and pawl mechanism. The strain limiter may be selectively configured to resist straining of the elastic planar structure beyond a plurality of predetermined strains. The plurality of predetermined strains may comprise graphical indicia on the strain limiter.

In another variation, the skin treatment system comprises an elastic planar structure, comprising a tensioning axis, and a strain limiter coupled to the elastic planar structure and configured to resist straining of the elastic planar structure beyond a predetermined strain, wherein the attachment of a first end of the strain limiter to the elastic planar structure is contiguous across a dimension of the elastic planar structure transverse to the tensioning axis. The elastic planar structure may have a load per millimeter width of at least 0.1 Newtons at a strain of at least 0.4. The strain limiter may comprise a first handle at a first end of the at least one strain limiter, and a second handle at a second end of the at least one strain limiter. The skin treatment system may comprise at least two elongate strain limiting structures. The first handle may be contiguously coupled to the elastic planar structure between the first ends of the at least two elongate strain limiting structures. The second handle may also be contiguously coupled to the elastic planar structure between the second ends of the at least two elongate strain limiting structures. The predetermined strain may be at least 0.2 or 0.4. The strain limiter may be releasably coupled to the elastic planar structure. The strain limiter may be adhered to the elastic planar structure using an adhesive. The adhesive may comprise a shear-resistance to a force level that is greater than the T-peel resistance to the force level. The first handle and the second handle may comprise a substantially inelastic material relative to the elastic planar structure, which may optionally be a semi-rigid or rigid material. The strain limiter may comprise at least one flexible, inelastic elongate element. The elastic planar structure may comprise an unstrained configuration in which a distance between a first attachment region of the strain limiter and a second attachment region of the strain limiter is less than a length of the strain limiter between the first attachment region and the second attachment region, and may comprise a strained configuration at the predetermined strain wherein the distance between the first attachment region of the strain limiter and a second attachment region of the strain limiter is substantially equal to the a length of the strain limiter between the first attachment region and the second attachment region. The strain limiter may comprise a folded board with at least three two folds, or a ratchet and pawl mechanism. The strain limiter may be selectively configured to resist straining of the elastic planar structure beyond a plurality of predetermined strains. The plurality of predetermined strains may comprise graphical indicia on the strain limiter.

In another variation, a skin treatment system is provided, comprising an elastic structure, first and second handles attached to opposite regions of the elastic structure, wherein the first and second handles are coupled to the elastic structure and configured to provide a substantially uniform tensile force across the elastic structure; and a strain indicator. The strain indicator may comprises graphical or numerical indicia of the degree of strain.

BRIEF DESCRIPTION OF THE DRAWINGS

FIG. 2A is a top perspective view of a skin treatment device in a first configuration.

FIG. 2C is a side elevational view of the skin treatment device in FIG. 2A.

DETAILED DESCRIPTION

Figure 1A:
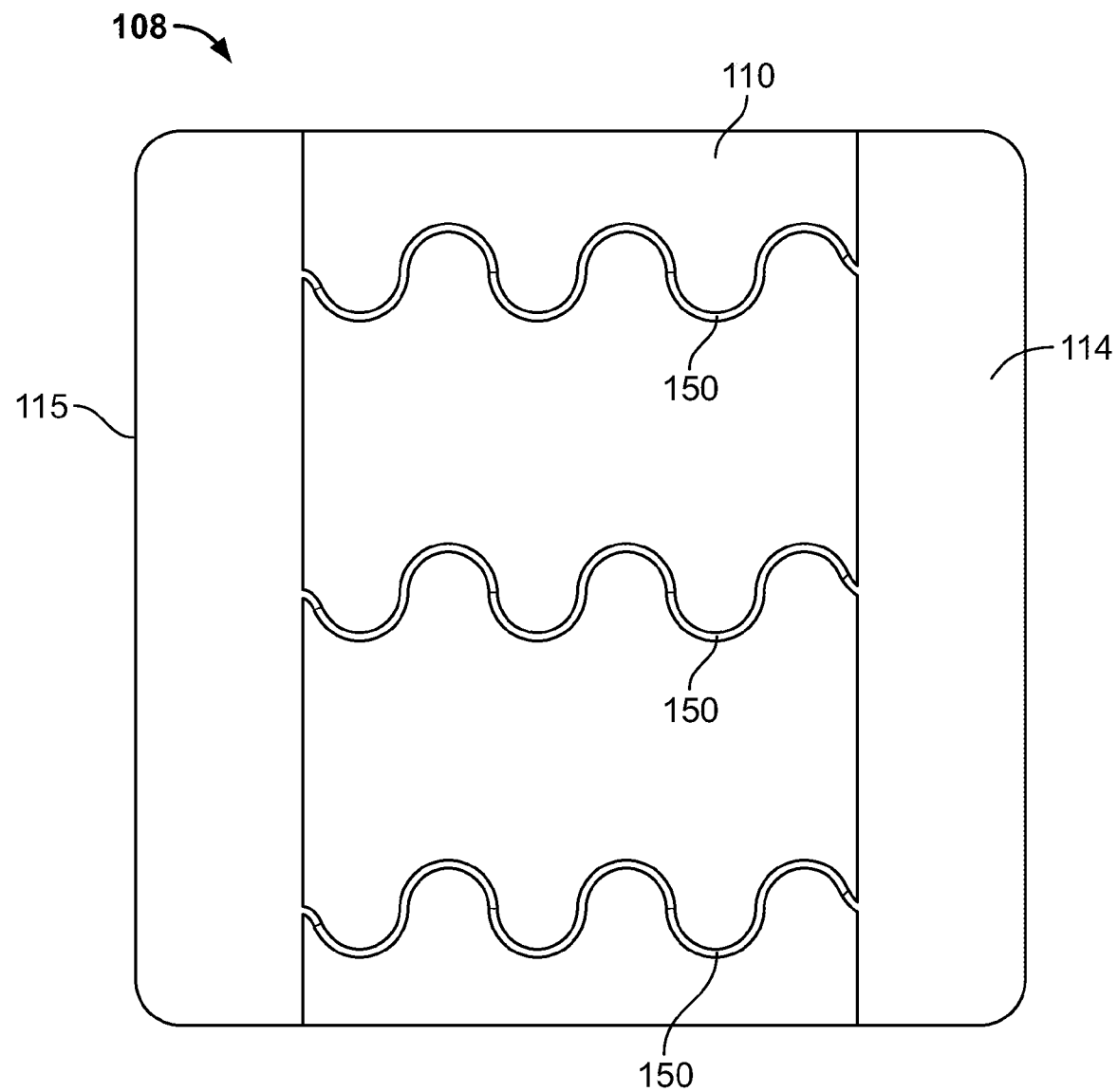
FIG. 1A is a top view of a skin treatment device in a first configuration.

It is believed that controlling, managing or modulating stresses acting in and/or on skin ("mechanomodulation") may have beneficial effects. Modulation of mechanical stresses or effects acting in and/or on skin may translate into or induce biomechanical response, including but not limited to, responses relating to scarring, scar proliferation or other effects.

Devices, methods, systems and kits described herein may relate to devices used to shield skin or a wound from its mechanical environment. The term "shield" is meant to encompass the unloading of stress experienced by the skin or wound as well as and/or providing a physical barrier against contact, contaminants, and the like. The stress shielding or force offloading devices and methods described here may shield the skin or a wound by unloading endogenous stress and/or exogenous stresses. In some variations, the devices may shield the skin from endogenous stress without affecting exogenous stress on the skin, e.g., devices that modify the elastic properties of the skin, etc. In other variations, the devices may shield the wound from exogenous stress without affecting endogenous stress on the skin wound. In still other variations, the devices shield the skin from both endogenous and exogenous stress.

Devices, kits and methods described herein may treat skin at a skin site ("skin treatment device"), including without limitation, to ameliorate the formation of scars at wound sites by controllably stressing or straining the epidermis and deeper layers of dermal tissue at or near a skin site, i.e., at or adjacent a wound or treatment site of a subject's skin, thereby reducing tensile or compressive stress at the skin site. The stress at the skin site may be reduced to levels below that experienced by normal skin and tissue. The stress or strain may be applied to surrounding tissue in one, two, or more directions to reduce endogenous or exogenous stress at the skin site in one, two or more directions. Thus, devices and methods described herein may reduce the stress experienced by skin and/or a wound and surrounding tissues in order to treat a subject. The device may also assist in preventing or reducing the incidence of wound dehiscence.

"Dressing" or "Skin Device" as used herein may include but is not limited to, a skin treatment device, wound treatment device, scar or keloid treatment device, scar or keloid amelioration or prevention device, bandage, or dressing, that may be applied, attached to or coupled to one or more layers of the skin or tissue of a subject.

Devices kits and methods described herein may be for the preparation and/or application of a dressing. Such preparation may include but is not limited to, for example, removal of an adhesive liner, straining or tensioning a dressing, orienting a dressing for application and/or applying a medicament or other material to a portion of the dressing prior to application.

According to some variations, the packaging, tensioning device, dressing carrier, support, base, handles, manipulation elements and/or applicator may further comprise an opening, a window, or a clear or semi-opaque portion through which a wound, incision or other location may be visualized as the dressing is applied to the skin. According to some variations, the window guides the application of a dressing so that there is an optimal or desired distance between the wound and the edges of the dressing and/or so that the dressing is in an optimal location for unloading skin stresses.

According to some variations, a packaging, manipulation element, and/or applicator is more rigid or provides sufficient column strength in at least a first direction to be supportive of a dressing, while being relatively more flexible and less rigid in at least second direction to provide for a more conforming application to a curved or shaped skin surface of a subject or to permit curvature or shaping of the dressing where it is applied. The first and second directions may or may not be orthogonal to each other. According to some variations, a packaging applicator, tensioning device or dressing carrier, support or base is sufficiently rigid or supportive of a dressing while permitting shaping of the dressing. According to some variations, the carrier or support which may include a base and/or a cover may comprise segments of relatively more rigid material flexibly coupled to adjacent segments to provide flexibility to permit shaping of packaging/applicator and/or dressing while providing sufficient support of the dressing during application. According to some variations, segments are coupled to adjacent segments by way of a flexible material, such as a low-density polyethylene (LDPE) material, or a composite of adhesive and a thinner more flexible substrate. Alternatively, segments may be formed as a structure by manufacturing a substrate with cut-outs, slots, grooves, scoring or other openings or variations in thickness of the substrate at different locations.

The packaging, applicator, manipulation elements tensioning device, or dressing carrier may have elements or features the provide flexibility in one direction while limiting flexibility in another direction. Each of the elements may permit flexing in a different direction than one or more of the other elements. Flexible elements may be straight, or shaped according to a desired application or location of placement. According to some variations, the flexible elements may limit flexibility when the device is being strained and permit flexibility when the device is being applied to the skin.

According to variations, flexible elements are provided in combination with support elements that provide sufficient support to allow a user to maintain the dressing in a strained configuration. According to variations, one or more elements may be provided to maintain a strained dressing in a strained configuration, for example a securing element that secures the dressing in a strained configuration until it is applied to a subject and is released from the carrier, support, base, manipulation element, tensioning device or applicator. For example, after straining the dressing, the dressing may be adhered or attached to one or more elements of a dressing, support, base, manipulation elements, tensioning device or applicator or dressing assembly until it is released from the carrier, support, base tensioning device or applicator or assembly.

According to some variations, the applicator may be further used to help reduce bleeding, e.g., by allowing application of a compressive force using a support structure while or after the device is applied. One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antifibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other active agents that may be useful in aiding in some aspect of the wound healing process. For example, the active agent may be a pharmaceutical compound, a protein (e.g., a growth factor), a vitamin (e.g., vitamin E), or combinations thereof. A further example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin. Of course, the devices may comprise more than one medicament or agent, and the devices may deliver one or more medicaments or agents.

The dressing may comprise an elastic member, such as a sheet of elastic material. The elastic material of the dressing may comprise a single layer of material or multiple layers of the same or different materials. The material may have any of a variety of configurations, including a solid, foam, lattice, or woven configuration. The elastic material may be a biocompatible polymer, e.g., silicone, polyurethane, TPE (thermoplastic elastomers), synthetic rubber or co-polyester material. The thickness of polymer sheets may be selected to provide the dressings with sufficient load carrying capacity to achieve desired recoverable strains, and to prevent undesired amounts of creep deformation of the dressings over time. In some variations, the thickness across dressings is not uniform, e.g., the thickness across the dressing may be varied to change the stiffness, the load carrying capacity, or recovery strains in selected orientations and/or locations. The elastic material of the exemplary dressing may have a thickness in the range of about 50 microns to 1 mm or more, about 100 microns to about 500 microns, about 120 microns to about 300 microns, or in some variations about 200 microns to about 260 microns. The exemplary dressings have an edge thickness of about 500 microns or less, 400 microns or less, or about 300 microns or less may exhibit less risk of skin separation from inadvertent lifting when inadvertently brushed against clothing or objects. In some variations, the dressings are tapered near the edges to reduce thickness. A tapered edge may also ameliorate peak tensile forces acting on skin tissue adjacent to the adhesive edges of the dressing. This may or may not reduce the risk of skin blistering or other tension-related skin trauma. In other variations, the edges of the dressing may be thicker than the middle of the dressing. It is hypothesized that in some configurations, a thicker dressing edge may provide a relative inward shift of the location of the peak tensile forces acting near the dressing edge, compared to dressings of uniform thickness. The elastic material may have a load per width of at least 0.35 Newtons per mm at an engineering strain of 60% or a load per width of at least 0.25 Newtons per mm at an engineering strain of 45%. The elastic material may have a load per width of no greater than about 2 Newtons per mm at the engineering strain of about 45% to 60%, about 1 Newtons per mm at the engineering strain of about 45% to 60%, about 0.7 Newtons per mm at the engineering strain of about 45% to 60%, or no greater than about 0.5 Newtons per mm at the engineering strain of about 45% to 60%. The system elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of about 20% to 30% and attached to a surface. The elastic material may comprise an adhesive configured to maintain a substantially constant stress in the range of 200 kPa to about 400 kPa for at least 8 hours when strained to an engineering strain of about 20% to 30% and attached to a surface. The substantially constant stress may vary by less than 10% over at least 8 hours, or by less than 5% over at least 8 hours.

Although the depicted dressings may have a generally rectangular configuration with a length and/or width of about 160 mm to about 60 mm, in other variations the dressing may have any of a variety of lengths and widths, and may comprise any of a variety of other shapes. Also, the corners of the dressing may be squared or rounded, for example. The lengths and/or widths of an exemplary dressing may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the dressing (e.g. its length) to an orthogonal dimension to the maximum dimension (e.g. width), excluding the minimum dimension of the dressing (e.g. the thickness), may be in the range of about 1:3, about 1:2, about 1:1, about 2:1, about 3:1, about 4:1 about 5:1, about 6:1, about 7:1, about 8:1, about 9:1 or about 10:1 or greater. In some variations, the strain axis of the dressing in use may be oriented with respect to the maximum dimension or to the orthogonal dimension to the maximum dimension. In some variations, the final compressive stress and strain imposed onto the skin by the elastic material may be the result of the dynamic equilibrium between the tensile stress in the skin and the elastic material of the dressing. The skin at the skin site typically comprises an inherent tension that stretches incision site, whether or not any tissue was excised from the skin site. The elastic material and the adhesive region may be configured to be applied to a skin location so that when the dressing is stretched to a particular tension and then adhered to the incision site, tensile stress in the dressing is transferred to the incision site to compress the tissue directly under the dressing along a tangential axis to the skin surface, the stress and strain imposed onto the skin location has a net or resultant orientation or axis is also generally tangential or planar to the elastic material and/or the outer surface of the skin location, with a similar axis to the orientation or axis of the tensile stress in the dressing. The tension in the dressing will relax to a tension level that maintains equilibrium with increased tension in the skin adjacent to the dressing. The application of the dressing to the skin location may involve the placement of the dressing without overlapping or being wrapped onto itself, e.g. wherein only adjacent regions of the dressing are interconnected and wherein non-adjacent regions of the dressing are not interconnected. The actual amount of stress and strain imposed on the skin may vary, depending upon the particular person, skin location, the thickness or various mechanical characteristics of the skin layers (e.g. epidermis, dermis, or underlying connective tissues), and/or the degree of pre-existing scarring, for example. In some further variations, the wound treatment dressing may be selected or configured for use at a specific body location, such as the scalp, forehead, cheek, neck, upper back, lower back, abdominal region, upper torso (including but not limited to the breast folds), shoulder, upper arm, lower arm, palm regions, the dorsum of the hand, finger, thigh, lower leg, the dorsum or plantar surface of the foot, and/or toe. Where applicable, some body regions may be further delineated into anterior, posterior, medial, lateral, proximal and/or distal regions, e.g. the arms and legs.

The dressing may be configured to impose a skin strain in the range of about 10% to about 60% or more, in other configurations about 15% to about 50%, and in still other configurations, about 20% to about 30% or about 40%; the dressing may also be configured to impose a strain of less than 10%. To achieve the desired degree of skin strain, the dressing may be configured to undergo elastic tensile strain in the range of about 20% to about 80% or more, sometimes about 30% to about 60%, and other times about 40% to about 50% or about 60%. The dressing may comprise any of a variety of elastic materials, including but not limited to silicones, styrenic block copolymers, natural rubbers, fluoroelastomers, perfluoroelastomers, polyether block amides, thermoplastic elastomers, thermoplastic polyurethane, polyisoprene, polybutadiene, and the like. The material of the exemplary dressing may have a Shore A durometer in the range of about 20 to about 90, about 30 to about 80, about 50 to about 80. The exemplary dressing was constructed of MED 82-5010-05 by NUSIL TECHNOLOGY LLC (Carpinteria, Calif.). Other examples of suitable materials are described in U.S. application Ser. No. 11/888,978, which was previously incorporated by reference in its entirety.

When the dressing is applied to a skin location and allowed to at least partially recover to its base configuration, the recovery level or equilibrium level of strain in the dressing may be in the range of about 4% to about 60% or more, in other configurations about 15% to about 50%, and in still other configurations, about 20% to about 30% or about 40%. The ratio between the initial engineering tensile strain placed onto the dressing before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 45% engineering strain that is converted to a true strain).

In some further variations, one or more characteristics of the elastic material may correspond to various features on the stress/strain curve of the material. For example, the engineering and true stress/strain curves for one specific example of the dressing comprises a material that exhibits an engineering stress of about 1.2 MPa at about 60% engineering strain, but in other examples, the engineering stress may be in the range of about 900 KPa to about 3.5 MPa, about 1 MPa to about 2.2 MPa, about 1 MPa to about 2 MPa, about 1.1 MPa to about 1.8 MPa, about 1.1 MPa to about 1.5 MPa, about 1.2 MPa to about 1.4 MPa. When unloading or relieving stress from the dressing, the material may be configured with an engineering stress of about 380 KPa at about 40% engineering strain, but in other examples, the engineering stress during unloading of the material to about a 40% strain may be in the range of about 300 KPa to about 700 KPa, about 325 KPa to about 600 KPa, about 350 KPa to about 500 KPa, or about 375 KPA to about 425 KPa. When unloading the material to an engineering strain of about 30%, the material exhibits an engineering stress of about 300 KPa, but in other examples, the engineering stress when unloading the material to about 30% strain may be in the range of about 250 KPa to about 500 KPa, about 275 KPa to about 450 KPa, about 300 KPa to about 400 KPa, or about 325 KPA to about 375 KPa. When unloading to an engineering strain of about 20%, the material may have an engineering stress of about 100 KPa, but in other examples, the unloading engineering stress at about 20% may be in the range of about 50 KPa to about 200 KPa, about 75 KPa to about 150 KPa, or about 100 KPa to about 125 KPa. In some examples, the material may be configured to at least achieve a specific range or level of engineering stress at each of the specified engineering strain levels described above, but in other examples, the material may be configured for lower levels of maximum engineering strain, e.g. up to about 30% or about 40%.

In some examples, certain portions of the stress/strain curve may have a particular morphology. For example, for a particular level of maximum strain the loading curve may be generally linear on the corresponding true stress/strain curve. In an example using a dressing described herein, up to a true strain of about 45%, the loading curve had a generally linear configuration. In other examples, the configuration may only be linear along a portion of the loading curve or may be curved along the entire loading curve. Where the loading curve is non-linear, the loading curve may be convex, concave or both. Also, in some examples, the tangent line of the loading curve (i.e. the line between the two triangles) may also be generally co-linear.

In some variations, the elastic material comprises a material having an elastic modulus E of at least about 1 MPa, about 1.5 MPa, about 2 MPa, about 2.5 MPa, about 3 MPa, about 3.5 MPa, about 4 MPa, about 5 MPa, about 6 MPa, about 7 MPa, about 8 MPa, about 9 MPa or at least about 10 MPa or greater. The material elastic modulus E may be no greater than about 10 MPa, about 9 MPa, about 8 MPA, about 7 MPa, about 6 MPa, or about 5 MPa, or about 4 MPa.

In addition to the absolute stress levels at certain strain levels described above, the material may also be characterized with respect to the ratio between a) the stress to achieve a particular strain during loading, and b) the stress at the same strain during unloading. For example, the material may have a ratio of at least 4:1 to about 3:2 at each of the 20%, 30% and 40% strain levels, but in other examples, the material may exhibit these ratios only at 20%, at 30%, or at 40% strain levels, or at both 20% and 30% but not 40%, or at both 30% and 40% but not 20%. In other examples, the ratio at one, some or all of the strain levels may be in the range of about 3:1 to about 2:1, or about 5:2 to about 2:1.

In some examples, the elastic material of the dressing may be configured under testing conditions to achieve a stable level of stress at a constant strain, e.g. the material exhibits a limited amount of stress relaxation over a particular period of time and at a particular level of strain. The period of time may be at least about 8 hours, about 12 hours, about 18 hours, about 24 hours, about 36 hours, about 48 hours, about 72 hours, about 4 days, about 5 days, about 6 days, or about a week or more. The level of strain may be about 10%, about 20%, about 30%, about 40%, about 50%, about 60%, about 70%, or about 80% or more. The stress of the exemplary dressing over various time curves may be configured to maintain an engineering stress of about 300 KPa at an engineering strain of about 30% without noticeable deviation over a period of about 1 hour, about 2 hours, about 3 hours, about 4 hours, about 5 hours, about 6 hours, about 7 hours, or about 8 hours or more. The stresses at 10% strain, 20% strain, and at 40% may be lower or higher.

In some variations, the elastic material or the dressing may be configured under testing conditions to maintain a particular minimum level of stress when held at a constant strain over a particular time period. In an example to assess the ability of a backing material to maintain a stress and strain on skin over time, engineering strains were measured while each backing material was tensile strained to 60% at a rate of 100 microns per second and held for 10 minutes, and then dropped to a strain of 30% at a rate of 100 microns per second and held for 9 hours. For example, the exemplary dressing is able to maintain an engineering stress level of about 350 KPa at an engineering strain of 30%. In some other examples, the minimum level of stress may be about 100 KPa, about 120 KPa, about 140 KPa, about 160 KPa, about 180 KPa, about 200 KPa, about 220 KPa, about 240 KPa, about 260 KPa, about 280 KPa, about 300 KPa, about 320 KPa, about 340 KPa, about 360 KPa, about 380 KPa, about 400 KPa, about 420 KPa, about 440 KPa, about 460 KPa, about 480 KPa, about 500 KPa, about 600 KPa, about 700 KPa, about 800 KPa, about 900 KPa or about 1000 KPa or greater. The level of constant strain may be different in other configuration, with a level of about 15%, about 20%, about 25%, about 30%, about 35%, about 40%, about 45%, about 50%, about 55%, about 60%, about 65%, about 70%, about 75%, or about 80%. The time period over which the dressing is able to maintain a stress level may be at least about 2000 seconds, about 3000 seconds, about 4000 seconds, about 5000 seconds, about 6000 seconds, about 7000 seconds, about 8000 seconds, about 9000 seconds, about 10000 seconds, about 20000 seconds, about 30000 seconds, about 40000 seconds, about 50000 seconds, about 60000 seconds, about 70000 seconds, about 24 hours, about 36 hours, about 48 hours, about 72 hours, about 4 days, about 5 days, about 6 days, about 7 days, about 10 days, about 2 weeks, about 1 month or more. In some variations, the dressing, the elastic material and/or the adhesive material is configured to exhibit less than about a 15% change in stress or strain level over the particular period when applied to a skin surface or test surface. In other examples, the degree of change may be about 12%, about 10%, about 8%, about 6%, about 5%, about 4%, about 3%, or about 2% or less. The stress or strain may be an engineering stress or strain, and/or a true stress or strain.

The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive. The pressure sensitive adhesive may be made from, e.g., polyacrylate-based, polyisobutylene-based, silicone-based pressure sensitive adhesives, synthetic rubber, acrylic, and polyisobutylene (PIB), hydrocolloid, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion (e.g. as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, incorporated in its entirety herein by reference.

Release liners may be provided over the skin adhesive and may be removed prior to stressing, straining, stretching and/or applying a dressing to a subject. The release liners may comprise any of a variety of materials, including both opaque and transparent materials. The release liners may comprise Mylar or paper, or any other material with reduced adhesion to the adhesive material(s) of the device. For example, for a silicone adhesive, a fluoropolymer-treated polyester film may be used, and for an acrylic pressure sensitive adhesive, a silicone treated polyester or Mylar film or silicone treated craft paper may be used. In variations where the device has multiple separate adhesive regions, separate release liners may be provided for each region, or some regions may be covered by the same release liner.

In some variations the assembly may comprise one or more mechanisms or elements configured to facilitate separation, release, removal or detachment of the dressing from the packaging, manipulation elements applicator or tensioning device, other attachment elements or other portions of the dressing assembly, or other elements of the devices. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of dressing from the applicator, packaging, other portions of the dressing assembly and/or attachment structures, features, elements or portions. They may be self-releasing latches or spring members. They may be actuated when a pressure member is applied to a skin treatment device prior to removing the applicator. They may be manually actuated.

Packaging devices, applicators, tensioning devices, and corresponding attachment features may be configured to provide multi-direction strain or additional strain in an orthogonal direction to a dressing.

The packaging device, manipulation elements, applicator, tensioning device and/or attachment structure profile may be straight, curved or otherwise varied. For example, the shape of the elements of a device may be configured to follow the shape of the area of the subject's body to which the skin treatment device is to be attached. A packaging device, manipulation elements, tensioning device, applicator or other elements thereof may be selected or configured to have a profile that has a desirable profile for a particular body location or profile where the skin treatment device is to be placed on a subject's skin. A packaging device, manipulation element, applicator, tensioning device or elements thereof may be selected or configured to closely match a portion of a subject's body profile. The packaging device, manipulation element, applicator or tensioning device and/or an element or segment thereof, may be curved, curvable, flexible, bendable, malleable, deformable, shapeable or movable to provide alternative shapes or profiles of an attached dressing. They may be relatively curved, curvable, flexible, malleable, bendable, deformable, shapeable or movable in at least one direction while being more rigid in another direction.

A variety of locking, latching, securing, attaching or detent mechanisms may be used to maintain the dressing, packaging, manipulation elements, applicator and/or tensioning device in a various configurations including but not limited to unstrained, partially strained, strained configurations. A variety of locking, latching or detent mechanisms may be used to maintain a dressing in a variety of configurations including unstrained, partially strained, strained. By locking the packaging, applicator, tensioning device manipulation elements or other elements coupled to the dressing, or dressing in a strained position, a predetermined strain of a given dressing may be achieved and maintained until released. The predetermined amount of strain may be a predetermined absolute percentage of strain or level of force that is independent of the shape and/or size of the treatment site.

According to a variation, a skin treatment device is provided that may be strained prior to application to the skin of a subject. According to variations, device or device elements may provide a variable strain to the skin treatment device.

According to variations, a skin treatment device may comprise one or more manipulation elements removably coupled to a dressing. Such variations may further comprise a strain limiter that limits or determined the amount of strain applied to a dressing. Such variations may also further comprise a strain indicator that indicates a desired strain level has been reached.

According to a variation, a plurality of strain indicators may be provided where each indicator indicates a different strain level or amount.

According to a variation, a skin treatment device is provided that may be strained by a user prior to application to the skin of a subject. According to a variation, skin treatment device may include strain indicator that indicates when the dressing has been stretched by the user to a desired degree.

According to a variation, a skin treatment device that may be strained by a user may include a strain limiter configured to prevent over straining of the device, or straining the device beyond a desired degree or amount.

According to a variation, the strain limiting elements may prevent straining in regions where straining or less strain is desired. The strain limited skin treatment devices may also be shaped to provide a graduated strain or varying strain through the strained device. The device may be stretched by hand or may otherwise be configured to be stretched with a tensioning device, for example a set forth in application Ser. Nos. 12/854,859 and 13/345,524 incorporated in their entirety herein by reference.

According to a variation, a skin treatment device comprises one or more relaxed threads, strings, wires or other elongate, elongatable, straightenable or stretchable members that straighten, lengthen and/or stretch to a desired amount, degree, and/or preset limit. For example, in one variation, the members may have an undulating shape when the skin treatment device is unstretched and a straight configuration when the skin treatment device is stretched to a desired degree. The members may have a sufficient tensile strength to prevent over-stretching of the skin treatment device. According to a variation the skin treatment device is constructed of multiple layers of an elastic material such as silicone with an adhesive between layers to which the members are attached initially in the relaxed, undulating, sinusoidal, unstraightened or other unstretched configuration. According to a variation, the shape limiting strings or other devices may prevent straining in regions where straining or less strain is desired. For example, the threads may be straight at the edges of the skin treatment device to prevent straining at the edges.+–

Figure 1B:
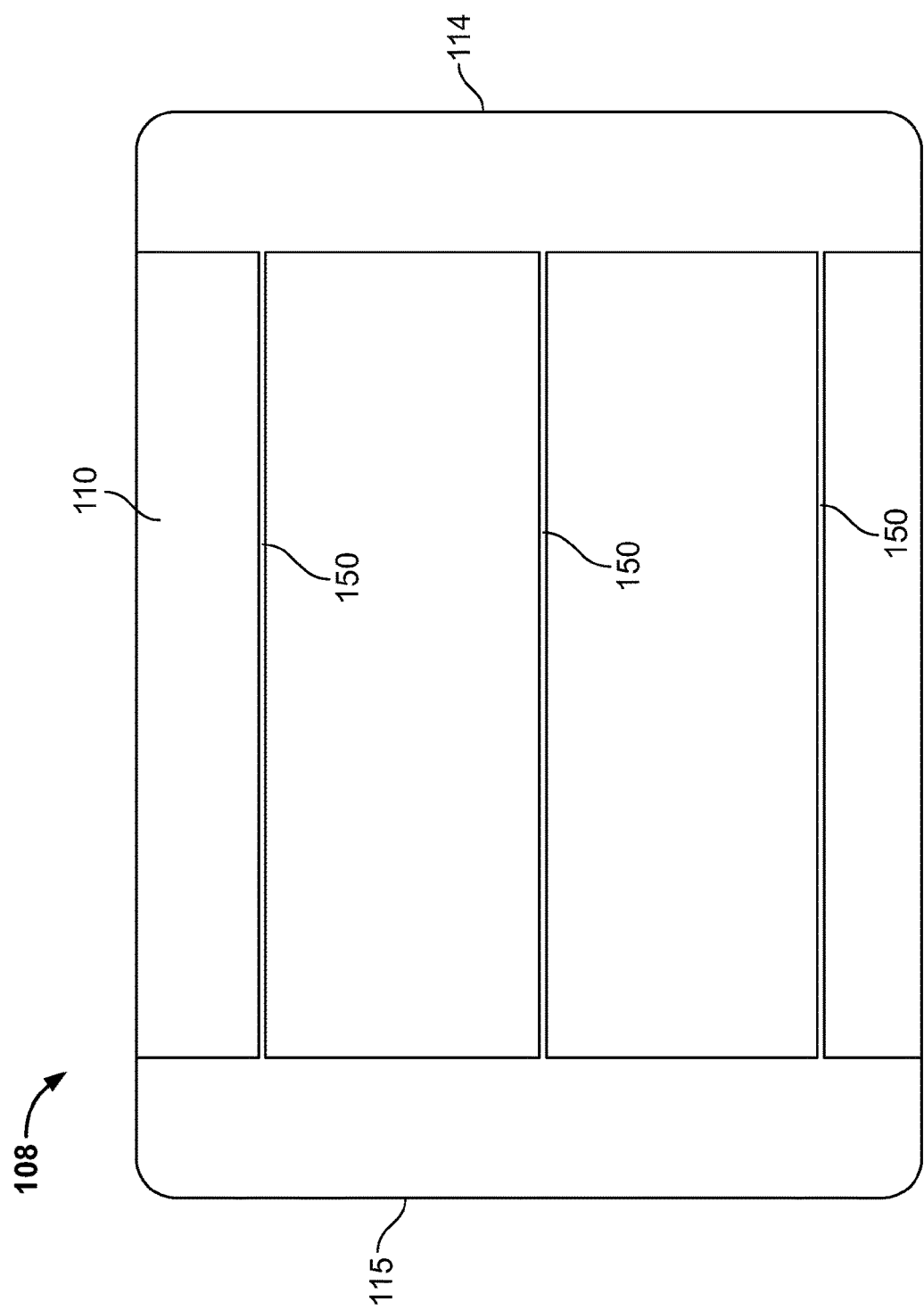
FIG. 1B is a top view of the skin treatment device of FIG. 1A in a second configuration.

FIGS. 1A and 1B illustrate a strainable skin treatment device 110 with strain indicators and/or strain limiters 150. The strain indicators and/or limiters 150 may be visibly positioned in or on a device assembly 108 which may comprise layers of elastic material sandwiching the strain indicators 150 therebetween. The material may or may not be transparent or translucent. Indicators may also be positioned on the surface of the device. The strain indicators and/or limiters 150 may be threads, wires or other elongate or elongatable members 155. In use, the device assembly 108 is grabbed by a user at opposing sides 114, 115 and stretched. The opposing sides 114, 115 may also have removable (or non-removable) manipulation elements attached to the ends to provide for a more even or uniform strain, and may comprise an inelastic material which is the same or different as the strain indicators/limiters 150. The manipulation elements may span the entire transverse dimension of the device 110 to the axis of tensioning, as depicted in FIG. 1B, but in other variations may be less than the entire transverse dimension (e.g. having a transverse dimension sufficient to span a plurality of strain indicators/limiters 150, but less than the full transverse dimension of the device 110). Such elements may comprise planar members, handle members, flexible members and/or inflexible members. They may be attached and removed in a variety of manners, for example as described herein. Also, although the example depicted in FIGS. 1A and 1B depict a plurality of strain indicators/limiters 150 that are equally spaced apart and have uniform lengths and uniform attachment points across a transverse dimension to the tensioning axis of the device 110, in other examples, the indicators/limiters 150 may have a variable or non-uniform spacing, may have non-uniform lengths, non-uniform attachment points, and may also be serially arranged along the tensioning axis.

As the skin treatment device 110 is stretched or strained, the device width increases and the members 155 straighten. When the skin treatment device 110 has been stretched or strained to a desired amount or a pre-determined or preset amount, the indicators and/or limiters 150 are in a visible or identifiably straightened configuration, for example as shown in FIG. 1B. The indicators and/or limiters 150 may also comprise a relatively inelastic material such as, e.g. a nylon string, that prevents or resist the skin treatment device 110 from over stretching or straining to a degree greater than is desirable, thus limiting the strain applied to the device 110. A skin adhesive with a protective liner may be applied to a side of the skin treatment device 110 prior to stretching, stressing or straining. The liner may be removed from the skin treatment device 110 prior to stretching. According to one aspect of the invention, it is believed that a range of strain is significant in providing treatment to a skin. According to variations other shapes or stretching indicators may be used where a visible change in an indicator line, shape or color may occur. Examples of a color change material or structure are described in U.S. Pub. No. 2006/0246802 to Hughes et al, which is herein incorporated by reference in its entirety.

Figure 2B:
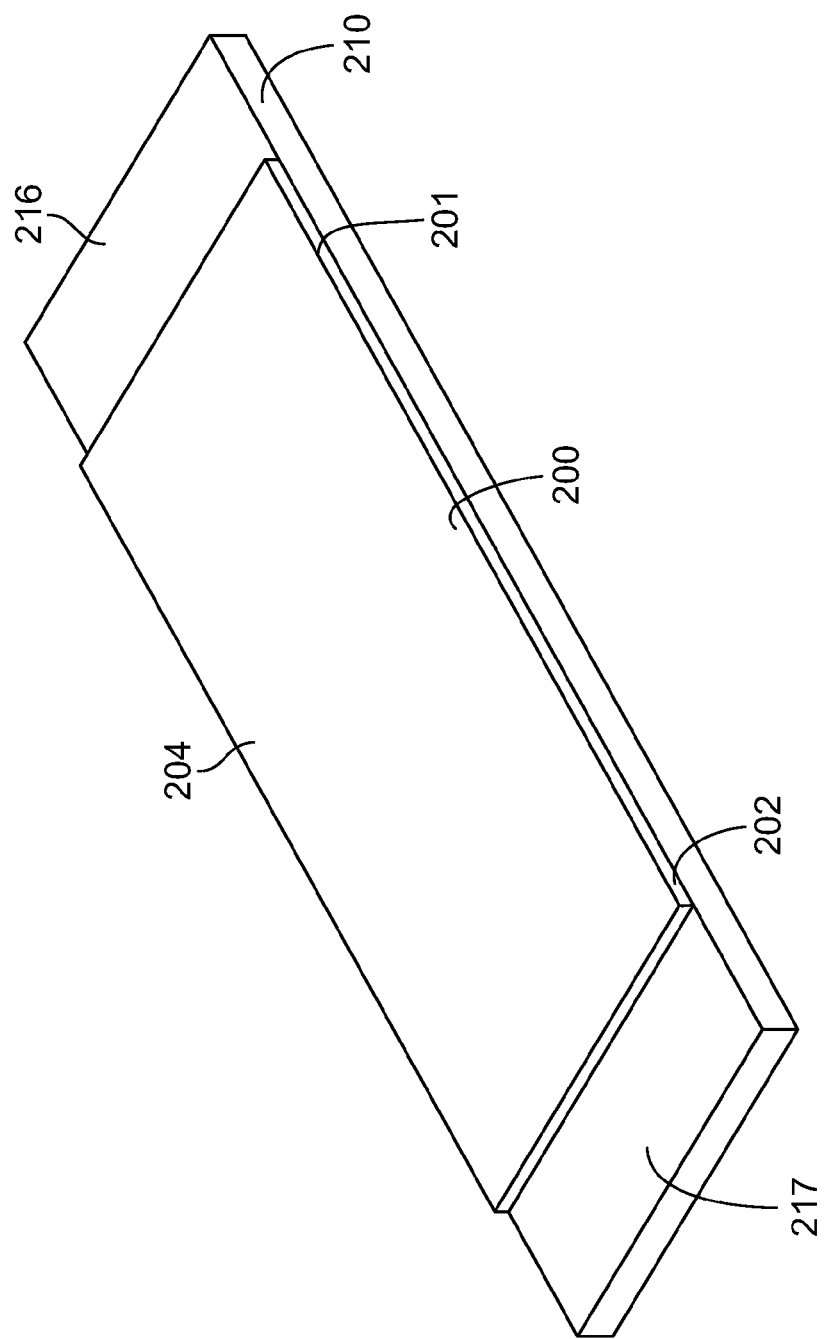
FIG. 2B is a top perspective view of a skin treatment device in a strained second configuration.

FIG. 2A to 2C illustrate a manually strainable skin treatment device 200 that may comprise, an elastic material. The skin treatment device 200 is coupled to a strain limiting backing 210 comprising a flexible inelastic or relatively less elastic material with respect to the elastic material of the skin treatment device 200, such as, for example, LDPE, FEP or nylon. As shown in FIG. 2A, prior to straining, the skin treatment device 200 is shown in a relaxed, folded configuration, coupled (e.g. with an adhesive such as a preferentially removable adhesive as compared to skin adhesive used on surface 204) at its opposing ends 201, 202 to the inner surface 214 of the strain limiting backing 210 at locations or areas 211,212. In the relaxed configuration the length of the device 200 is a first shorter length. The ends 216, 217 of the strain limiting backing 210 may extend outward of locations 211, 212 and be used as grips to pull and straighten the backing 210 as shown in FIG. 2A to thereby strain and increase the length of the device 200 to a second greater length. The inner surface 214 of the strain limiting backing may comprise an adhesive layer such as a preferentially removable adhesive as compared to skin adhesive used on surface 204 which may attach the back 203 of the device 200 to the inside surface 214 of the backing 210 when the device is strained. The exposed surface 204 of the device 200 may comprise a skin adhesive such as a pressure sensitive adhesive that secures the device to a skin surface when applied. After the device is applied to a skin surface, the backing 210 may be peeled away from the device 200.

Figure 3A:
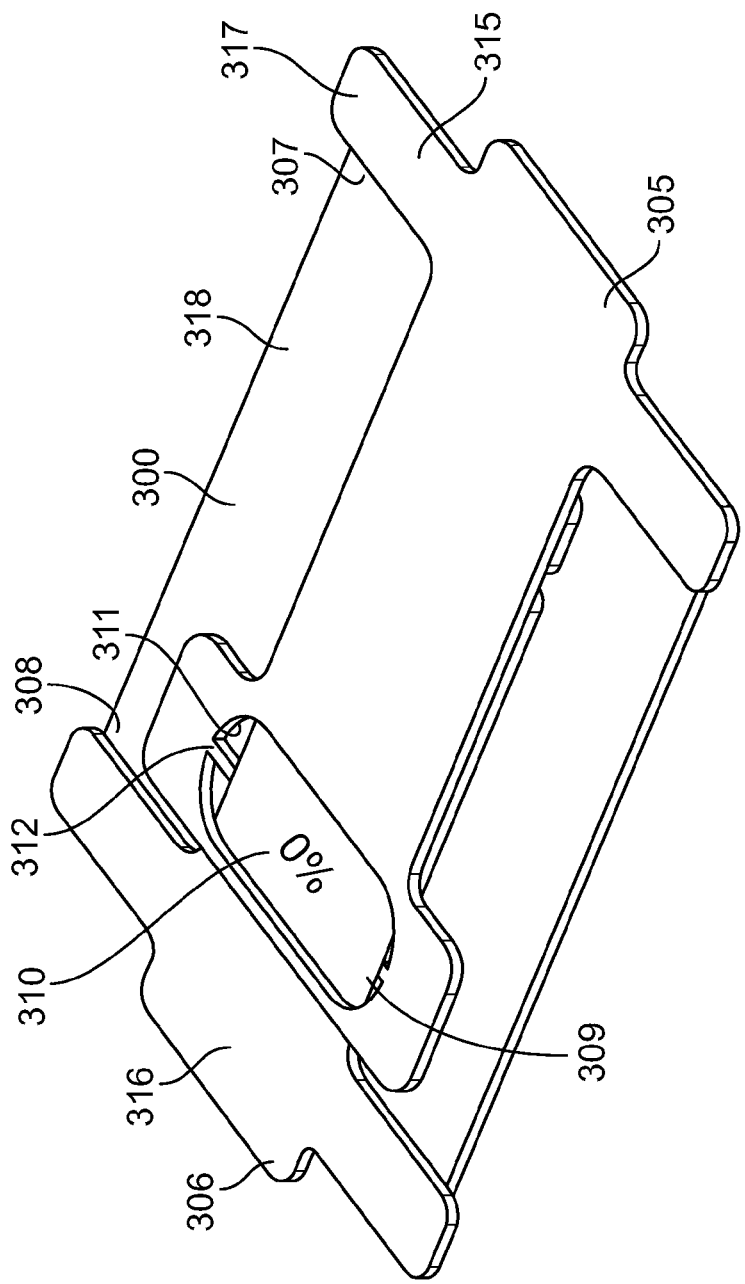
FIG. 3A is a top perspective view of a skin treatment device in a relatively unstrained configuration.
Figure 3B:
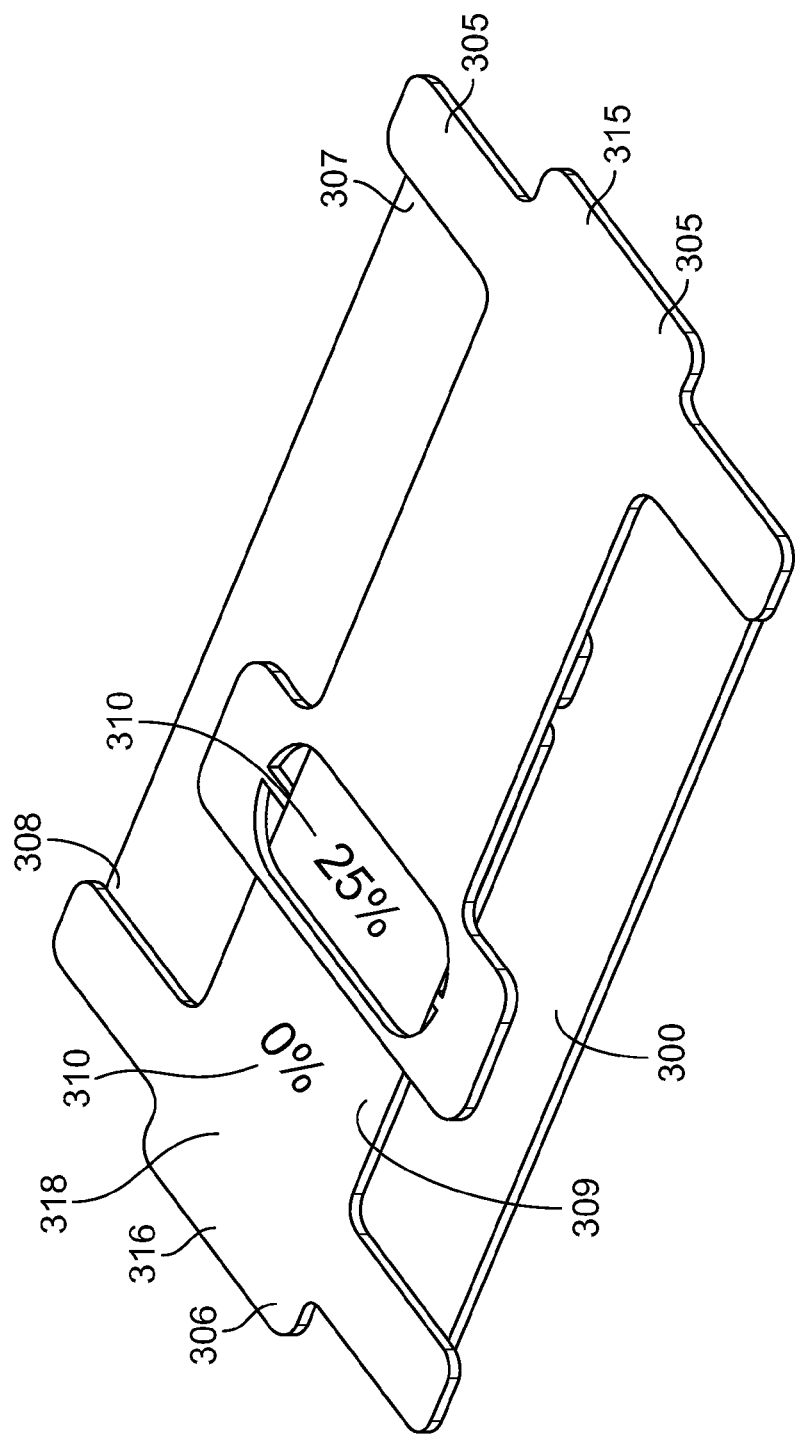
FIG. 3B is a top perspective view of the skin treatment device of FIG. 2A in a first strained configuration.
Figure 3C:
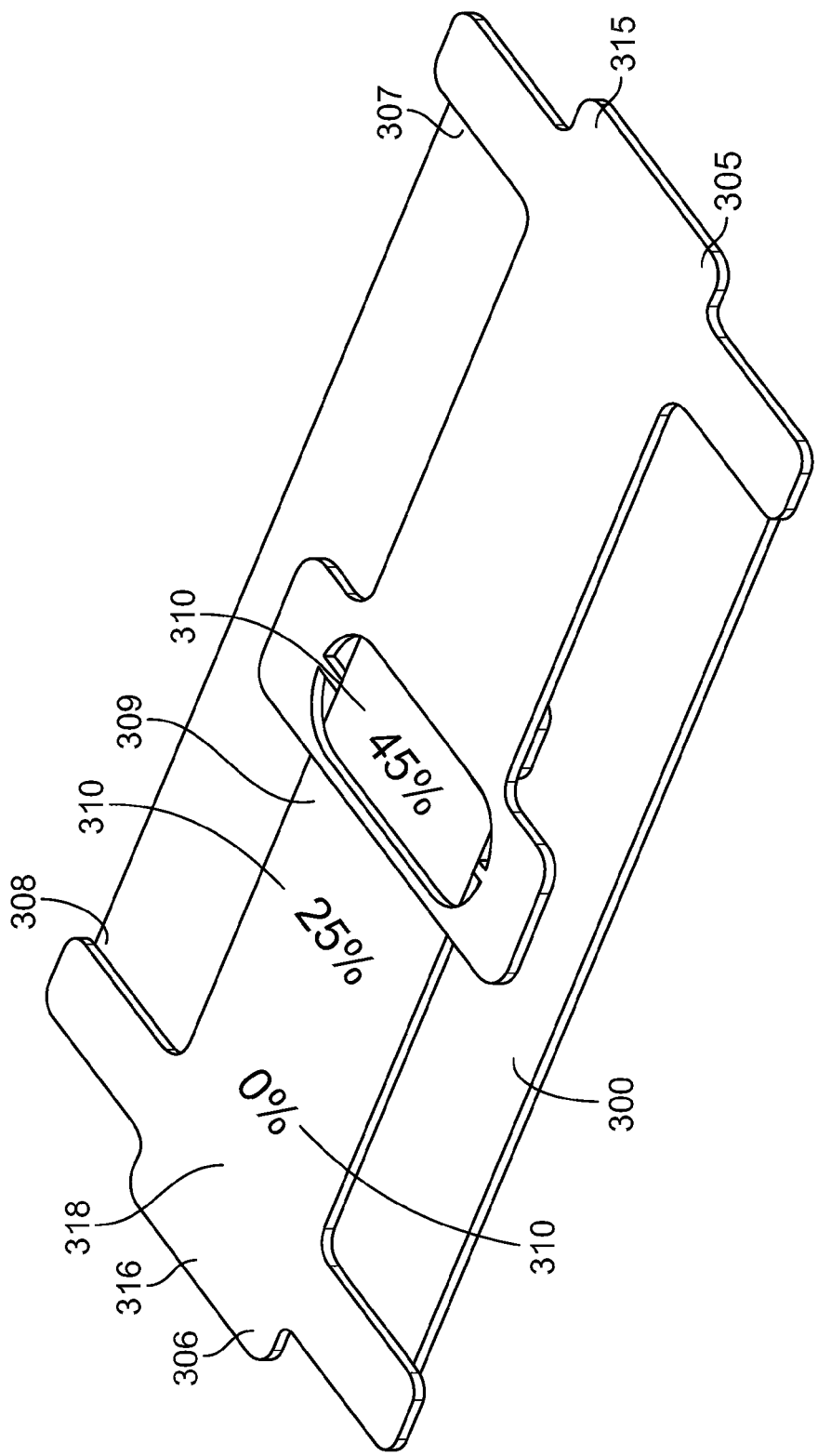
FIG. 3C is a top perspective view of the skin treatment device of FIG. 2A in a second strained configuration.
Figure 4A:
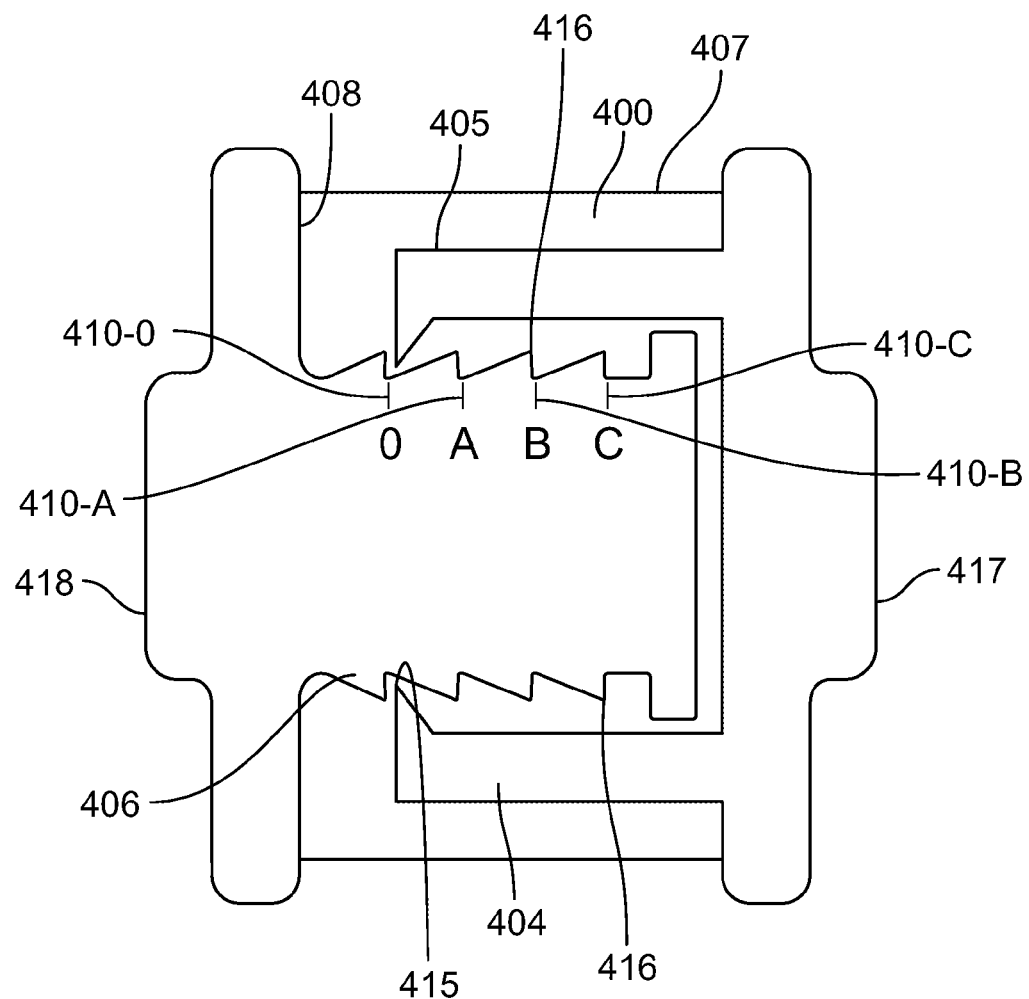
FIG. 4A is a top schematic view of a skin treatment device in a first configuration.
Figure 4B:
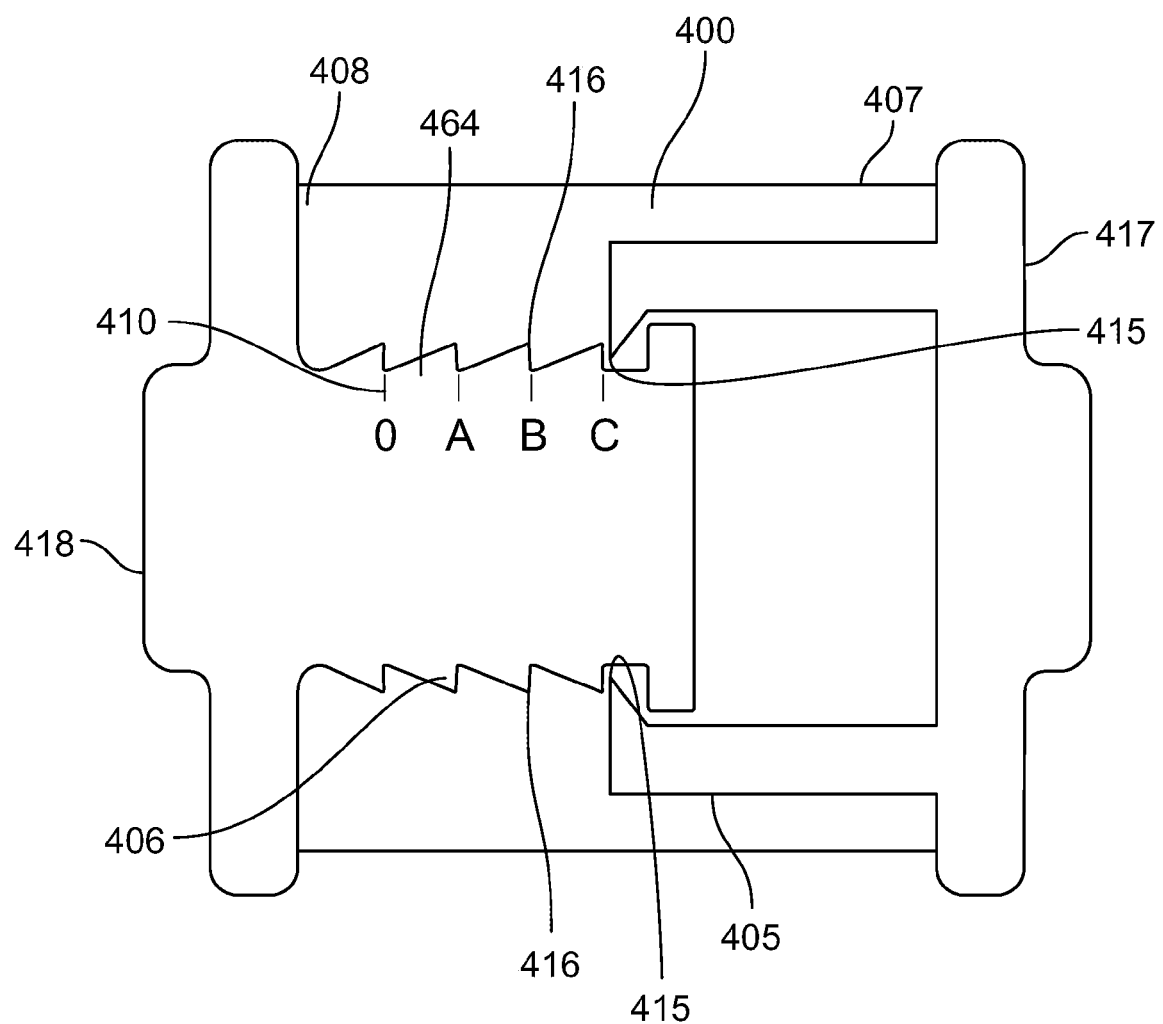
FIG. 4B is a top schematic view of the skin treatment device of FIG. 4A in a second strained configuration.

FIGS. 3A to 3C illustrate a strainable skin treatment device 300 which may be strained and/or stretched by exerting a tensioning force on the ends 307, 308 of the skin treatment device 300. A first opposing sliding element 305 is coupled at its end 317 to the first end 307 of the device 300 and a second opposing sliding element 306 is coupled at its end 316 to the second end 308. The sliding elements 305 may be removable coupled to the skin device 300, for example with an adhesive such as a preferentially removable adhesive as compared to skin adhesive used on skin interfacing surface. The first sliding element 305 and second sliding element 306 are slidably coupled to each other. The first sliding element 305 comprises a window 311 and securing bar 312. The second sliding element 306 comprises an elongate tab 309 having strain value indicators 310 on the top surface of the elongated tab 309 so that they may be viewed through window 311. The tab 309 of the second sliding element 306 is positioned under the first sliding element 305 and through the window 311 of the first sliding element 305. The securing bar 312 is positioned across the window 311 and below the tab 309, to hold the tab 309 in position through the window 311. Additional securing elements such as rails or guide elements may or may not be used to guide or maintain connection or alignment of the tab 309 with respect to the window 311. The ends 306, 307 and/or ends 316, 317 may be used to grip and strain the device 300, and may or may not comprise an inelastic material. As the skin treatment device 300 is strained, the elements 305, 306 slide apart and the tab 309 slides through the window 311. In the first position in FIG. 3A, the device is at a 0% strain in a first unstrained configuration. In FIG. 3B, the device 300 is strained about 25% as indicated by the strain indicator 310. In FIG. 3C the device is strained to 45% as indication by the indicator 310. A user may select the amount of strain desired. A user may use the indicators 310 to strain the device 300 to a desired degree. A skin adhesive may be provided on the skin attachment side 314 of the device 300. The ends 316, 317 may be attached to the top surface 318 (opposing a skin adhesive surface) of the device 300 by way of an adhesive, such as a preferentially removable adhesive as compared to skin adhesive used onskin adhesive surface After straining the device 300 a desired amount, it may be placed on a skin surface and the manipulation elements or sliding members 316, 317 may be removed. Alternatively, one of the sides 307 or 308 of the device may be applied to a skin surface. The device 300 may be strained a desired degree by pulling on the on the unattached one of the sides 307 or 308 while observing the indicia 310. Once a desired strain level is reached the unattached side 307 or 308 may be attached to the skin and the manipulation elements or sliding members 316, 317 may be removed FIGS. 4A and 4B illustrate a strainable skin treatment device 400 which may be strained and/or stressed by exerting a tensioning force on the ends 407, 408 of the skin treatment device 400. A ratchet 404 comprises first opposing ratchet element 405 coupled at its end 417 to the first end 407 of the treatment device 400, and a second opposing ratchet element 406 coupled at its end 418 to the second end 408 of the treatment device 400. Ratchet elements 405, 406 are movably coupled to each other so that they may be separated and the device may be tensile stressed and maintained in a strained configuration. The ends 407, 408 of the skin treatment device and/or ends 417, 418 of the ratchet elements 405, 406 may be used to grip and strain stress and/or stretch the device 400. The first ratchet element 405 comprises pawls 415 that engage sloped teeth 416 of the second ratchet element 406 and prevent movement backwards, loss of strain and/or complete relaxation of a tensile stressed skin treatment device 400. As the ends 417, 418 of the ratchet 404 move apart, the skin treatment device 400 is strained. Strain indicators or indicia 410 are on the second ratchet element 406 adjacent the teeth 416 and indicate a degree of strain of the device 400 based on which one of the teeth 416 engages the pawl 415. In the first position in FIG. 4A, the device 400 is relatively unstrained and in the position indicated by strain indicator "0" 410-0. In FIG. 4B, the device is strained to a maximum amount as indicated by the strain indicator "C"41 c. Positions 0, A, B, and C 410-( ), 410a, 410b and 410c correspond to different teeth or positions on the ratchet 404 and accordingly, different strain amounts or zero strain. A user may select the amount of strain. A user may use the indicators 410 to strain the device 400 to a selected or desired amount. A skin adhesive may be provided on the skin attachment side of the device 400 to adhere the device 400 to the skin. The ends 417, 418 may be attached to the top surface 419 of the device 400 by way of an adhesive, such as a preferentially removable adhesive as compared to skin adhesive used on skin interfacing surface. The ratchet elements 405, 406 may be peelable from the device or otherwise removably coupled to the device 400. After the device is applied to a subject, the ratchet elements 405, 406 may be removed leaving the device 400 on the skin. In other variations, one or more of the ratchet elements and/or pawl elements may be left in place or otherwise configured to be non-removable. In some variations comprising removable elements used only during the application of the device, the removable elements may be attached to the device using adhesives comprising a higher shear force resistance but a lower T-peel force resistance, relative to the same force.

Figure 5A:
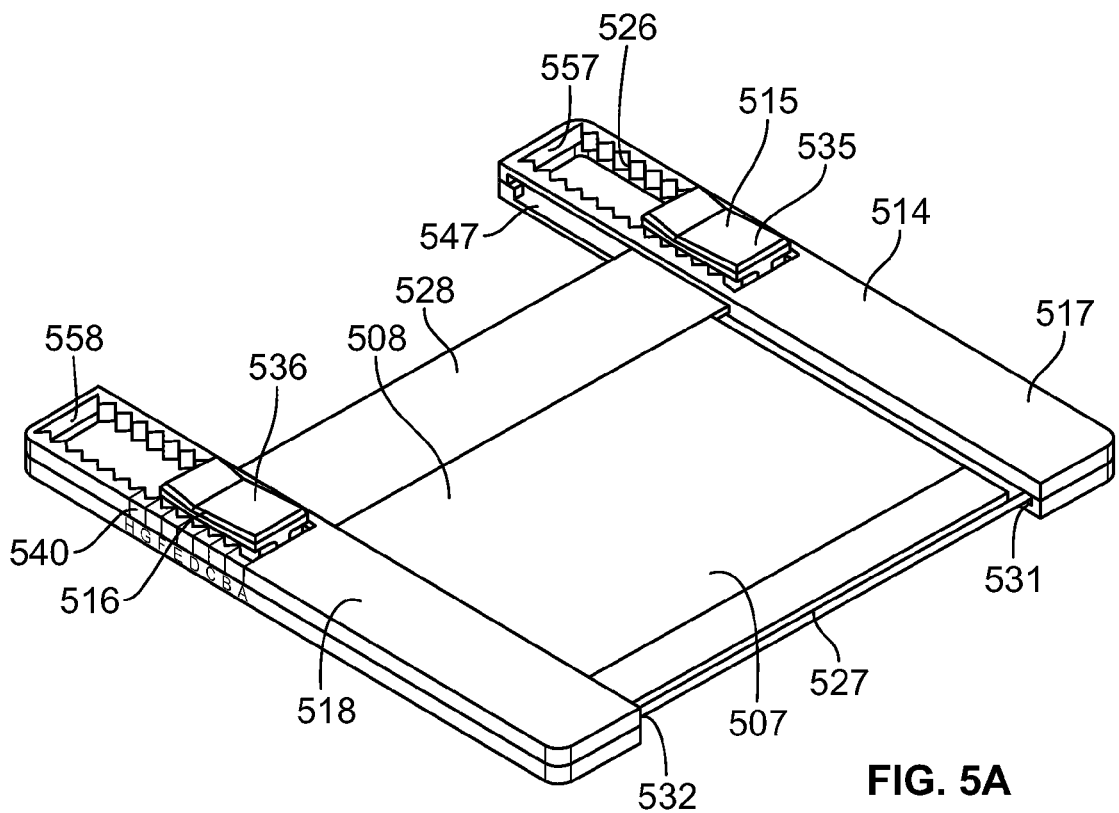
FIG. 5A is a top perspective view of a skin treatment device in a first configuration.
Figure 5B:
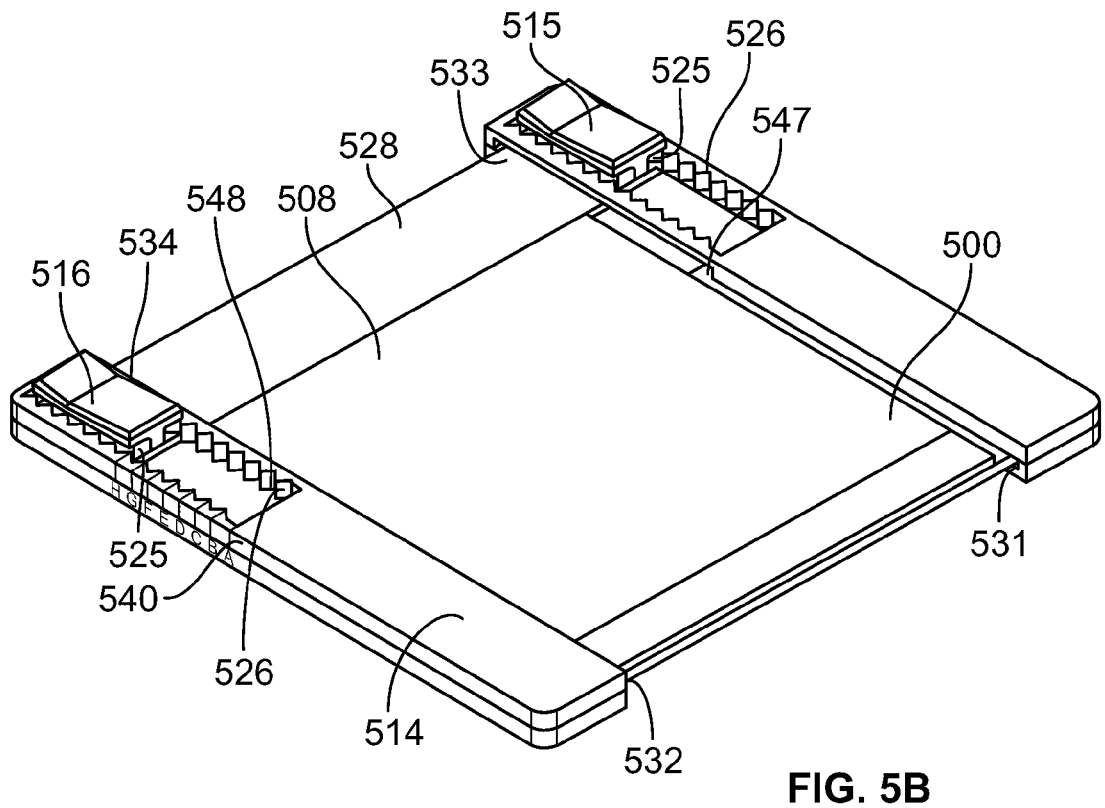
FIG. 5B is a top perspective view of the skin treatment device of FIG. 5A in a second configuration.

FIGS. 5A and 5B illustrate a strainable skin treatment device 500 which may be strained, stretched and/or tensile stressed by exerting a tensioning force on ratcheted tabs 515, 516 or other manipulation elements of a straining structure 514. The skin treatment device 500 is coupled at its first end 507 to a first attachment element 527. The first attachment element 527 is coupled at its sides 531,532 to side supports 517, 518 of the straining structure 514. The second and opposite end 508 of the skin treatment device 500 is coupled to a second attachment element 528. The sides 533,534 of second attachment element are slidably positioned in slots 547, 548 formed in side supports 517, 518 along a portion of the length. Ratcheted openings 557, 558 are formed through the top surface 550 of side supports 517, 518 along the portion of the length of the slots 547, 548. The tabs 515, 516 are coupled through openings 557, 558 to sides 533, 534 respectively of attachment element 528 within the slots 547, 548 respectively The ratchet 504 comprises the teeth 526 of the ratcheted openings 547, 548 and pawls 525 formed in sides of the tabs 515, 516. Pawls 525 may be disengaged from the teeth 516 by depressing the buttons 535, 536 on the tabs 515, 516 when straining the device 500. The pawls 525 engage the teeth 526 when the buttons 535, 536 are released to maintain the device 500 in a strained configuration by pushing buttons 535, 536 to release pawls 525. The buttons 535, 536 may be biased by a spring in a pawl engaging direction. When buttons 535, 536 are released at a selected position, a desired device strain is maintained or locked in.

The tabs 515, 516 may be extended to strain the attached dressing. Strain indicators or indicia 540, for example as described herein may be provided on the straining structure 514 or device 500 to indicate a degree of strain of the device 500. The device may be strained a selectable amount based on which ones of the teeth 516 engage the pawls 515. A user may use the indicators 540 to strain the device 500 to a selected or desired amount. A skin adhesive may be provided on the skin attachment side of the device 500 to adhere the device 500 to a subject. The attachment elements 527 and 528 may be attached to the treatment device 500 by a preferentially removable adhesive as compared to skin adhesive used on skin interfacing surface of the device 500. The tabs 515, 516 are coupled to the attachment element 528. The straining structure may be removable from the device 500 leaving the device 500 on the skin.

Figure 6A:
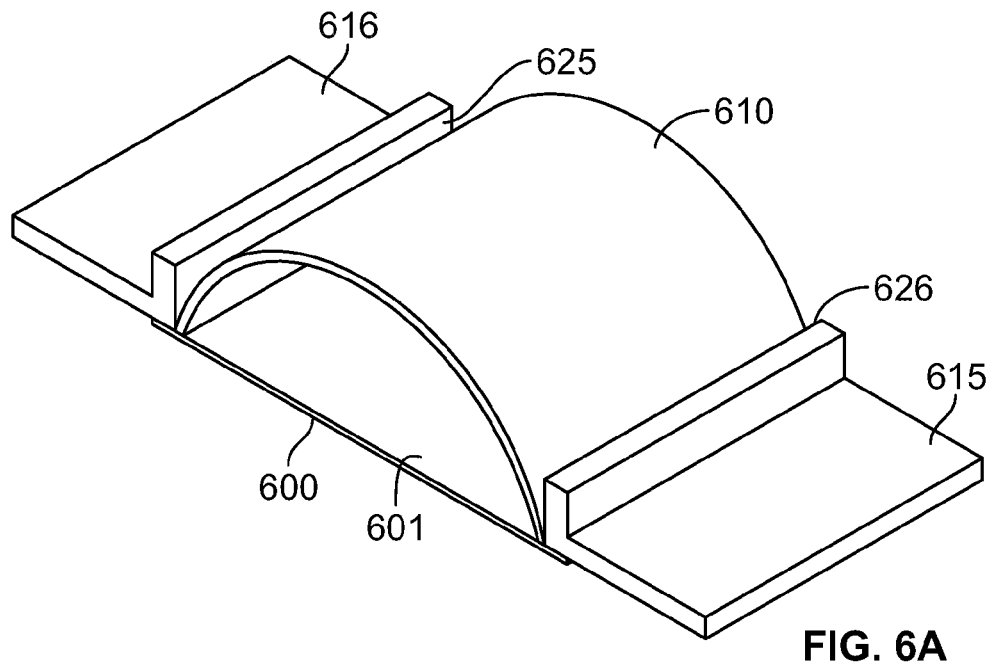
FIG. 6A is a top perspective view of a skin treatment device in a first configuration.
Figure 6B:
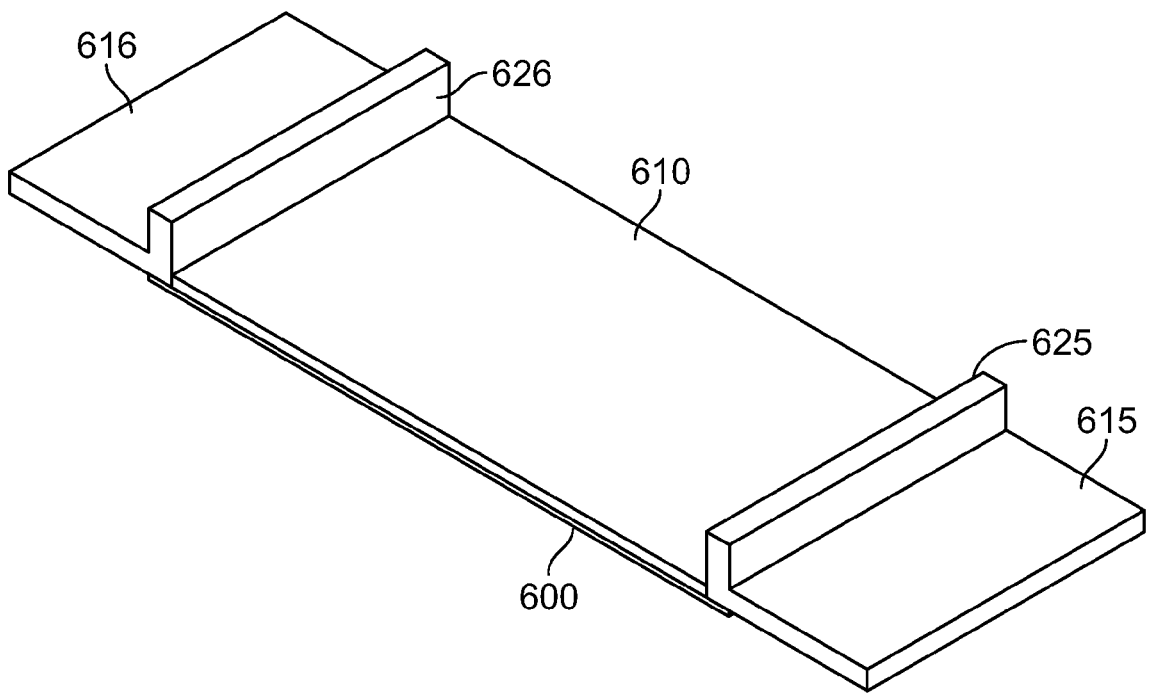
FIG. 6B is a top perspective view of the skin treatment device of FIG. 6A in a second, strained configuration.
Figure 7A:
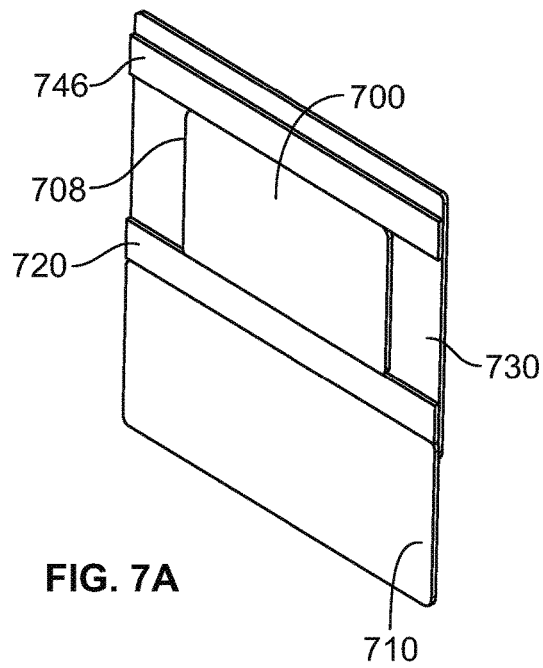
FIG. 7A is a top perspective view of a skin treatment device in an unstrained configuration.
Figure 7B:
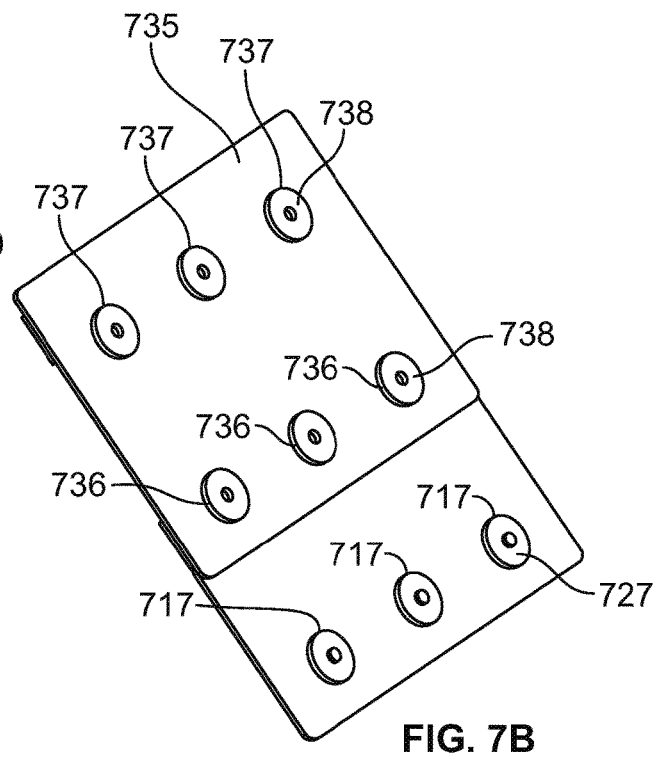
FIG. 7B is a bottom perspective view of the skin treatment device of FIG. 7A in the unstrained configuration.
Figure 7C:
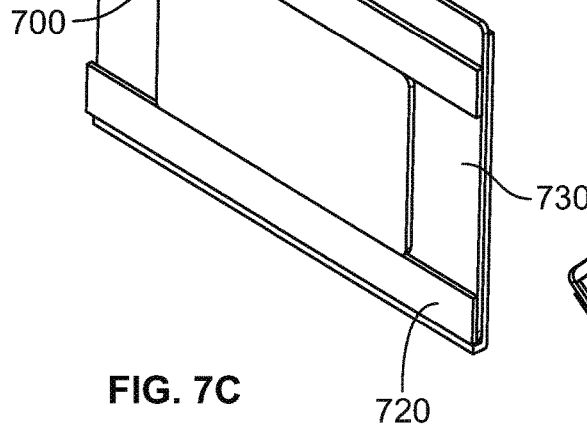
FIG. 7C is a top perspective view of a skin treatment device of FIG. 7A in a strained configuration.
Figure 7D:
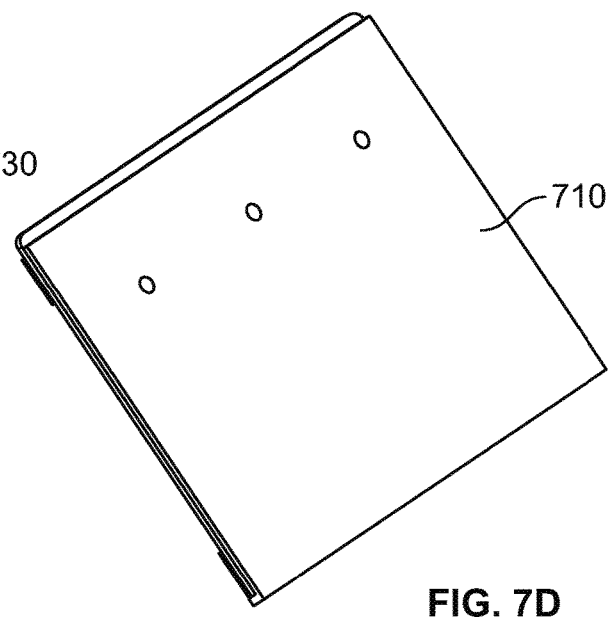
FIG. 7D is a bottom perspective view of the skin treatment device of FIG. 7C in the strained configuration.

FIGS. 6A and 6B illustrate a strainable skin treatment device 600 with handles 615, 616 coupled to a first surface 601 of a treatment device 600, for example, with a peelable adhesive. The skin treatment device 600 may be strained and/or tensile stressed by exerting a tensioning force on handles 615, 616. A strain limiter 610 is coupled to inner edges or walls 625, 626 of the handles 615, 616, respectively, for example by adhering, welding, or overmolding. The strain limiter 610 comprises at least one element that is bent, folded, arced or otherwise shaped in a first configuration, for example, as shown for example, in FIG. 6A where the distance between the inner walls 625,626 is less than when the device 600 is strained. When a user manually strains the device by separating the handles 615, 616, the strain limiter, straightens and maintains the strain by engaging the side walls 625, 626 in a straight configuration. The strain limiter 610 may be constructed for example, of LDPE, FEP, nylon, metal. The strain limiter 610 may be coupled to the side walls of the handles 615, 616. The strain limiter 610 and handles 615, 616 may be released from the device 600 after it is applied to a skin surface by peeling it away.

FIGS. 7A to 7D illustrate a strainable skin treatment device 700. The treatment device 700 is coupled to a sheet 710 at a first side 705 of the device, for example by way of an adhesive or other securing element 720 capable of resisting shear stresses during straining, e.g., KAPTON® polyimide tape (DuPont, Wilmington, Del.). The device 700 may be anchored at a second end 708 to a support structure or backing 730 on a first surface 733 of the backing 730, for example by way of a securing element 740 such as a KAPTON® tape or adhesive that is removable from the device 700. The device 700 may be manually or otherwise strained by grasping or pulling the sheet 710 in a straining direction. A second opposing surface 735 of the backing 730 comprises a first row 736 of snap buttons 738 and a second (or more) row 737 of snap buttons 738 that engage with a row 717 of mating snap buttons 727 on the sheet 710. After the device 700 is strained by tensioning or pulling the sheet 710. The sheet 710 may be folded back so that the row 717 is aligned with a row of snap buttons on the backing 730. Each row may be positioned so that a known amount of strain is created in the dressing depending on which row is used. For example, the first row 736 of buttons 738 would be commensurate with an amount of strain that is less that the amount of strain commensurate with the second row 737 of buttons 738. Accordingly a user may select an amount of strain.

Figure 8A:
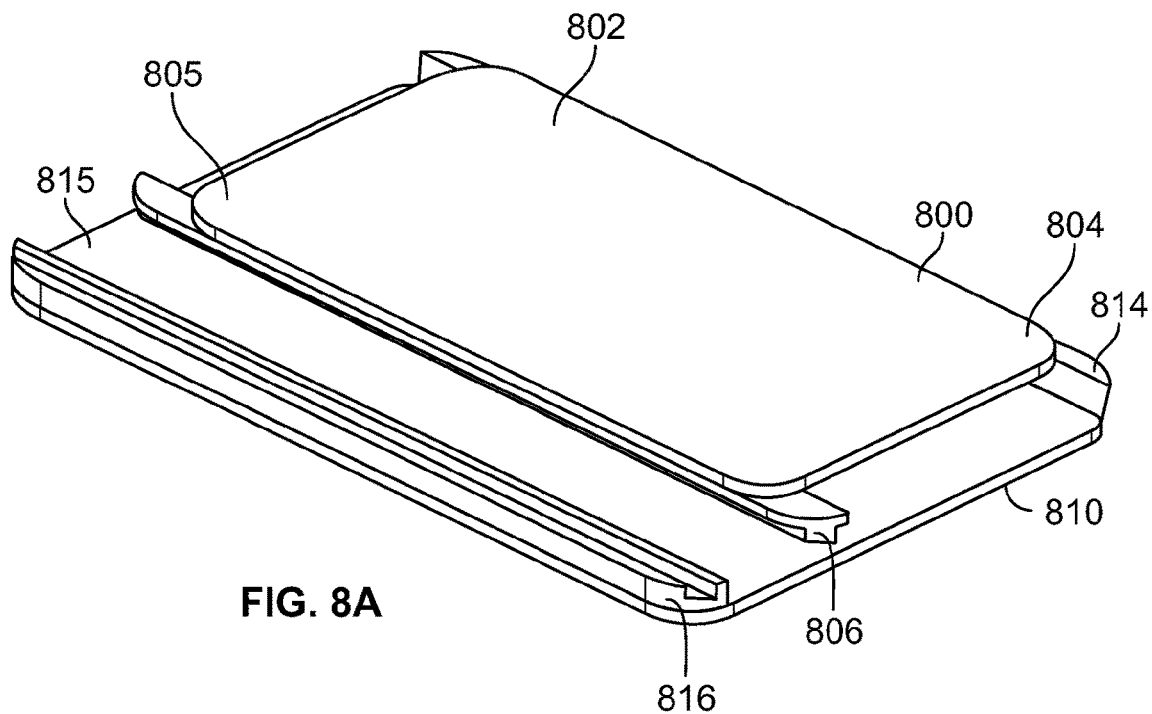
FIG. 8A is a top perspective view of a skin treatment device in an unstrained configuration.
Figure 8B:
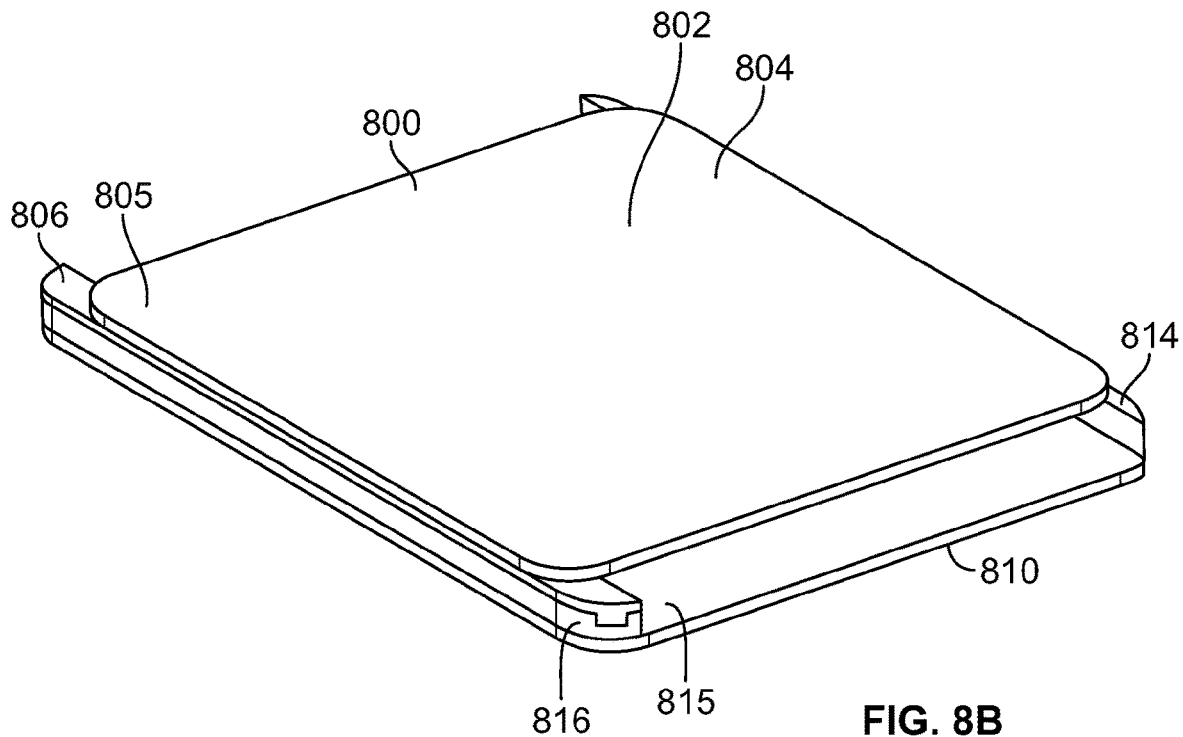
FIG. 8B is a top perspective view of the skin treatment device of FIG. 8A in a strained configuration.

FIGS. 8A and 8B illustrate a strainable skin treatment device 800. The skin treatment device 800 is coupled on a first side 804 to a corresponding first side 814 of a stiffer or more rigid backing 810. A coupling element 806 is coupled to the second side 805 of the treatment device 800. The coupling element 806 engages or snaps into a receiving element 816 on the second side 815 of the backing 810. A user may manipulate the coupling element 806 to strain the treatment device 800 and then attach the coupling element 806 to the receiving element 816. The coupling element 806 and engaging element 816 may be snapped together and apart for example as with press fit a tongue in groove type connector arrangement. They also may be slid apart in a planar direction with respect to the treatment device 800 and the backing 810. The skin treatment device 800 and the backing 810 may be removably coupled on the first sides 804, 814 by way of a peelable adhesive or other coupling mechanism. For example, the first sides 804, 814 may be coupled in a similar manner as coupling element 806 and receiving element 816. Thus, after straining and attaching the treatment device 800 to the backing 810 in a strained configuration, and after applying an adhesive side 802 of the strained device 800 to skin to be treated, the backing 810 may be released from the device 800 by snapping or sliding the backing 810 apart from the device 800.

Figure 9A:
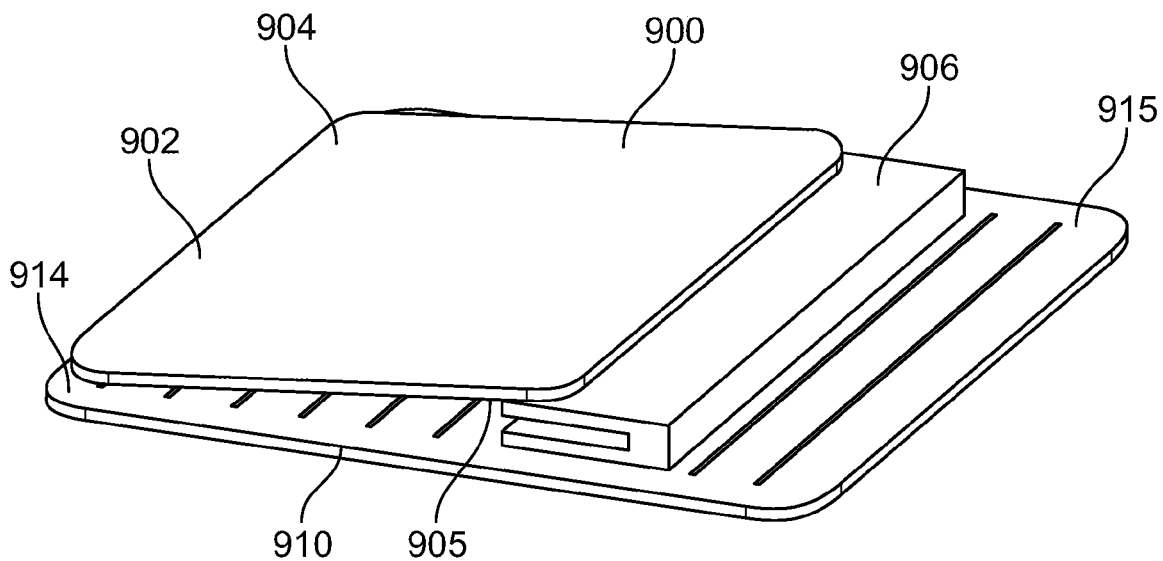
FIG. 9A is a top perspective view of a skin treatment device in a first configuration.
Figure 9B:
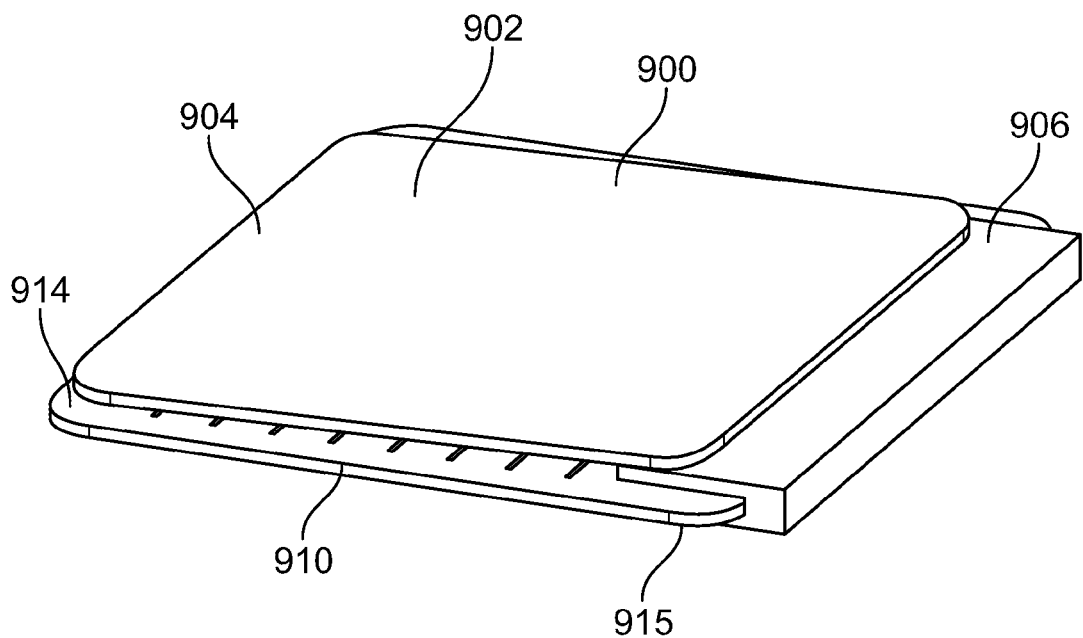
FIG. 9B is a top perspective view of the skin treatment device of FIG. 9A in a second strained configuration.

FIGS. 9A and 9B illustrate a strainable skin treatment device 900. A first side 904 of a treatment device 900 is anchored at a first end 914 of a more stiff or rigid backing 910 for example by a removable adhesive or other removable coupling element. A hook or other coupling element 906 is coupled to the second side 905 of the treatment device 900. The coupling element 906 engages or hooks onto the second side 915 of the backing 910. A user may manipulate the coupling element 906 to strain the treatment device 900 and then attach the coupling element 906 to the second side 915 of the backing 910. The skin treatment device 900 may be removably coupled to the coupling element 906 by way of a peelable adhesive or other coupling mechanism. Thus, after straining and attaching the treatment device 900 to the backing 910 in a strained configuration, and after applying an adhesive side 902 of the strained device 900 to skin to be treated, the backing 910 and coupling mechanism or hook 906 may be released from the device 900 by peeling apart from the device 900.

Figure 10A:
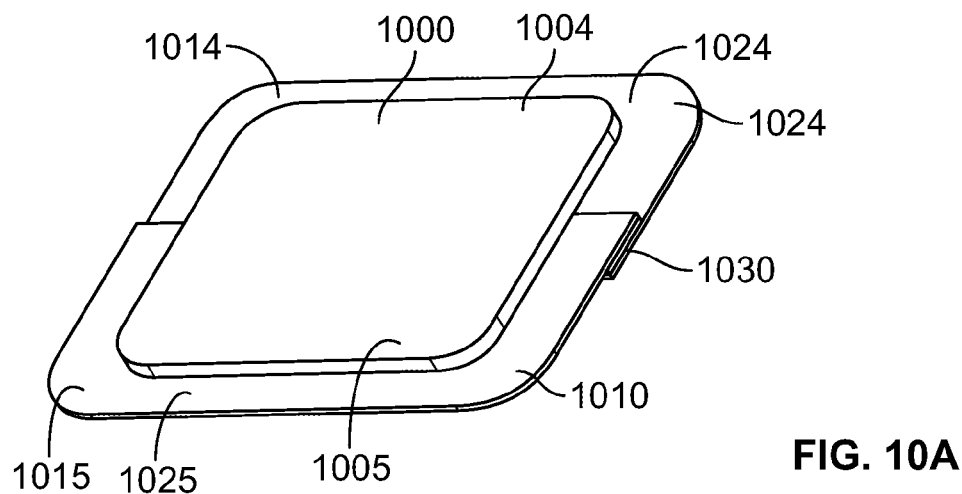
FIG. 10A is a top perspective view of a skin treatment device in a first configuration.
Figure 10B:
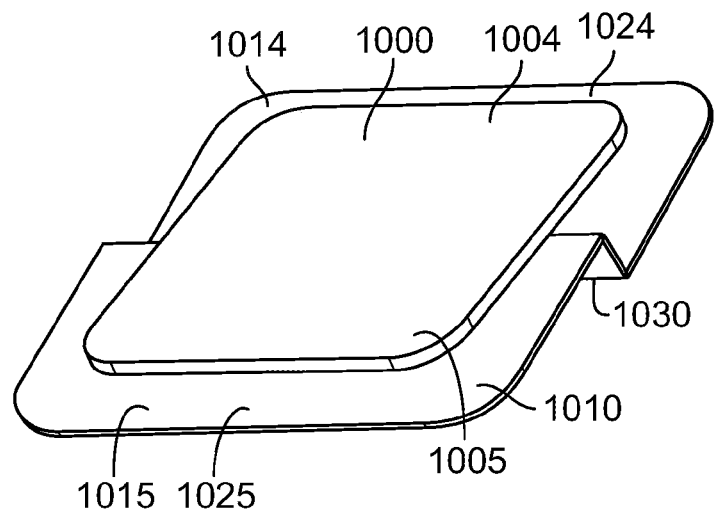
FIG. 10B is a top perspective view of the skin treatment device of FIG. 10A in a second configuration.
Figure 10C:
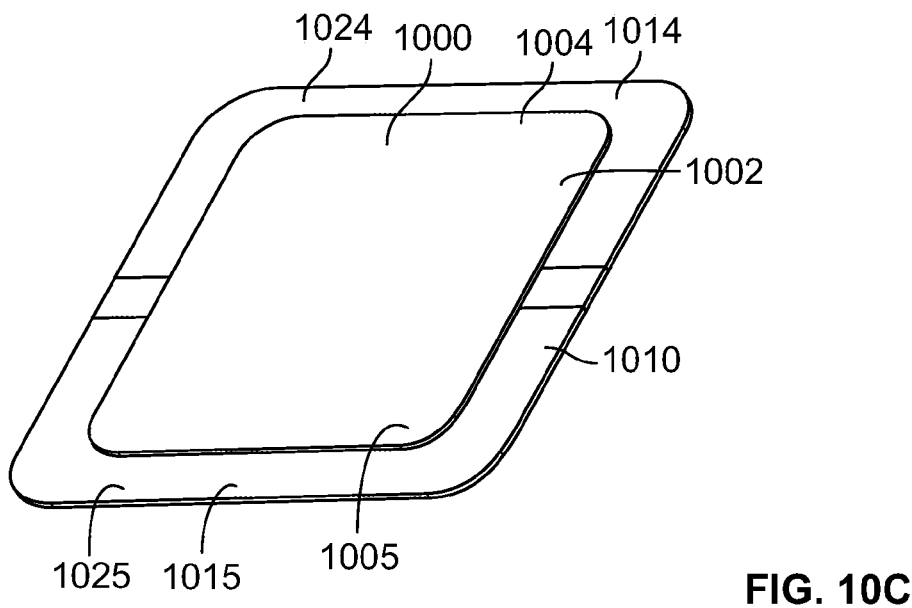
FIG. 10C is a top perspective view of the skin treatment device of FIG. 10A in a third strained configuration.
Figure 10D:
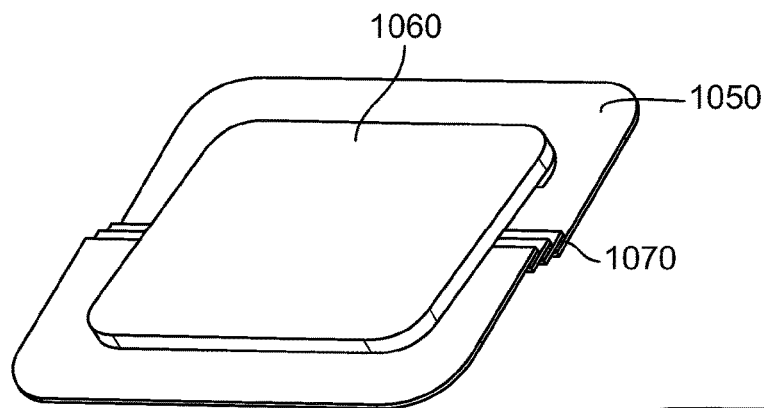
FIG. 10D is a top perspective view of the skin treatment device in a first configuration.

FIGS. 10A to 10C illustrate a strainable skin treatment device 1000. The skin treatment device 1000 is coupled, for example with a peelable adhesive or other coupling mechanism, on opposing sides 1004, 1005 adjacent opposing sides 1014, 1015 of a straining backing 1010 or applicator 1010. The backing 1010 is shown in a folded configuration in FIG. 10A where a portion of the backing 1010 includes a tri-fold 1030. The fold 1030 decreases the length of the backing 1010 (FIG. 10A). Margins or areas 1024, 1025 of the opposing sides 1014, 1015 extend beyond the sides 1004, 1005 of the device 1000 permitting a user to grasp or manipulate the free areas to exert and tensile or straining force on the device 1000 through the backing 1010. When a straining force is exerted, the tri-fold 1030 unfolds (FIG. 10B) and straightens (10C). The backing 1010 thus limits the strain of the device 1000. After the device 1000 is strained, an adhesive side 1002 of the strained device 1000 may be applied to skin to be treated and the backing 1010 may be removed from the device 1000 leaving the device 1000 on the skin.

Figure 10E:
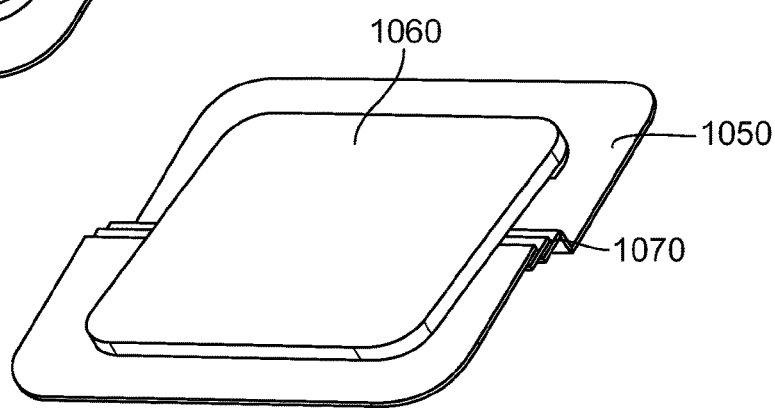
FIG. 10E is a top perspective view of the skin treatment device of FIG. 10D in a second strained configuration.
Figure 10F:
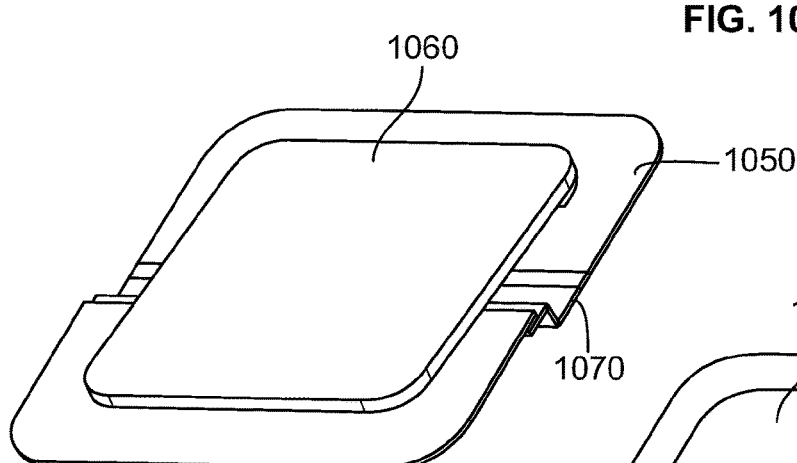
FIG. 10F is a top perspective view of the skin treatment device of FIG. 10D in a third strained configuration.
Figure 10G:
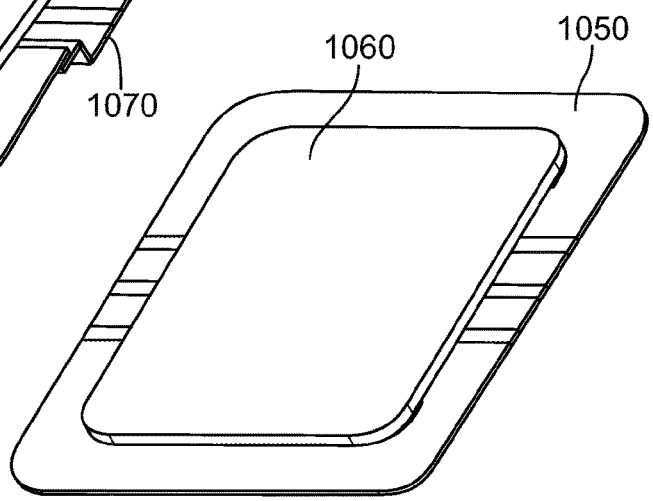
FIG. 10G is a top perspective view of the skin treatment device of FIG. 10D in a fourth strained configuration.

As shown in FIGS. 10D to 10G, a plurality of folds 1070 may be provided in a backing 1050. Each fold 1070 may correspond or provide a particular strain value or amount. A user may select numbers of folds depending on desired strain. Folds 1070 may be configured to release sequentially as shown in FIGS. 10E to 10G, or may be secured and releasable, for straining the dressing 1060, for example by a tape that resists unfolding of a particular fold unless removed.

Figure 11A:
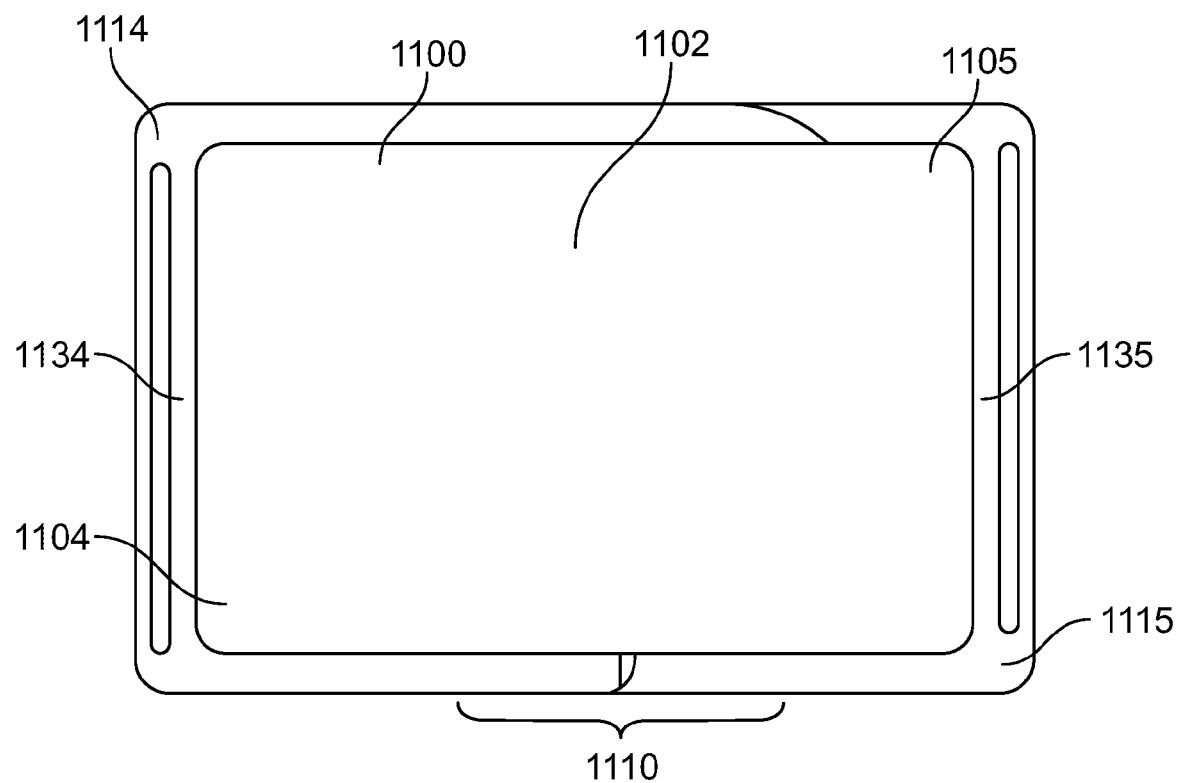
FIG. 11A is top schematic view of a skin treatment device in a first configuration.
Figure 11B:
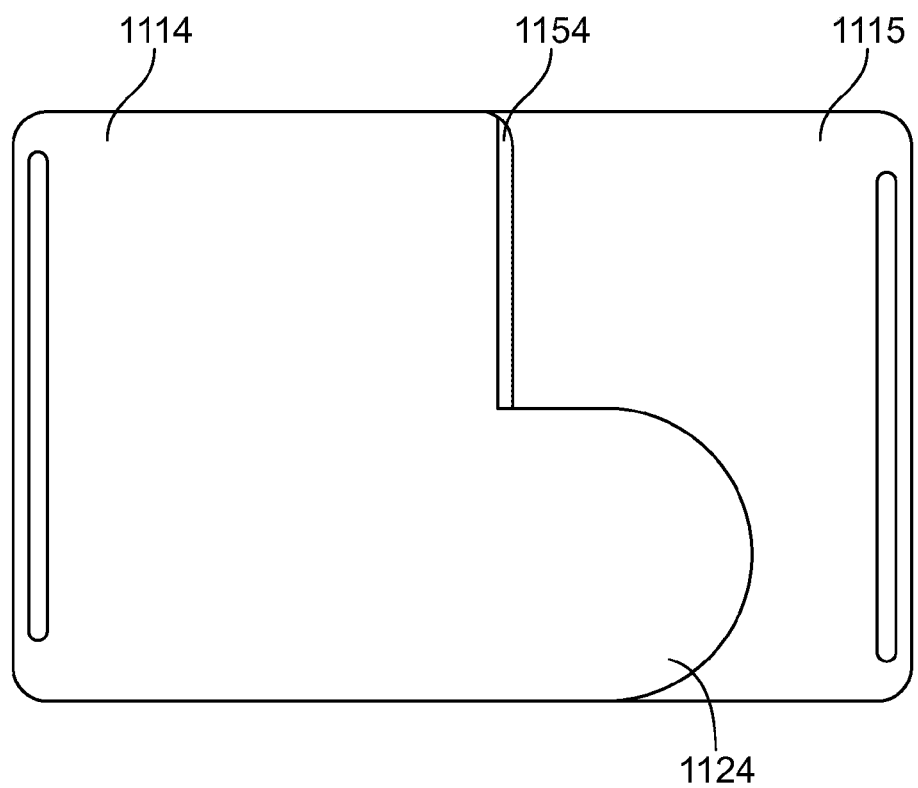
FIG. 11B is a bottom schematic view of the skin treatment device of FIG. 11A in the second configuration.
Figure 11C:
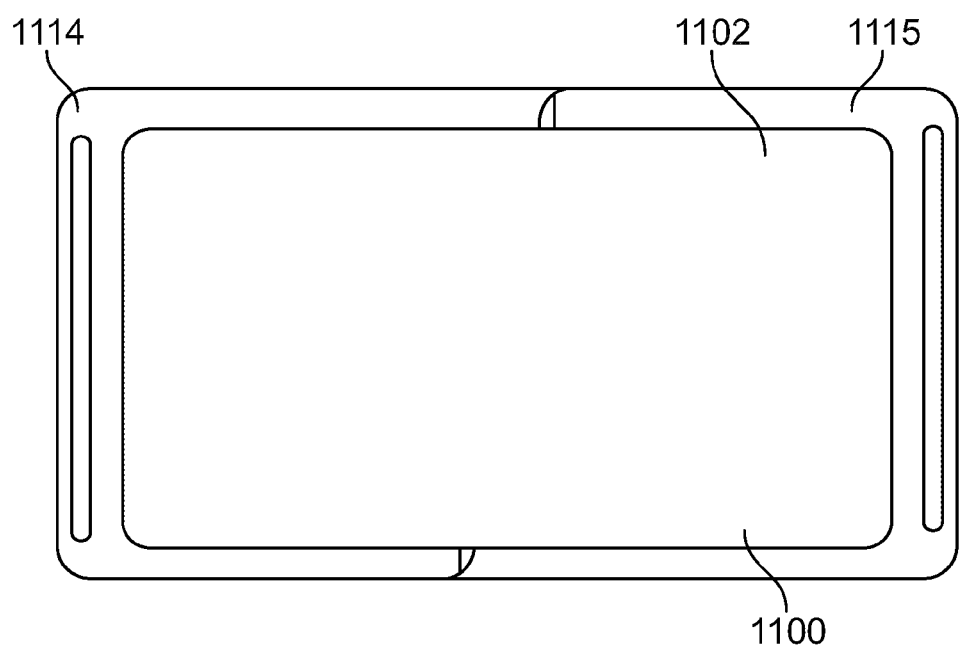
FIG. 11C is a top schematic view of the skin treatment device of FIG. 11A in a second, strained configuration.
Figure 11D:
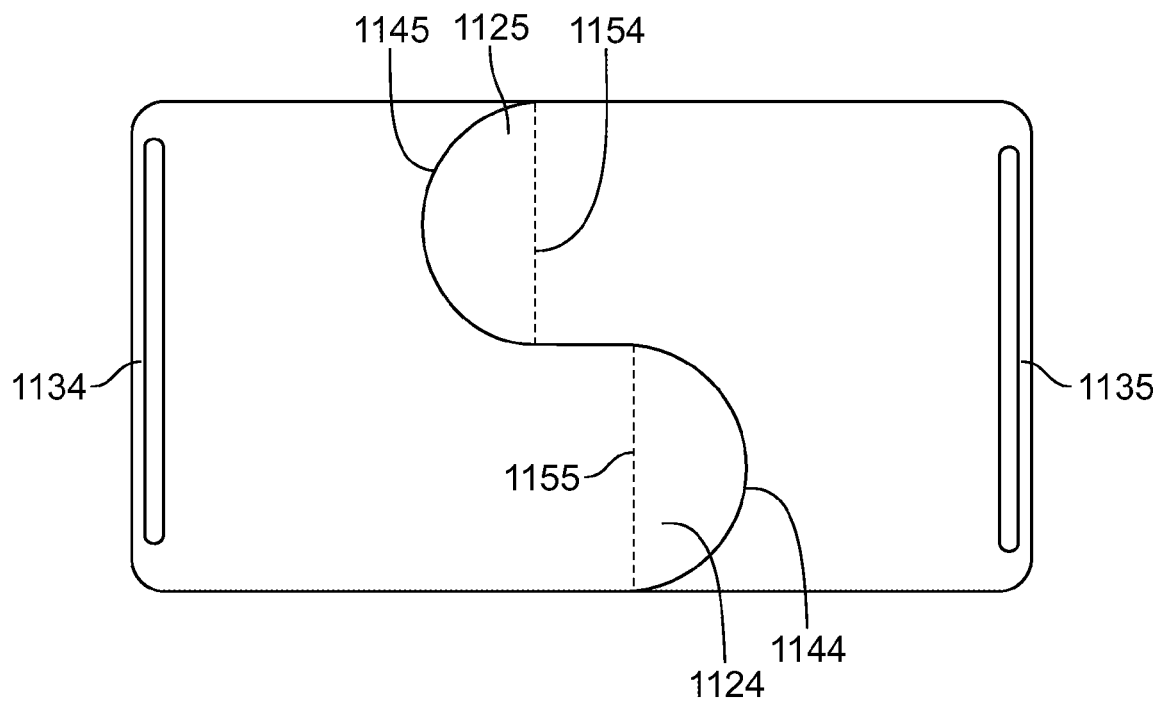
FIG. 11D is a bottom schematic view of the skin treatment device of FIG. 11A in a second, strained configuration.

FIGS. 11A to 11D illustrate a strainable skin treatment device 1100. The skin treatment device 1100 is coupled on opposing sides 1104, 1105 to sides of segments 1114, 1115 of a straining backing or applicator 1110. The device 1100 is free from to the backing 1110 in a straining zone between the opposing sides 1104, 1105. The backing 1110 comprises segments 1114, 1115 having middle tab portions 1124, 1125 that overlap in the unstrained configuration (FIGS. 11A and 11B) wherein the backing 1110 has a first length. Margins or areas 1134, 1135 of sides of segments 1114, 1115 extend beyond the sides 1104, 1105 of the device 1100 permitting a user to grasp the free areas to exert a tensile or straining force on the device 1100. When a straining force is exerted, the tabs 1124, 1125 of segments 1114, 1115 separate. After separation, when released, the edges 1144, 1145 of the tabs 1124, 1125 engage by overlapping opposing edge portions 1155, 1154 of segments 1115, 1114 respectively, maintaining the backing in a lengthened configuration and thus maintaining the strain in the device 1100. (FIGS. 11C and 11D). After the device 1100 is strained, an adhesive side 1102 of the strained device 1100 may be applied to skin to be treated and the backing 1110 may be removed from the device 1100 leaving the device 1100 on the skin.

Figure 12A:
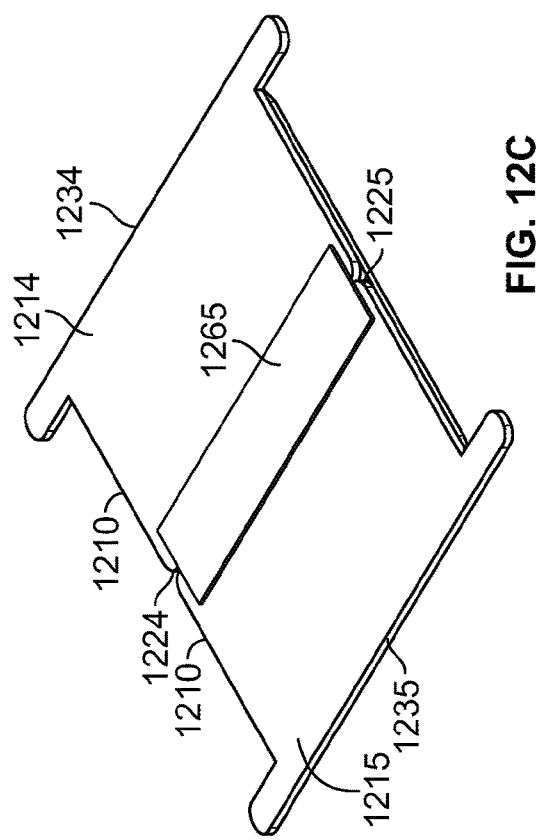
FIG. 12A is top schematic view of a skin treatment device in a first configuration.
Figure 12C:
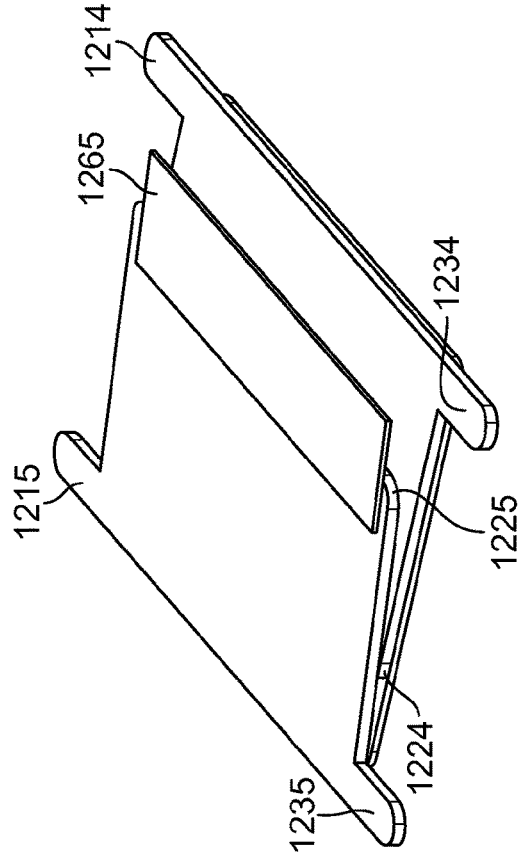
FIG. 12C is a top schematic view of the skin treatment device of FIG. 12A in a second, strained configuration.
Figure 12B:
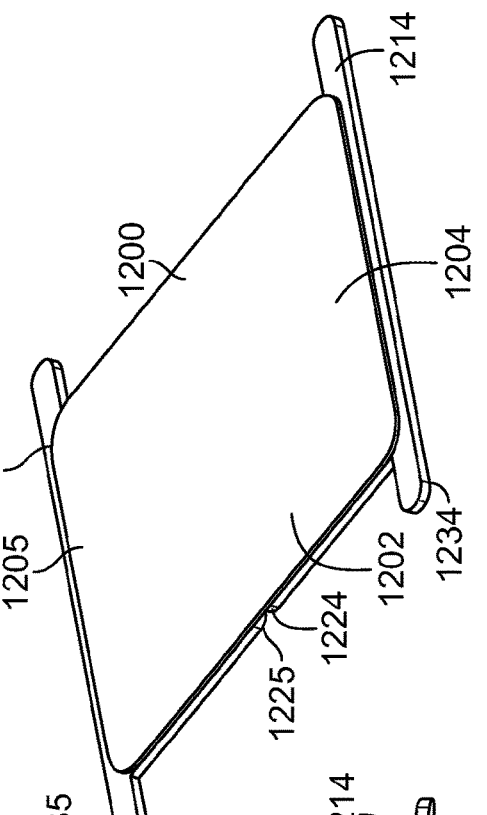
FIG. 12B is a bottom schematic view of the skin treatment device of FIG. 12A in the second configuration.
Figure 12D:
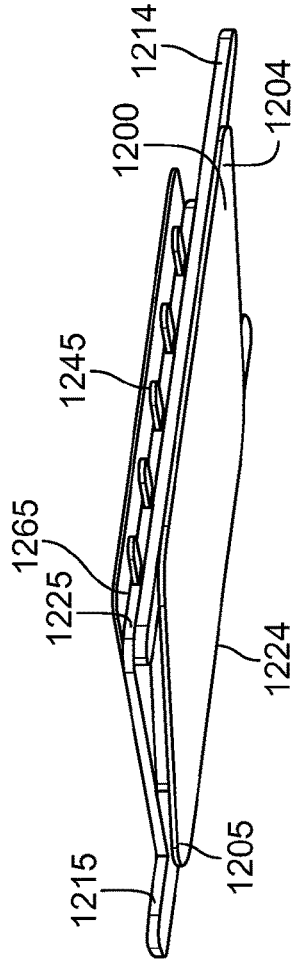
FIG. 12D is a bottom schematic view of the skin treatment device of FIG. 12A in a second, strained configuration.

FIGS. 12A to 12D illustrate a strainable skin treatment device 1200. The skin treatment device 1200 is coupled on opposing sides 1204, 1205 to sides of segments 1214, 1215 of a straining backing or applicator 1210. The device 1200 is free from to the backing 1210 in a straining zone between the opposing sides 1204, 1205. The backing 1210 comprises segments 1214, 1215 having middle edges 1224, 1225 that overlap in the unstrained configuration (FIGS. 12A and 12B) wherein the backing 1210 has a first length. Handle elements 1234, 1235 of sides of segments 1214, 1215 permit a user to grasp and manipulate the segments 1214, 1215 to exert a tensile or straining force on the device 1200. When a straining force is exerted, the edges 1224, 1225 of segments 1214, 1215 separate. After separation, when released, the edges 1224, 1225 of each have features that engage with each other, maintaining the backing 1210 in a lengthened configuration and thus maintaining the strain in the device 1200. (FIGS. 12C and 12D). The features may be, for example a mortise and tenon (1244) type of joint. A guide 1265 on the segment 1215 may also guide the edges 1224, 1225 in to an aligned engagement when the device 1200 is strained. After the device 1200 is strained, the adhesive side 1202 of the strained device 1200 may be applied to skin to be treated and the backing 1210 may be removed from the device 1200 leaving the device 1200 on the skin.

Figure 13A:
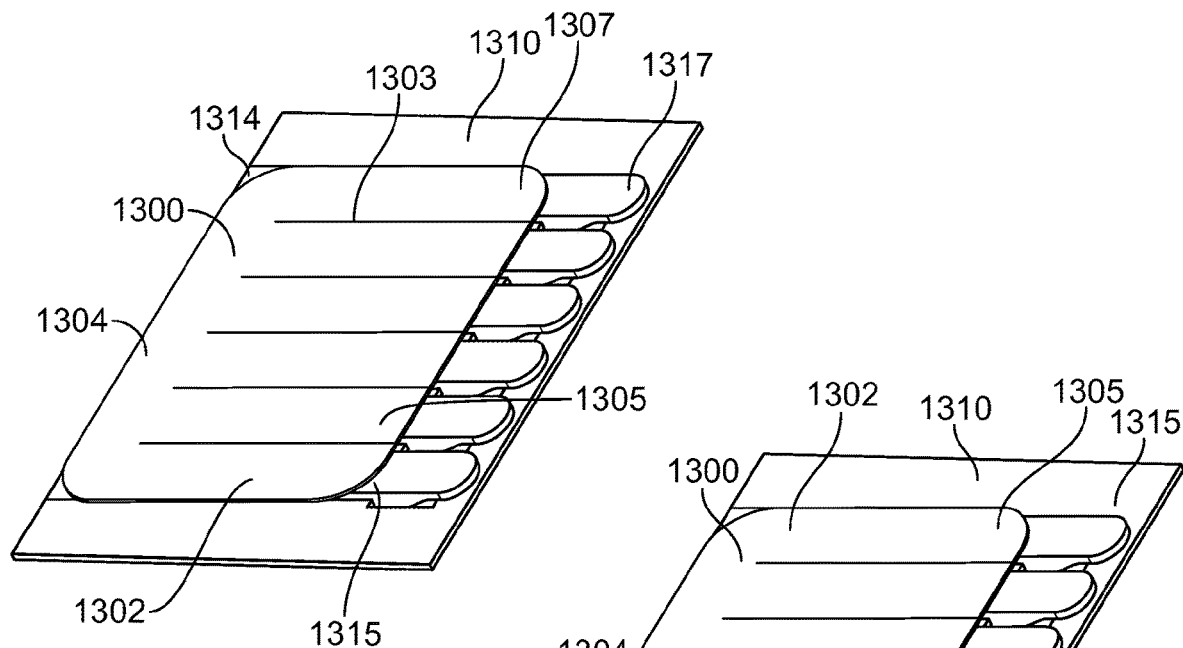
FIG. 13A is a top perspective view of a skin treatment device in a first configuration.
Figure 13B:
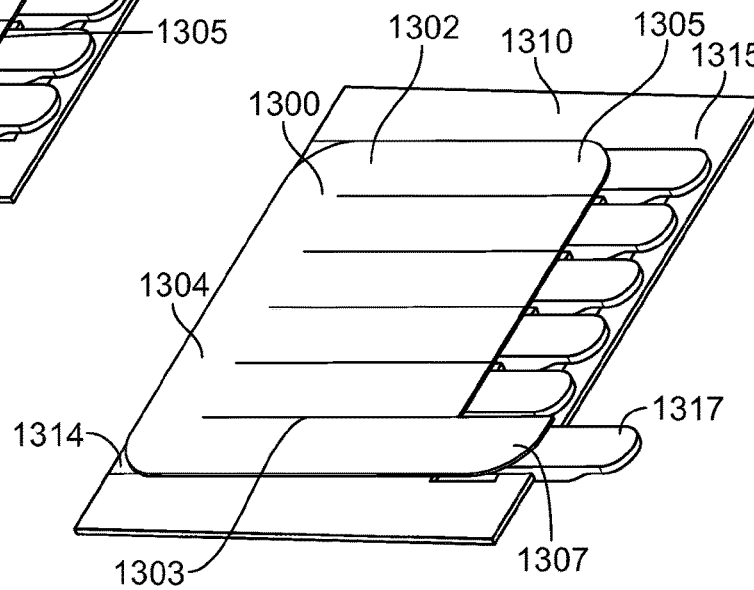
FIG. 13B is a top perspective view of the skin treatment device of FIG. 13A in a second, partially strained configuration.
Figure 13C:
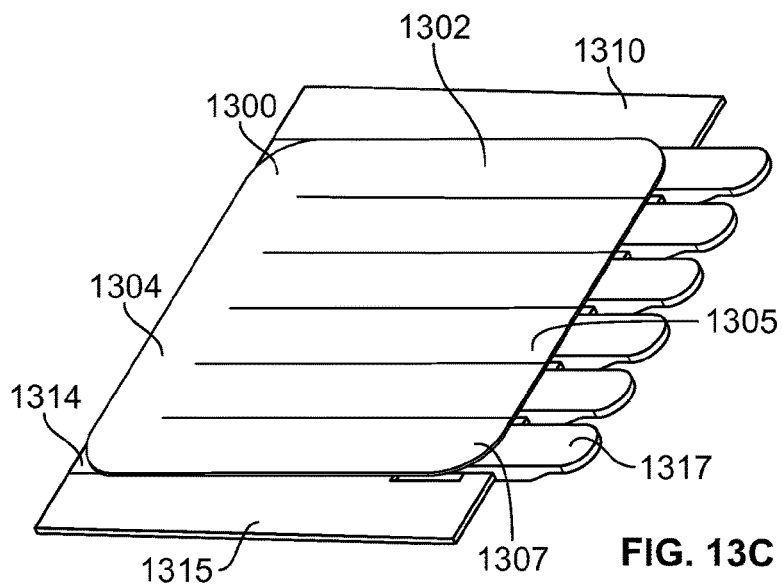
FIG. 13C is a top perspective view of the skin treatment device of FIG. 13A in a third, strained configuration.

FIGS. 13A to 13C illustrate a strainable skin treatment device 1300. A first side 1304 of a treatment device 1300 is anchored at a first side 1314 of a more stiff or rigid backing 1310 for example by a removable adhesive or other removable coupling element. The treatment device 1300 includes slits or breaks 1303 that form fingers 1307. The backing 1310 includes movable fingers 1317 that are extendable away from first end 1314 of backing 1310. The fingers 1307 of the device 1300 are each attached to a corresponding movable finger 1317 of the backing 1310 at a second side 1315 of the backing 1310. Each of the movable fingers 1317 may be extended away from side 1314 to strain a corresponding finger 1307 of the device. A user may select one or more or all fingers 1307 to be strained. Each finger 1307 may also be variably strained to a desired degree. FIG. 13A illustrates an unstrained device 1310 on the backing. FIG. 13B illustrates an individual finger 1307 strained. FIG. 13C illustrates all fingers 1307 strained. The skin treatment device 1300 may be removably coupled to the side 1314 of the backing 1310 and/or edges 1305 of the finger 1307 by way of a peelable adhesive or other coupling mechanism. Thus, after straining and after applying the adhesive side 1302 of the strained device 1300 to skin to be treated, the backing 1310 including the fingers 1317 may be released from the device 1300 for example by peeling apart from the device 1300.

Figure 14A:
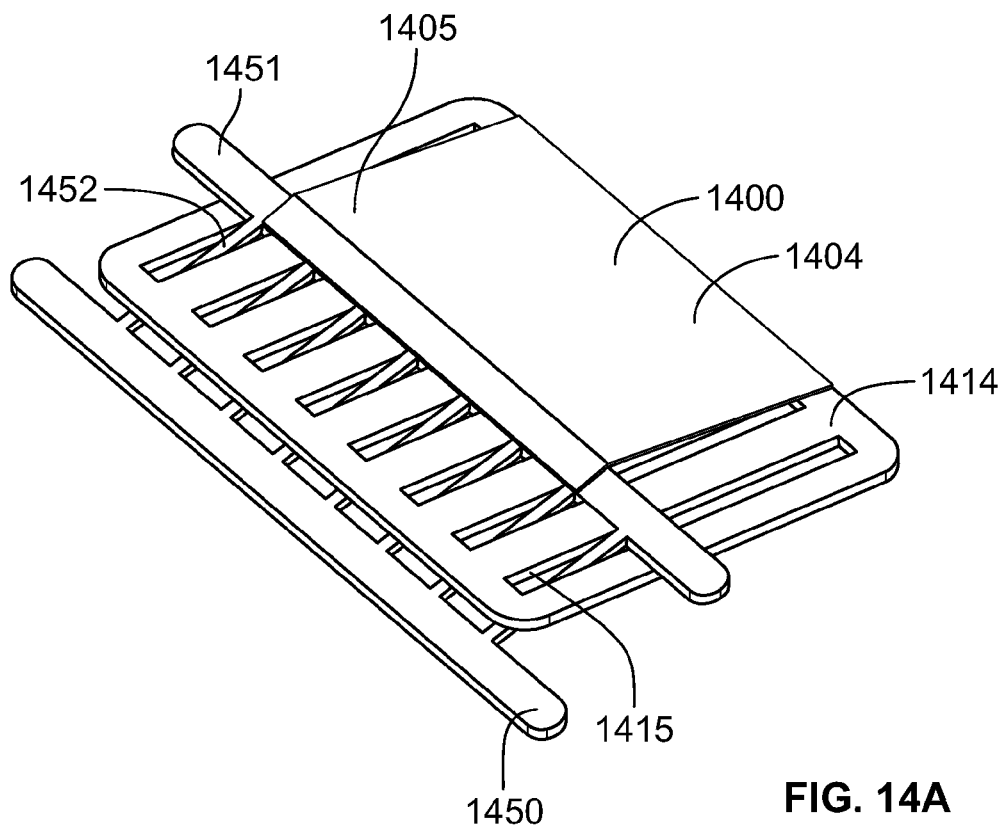
FIG. 14A is a top perspective view of a skin treatment device in a first configuration.
Figure 14B:
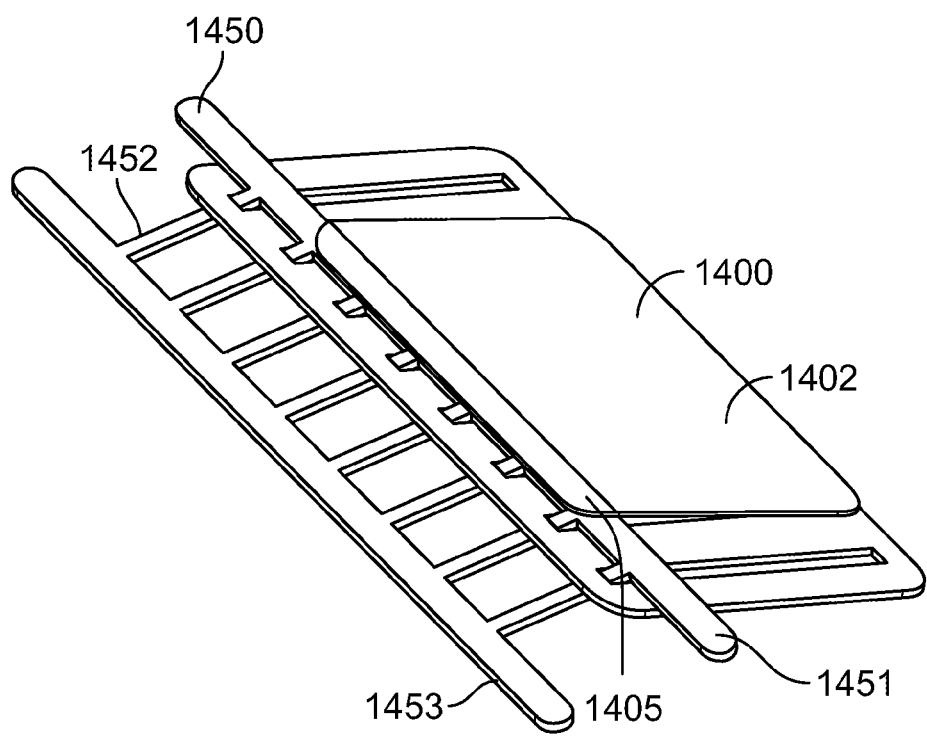
FIG. 14B is a top perspective view of the skin treatment device of FIG. 14A in a second, strained configuration.

FIGS. 14A and 14B illustrate a strainable skin treatment device 1400. The skin treatment device 1400 is coupled on a first side 1404 to a corresponding first side 1414 of a stiffer or more rigid backing 1410. A straining element 1450 is coupled to the second side 1405 of the treatment device 1400. The straining element 1450 comprises a first bar or handle 1451 that is coupled to the second side 1405 of the treatment device 1400, for example, by way of an adhesive or other coupling element. The straining element 1450 further comprises connecting bars 1452 that extend through slots 1415 in rigid backing 1410 and connect the first bar or handle 1451 to a second bar or handle 1453. A user may use the straining element 1450 to strain the treatment device 1400 by grasping the second handle or bar 1453 and sliding the connecting bars 1452 through the slots 1415 (FIG. 14B). The skin treatment device 1400 and the backing 1410 may be removably coupled on the first sides 1404, 1414 by way of a peelable adhesive or other coupling mechanism. Thus, after straining and after applying the adhesive side 1402 of the strained device 1400 to skin to be treated, the backing 1410 may be released from the device 1400 by peeling the backing 1410 from the device 1400.

Figure 14C:
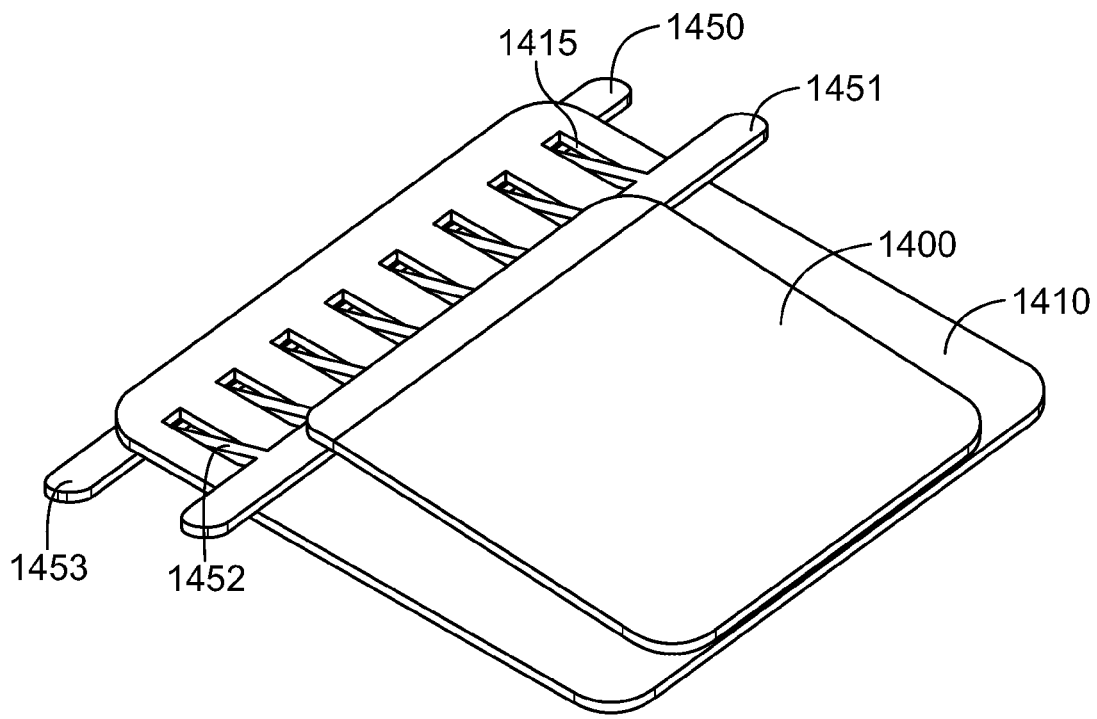
FIG. 14C is a top perspective view of a the skin treatment device in a first configuration.
Figure 14D:
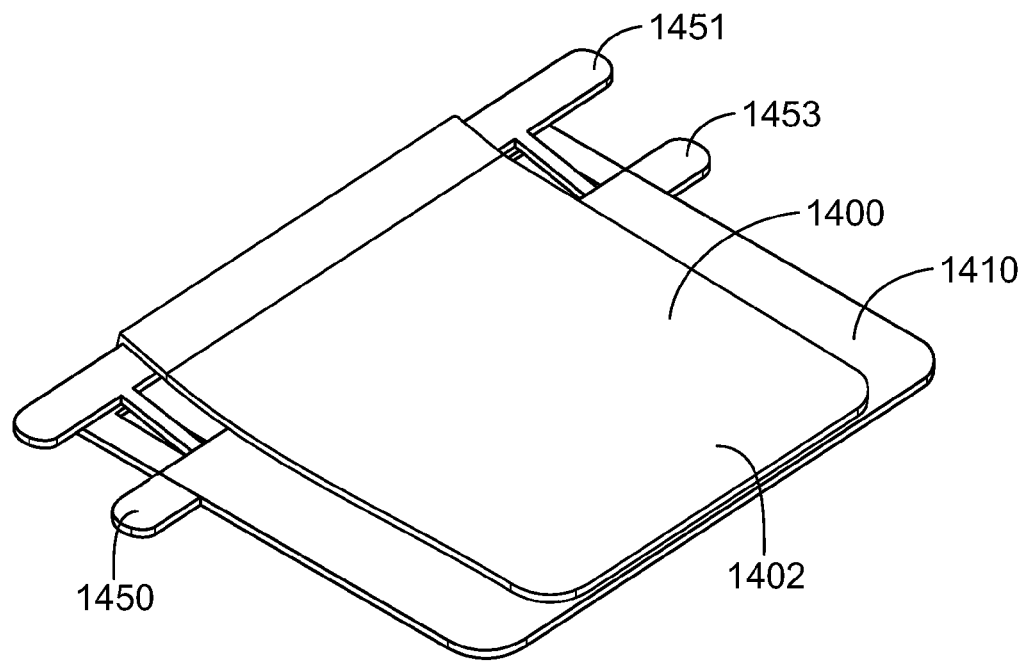
FIG. 14D is a top perspective view of the skin treatment device of FIG. 14C in a second, strained configuration.

FIGS. 14C and 14D illustrate the strainable skin treatment device 1400 and rigid backing 1410 of FIGS. 14A and 14B. A user may use the straining element 1450 to strain the treatment device 1400 by grasping the handle or bar 1453 and rotating it so that the connecting bars 1452 rotate with in the slot 1415 as shown in FIG. 14D. After straining and after applying the adhesive side 1402 of the strained device 1400 to skin to be treated, the backing 1410 may be released from the device 1400 by peeling the backing 1410 from the device 1400.

Figure 15A:
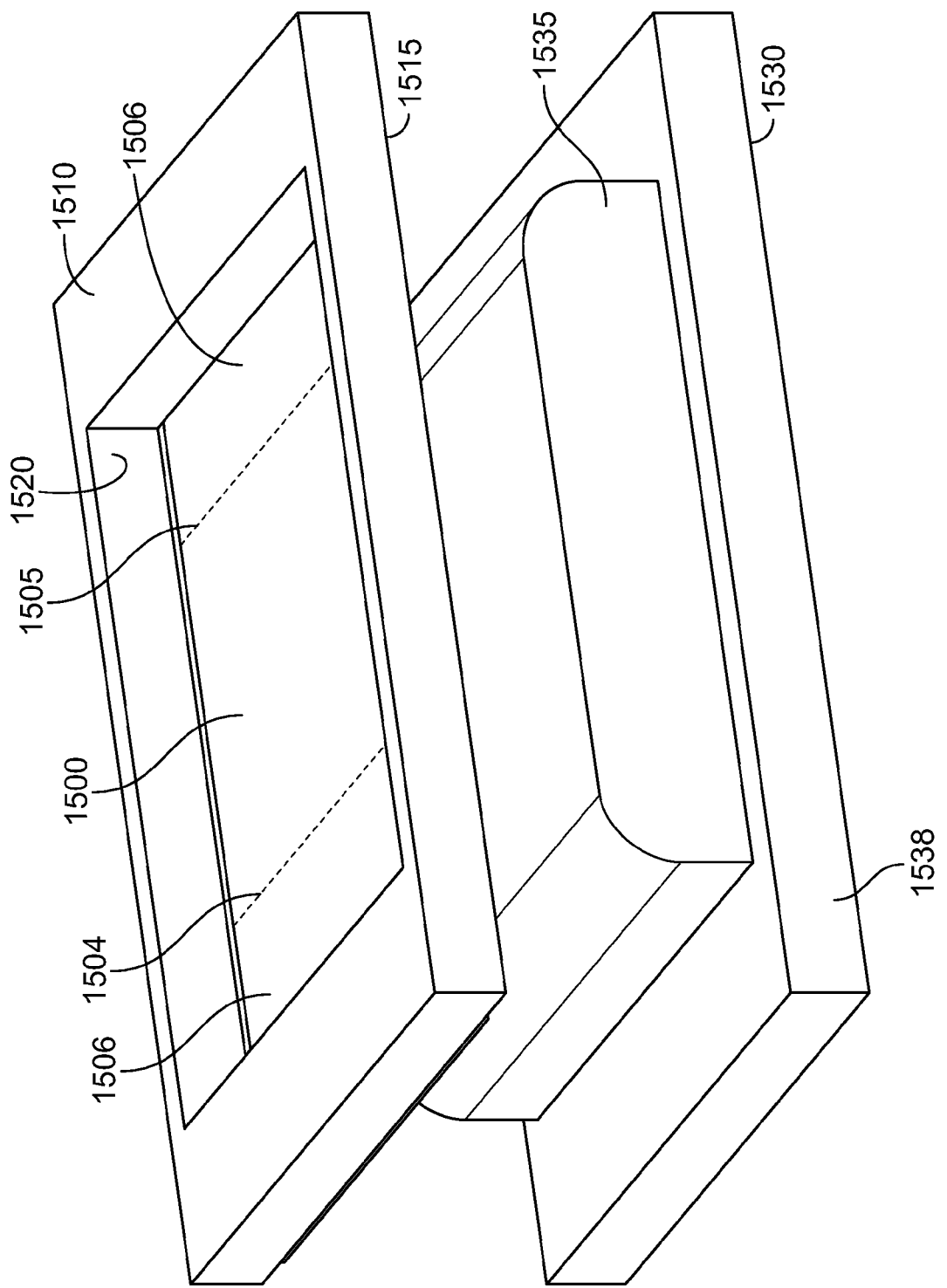
FIG. 15A is a side perspective view of a tensioning device and skin treatment device prior to straining.
Figure 15B:
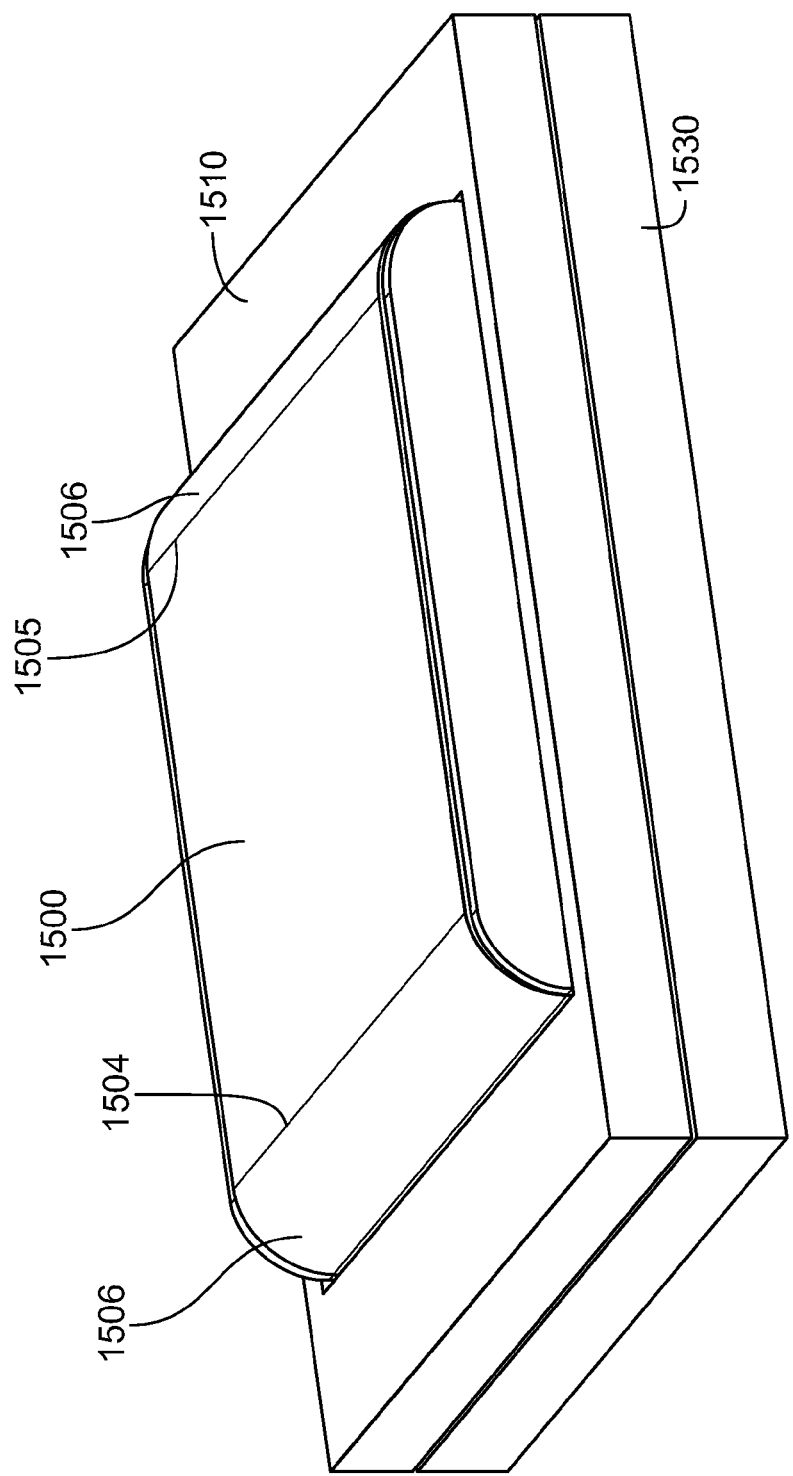
FIG. 15B is a side perspective view of the tensioning device of FIG. 15A straining skin treatment device of FIG. 15B.

FIGS. 15A to 15B illustrate a method and device for straining a skin treatment device 1500. A strainable skin treatment device 1500 is coupled over a window 1520 of a frame 1510 interfacing side 1515 of the frame 1510. The device 1500 may include extension sheets 1506 coupled at sides 1504, 1505 of the device 1500. The extension sheets 1506 may be flexible and relatively less elastic or inelastic than device 1500. A straining device 1530 comprises a protruding element 1535 on a handle 1538 where the protruding element 1535 is shaped to fit within the window 1520 of the frame 1510. In use, the protruding element 1535 is placed between adjacent the treatment device 1500 and is used to push the treatment device 1500 through the window 1520, thereby straining the treatment device 1500. The handle 1538 and frame 1510 may be used together to apply the strained device 1500 to skin to be treated.

Figure 16A:
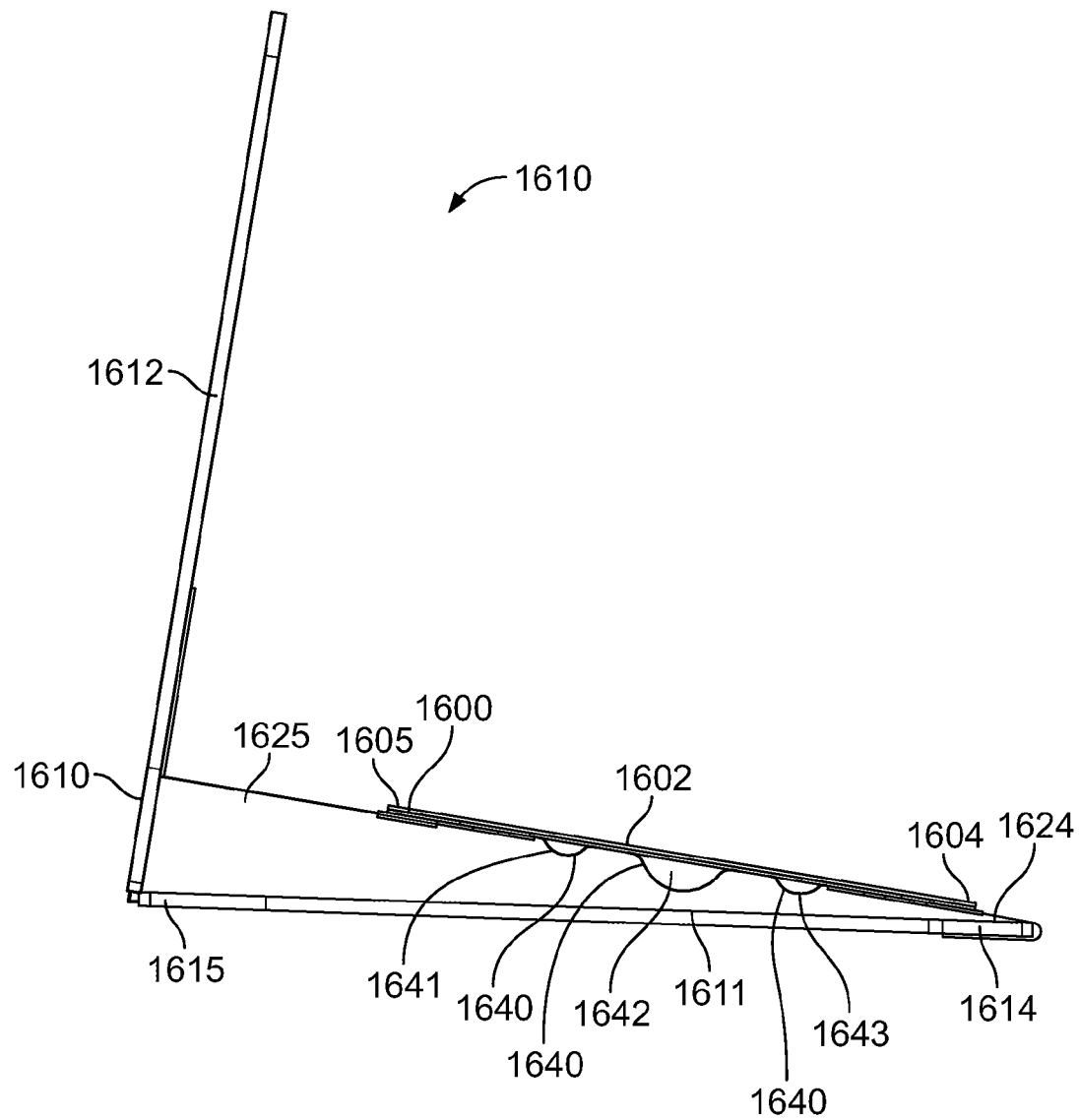
FIG. 16A is a side elevated view a dressing and tensioning device.
Figure 16B:
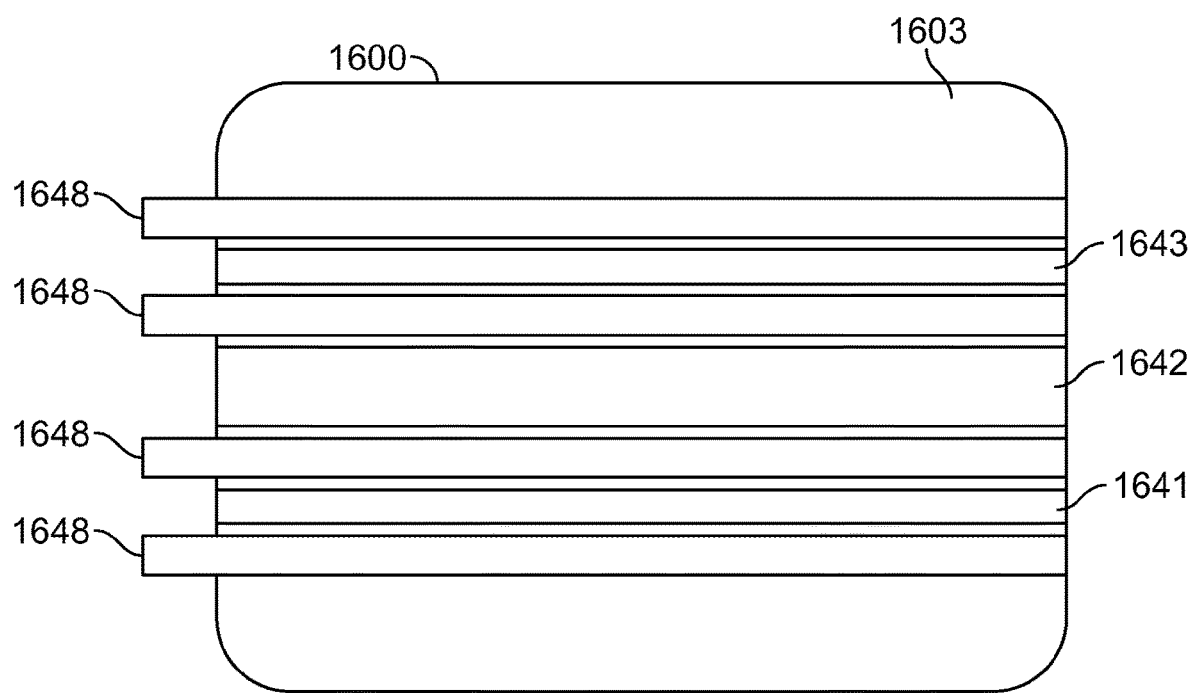
FIG. 16B is a top view of the dressing of FIG. 16A.

FIG. 16A illustrates a strainable dressing 1600 with an applicator or tensioning device 1610 that is described in detail in U.S. patent application Ser. No. 13/345,524 incorporated in its entirety herein by reference. The dressing 1600 may be strained to different distances to accommodate for multiple forces and tensile strengths within the dressing. Different forces may be desired at different locations, areas or parts of the dressing. The dressing 1600 is illustrated in an unstrained configuration in FIG. 16A. A flexible, relatively inelastic anchor sheet 1624 couples a first side 1604 of the device 1600 of a free side 1614 of a base support 1611 of the applicator 1610. A straining sheet 1625 couples a second side 1605 of the device 1600 to the movable cover 1612 which is pivotably or hingedly coupled the side 1615 of the base support 1611. When the cover 1612 is pivoted and opened, it acts to strain the device 1600. A skin adhesive is applied to the skin adhesive side 1602 of the device 1600. A strain limiting structure 1640 is coupled to the device 1600, e.g., the opposing back surface 1603 of the device 1600. The strain limiter 1640 comprises a plurality of strain limiting elements 1641, 1642, 1643. Each strain limiting element may provide a different degree of strain limitation. According to a variation, a first central strain limiter 1642 may permit a predetermined amount of strain at a central location. Adjacent strain limiters 1641, 1643 may permit a predetermined amount of strain that may or may not be different and may or may not be more or less than the amount of central strain. According to a variation, the adjacent strain limiters 1641, 1643 permit a lesser amount of strain than the central strain limiter 1642. Varied strain at different locations may be selected or provided on different dressings to provide a variety of dressings that may be targeted to particular body locations or applications of use.

According to a variation, in order to reduce irritation around the edges or to focus compressive forces near a wound or treatment site, the dressing may be strained to a greater degree, or force towards the middle of the dressing. Also forces and tensile strengths may be controlled towards the edges of the dressings within the dressing.

The strain limiters may be constructed of a flexible less elastic, as compared to the dressing material, such as an LDPE that limits strain between opposing locations where the strain limiter is coupled to the dressing. The strain limiting elements 1641, 1642, 1643 may be attached to the back surface of the dressing with a tape 1648 such as KAPTON® tape, or peelable adhesive. An acrylic adhesive may be used to attach the LDPE to the back side of the kapton. After the dressing is strained and applied to a subject, the strain limiter may or may not be released.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

The invention claimed is:

1. A scar amelioration system comprising:
   a frame comprising a rectangular window;
   a strainable skin treatment device comprising an elastic sheet and removably coupled around a perimeter of a skin interfacing side of the frame so that the elastic sheet is covering the window; and
   a rigid straining device comprising a handle with a rectangular protruding element configured to push orthogonally through the window of the frame on the skin interfacing side and protrude from an opposite side of the frame when the handle abuts the skin interfacing side of the frame to strain the strainable skin treatment device.

2. The system of claim 1, further comprising an attachment structure comprising at least one extension sheet, wherein the strainable skin treatment device is coupled to the frame with the at least one extension sheet.

3. The system of claim 2, further comprising a release element configured to release the at least one extension sheet from the strainable skin treatment device.

4. The system of claim 3, wherein the release element comprises a perforation in the at least one extension sheet.

5. The system of claim 2, wherein the at least one extension sheet is less elastic than the strainable skin treatment device.

6. The system of claim 1, wherein the strainable skin treatment device comprises a skin adhesive on a skin interfacing side of the elastic sheet.

7. A method for ameliorating scar formation in a closed wound using a scar amelioration system comprising:
   a frame comprising a rectangular window;
   a strainable skin treatment device comprising an elastic sheet and removably coupled around a perimeter of a skin interfacing side of the frame so that the elastic sheet is covering the window; and
   a rigid straining device comprising a handle with a rectangular protruding element configured to push orthogonally through the window of the frame on the skin interfacing side and protrude from an opposite side of the frame when the handle abuts the skin interfacing side of the frame to strain the strainable skin treatment device;

the method comprising the steps of:

straining the elastic sheet attached to the frame by a predetermined amount by pushing the rectangular protruding element attached to the handle through the rectangular window of the frame until the handle abuts the frame;

adhering the elastic sheet to a skin of a subject adjacent a previously closed wound; and releasing the skin treatment device from the frame.

* * * * *